United States Patent
Wood et al.

(10) Patent No.: US 8,895,787 B2
(45) Date of Patent: *Nov. 25, 2014

(54) COMPOSITIONS COMPRISING A DEHALOGENASE SUBSTRATE AND A RADIONUCLIDE AND METHODS OF USE

(75) Inventors: Keith V. Wood, Mt. Horeb, WI (US); Georgyi V. Los, Madison, WI (US); Robert F. Bulleit, Verona, WI (US); Dieter Klaubert, Arroyo Grande, CA (US); Mark McDougall, Arroyo Grande, CA (US); Chad Zimprich, Stoughton, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/450,233

(22) Filed: Apr. 18, 2012

(65) Prior Publication Data

US 2012/0258470 A1    Oct. 11, 2012

Related U.S. Application Data

(60) Continuation of application No. 12/975,020, filed on Dec. 21, 2010, now Pat. No. 8,257,939, which is a division of application No. 11/786,792, filed on Apr. 12, 2007, now Pat. No. 7,867,726, which is a division of application No. 10/768,976, filed on Jan. 30, 2004, now Pat. No. 7,238,842.

(60) Provisional application No. 60/444,094, filed on Jan. 31, 2003, provisional application No. 60/474,659, filed on May 30, 2003.

(51) Int. Cl.
| | | |
|---|---|---|
| C07C 19/00 | (2006.01) | |
| C07C 21/00 | (2006.01) | |
| G01N 33/53 | (2006.01) | |
| C12Q 1/34 | (2006.01) | |
| C12N 9/24 | (2006.01) | |

(52) U.S. Cl.
USPC ............. 570/101; 435/7.72; 435/18; 435/195

(58) Field of Classification Search
USPC ............................ 570/101; 435/7.72, 18, 195
See application file for complete search history.

(56) References Cited

U.S. PATENT DOCUMENTS

| | | | |
|---|---|---|---|
| 3,131,122 | A | 4/1964 | Freter |
| 4,574,079 | A | 3/1986 | Gavras et al. |

(Continued)

FOREIGN PATENT DOCUMENTS

| | | |
|---|---|---|
| BE | 616245 | 10/1962 |
| CZ | 3202-87.K | 3/1989 |

(Continued)

OTHER PUBLICATIONS

Adachi et al. "Site-directed mutants, at position 166, of RTEM-1 beta-lactamase that form a stable acyl-enzyme intermediate with penicillin," J Biol Chem, 266(5), pp. 3186-91 (1991).

(Continued)

Primary Examiner — Roseanne Kosson
(74) Attorney, Agent, or Firm — Casimir Jones SC

(57) ABSTRACT

A mutant hydrolase optionally fused to a protein of interest is provided. The mutant hydrolase is capable of forming a bond with a substrate for the corresponding nonmutant (wild-type) hydrolase which is more stable than the bond formed between the wild-type hydrolase and the substrate. Substrates for hydrolases comprising one or more functional groups are also provided, as well as methods of using the mutant hydrolase and the substrates of the invention. Also provided is a fusion protein capable of forming a stable bond with a substrate and cells which express the fusion protein.

14 Claims, 20 Drawing Sheets

(56) References Cited

U.S. PATENT DOCUMENTS

| | | | |
|---|---|---|---|
| 4,777,269 | A | 10/1988 | Scheper |
| 4,818,807 | A | 4/1989 | Morita et al. |
| 5,071,469 | A | 12/1991 | Artz |
| 5,099,020 | A | 3/1992 | Grote et al. |
| 5,110,833 | A | 5/1992 | Mosbach |
| 5,128,247 | A | 7/1992 | Koller |
| 5,372,944 | A | 12/1994 | Swanson |
| 5,476,770 | A | 12/1995 | Pradelles |
| 5,503,977 | A | 4/1996 | Johnsson et al. |
| 5,523,209 | A | 6/1996 | Ginsberg et al. |
| 5,576,424 | A | 11/1996 | Mao et al. |
| 5,700,908 | A | 12/1997 | Ruoslahti |
| 5,700,935 | A | 12/1997 | Takenishi et al. |
| 5,786,428 | A | 7/1998 | Arnold et al. |
| 5,821,047 | A | 10/1998 | Garrard et al. |
| 5,932,421 | A | 8/1999 | Ginsberg et al. |
| 5,945,526 | A | 8/1999 | Lee et al. |
| 6,255,461 | B1 | 7/2001 | Mosbach et al. |
| 6,333,154 | B1 | 12/2001 | Ladant et al. |
| 6,416,733 | B1 | 7/2002 | Barrett et al. |
| 6,492,560 | B2 | 12/2002 | Wilbur et al. |
| 6,537,776 | B1 | 3/2003 | Short |
| 6,800,453 | B2 | 10/2004 | Labaer et al. |
| 7,078,504 | B2 | 7/2006 | Short et al. |
| 7,238,842 | B2 | 7/2007 | Wood et al. |
| 7,425,436 | B2 | 9/2008 | Darzins et al. |
| 7,429,472 | B2 | 9/2008 | Darzins et al. |
| 2002/0042055 | A1 | 4/2002 | Affholter |
| 2002/0137171 | A1 | 9/2002 | Short et al. |
| 2003/0166957 | A1 | 9/2003 | Benneteau et al. |
| 2004/0152880 | A1 | 8/2004 | Minden |
| 2005/0048580 | A1 | 3/2005 | Labaer et al. |
| 2005/0095651 | A1 | 5/2005 | Camarero et al. |
| 2006/0024808 | A1 | 2/2006 | Darzins et al. |
| 2007/0087400 | A1 | 4/2007 | Darzins et al. |
| 2007/0224620 | A1 | 9/2007 | Hartzell et al. |
| 2008/0145882 | A1 | 6/2008 | Darzins et al. |
| 2008/0274488 | A1 | 11/2008 | Darzins et al. |
| 2009/0098627 | A1 | 4/2009 | Darzins et al. |

FOREIGN PATENT DOCUMENTS

| | | |
|---|---|---|
| CZ | 259396 | 10/1998 |
| EP | 0718300 | 6/1996 |
| GB | 2378246 A | 2/2003 |
| WO | 98/36080 | 8/1998 |
| WO | 01/53303 | 7/2001 |
| WO | 01/60415 | 8/2001 |
| WO | 01/77668 | 10/2001 |
| WO | 02/28841 | 4/2002 |
| WO | 02/057411 | 7/2002 |
| WO | 02/068583 | 9/2002 |
| WO | 02/083937 | 10/2002 |
| WO | 03/040096 | 5/2003 |
| WO | 2004/009788 | 1/2004 |
| WO | 2004/072232 | 8/2004 |
| WO | 2006/093529 | 9/2006 |
| WO | 2007/092579 | 8/2007 |
| WO | 2008/054821 | 5/2008 |

OTHER PUBLICATIONS

Affholter et al., "Recombinant Haloaliphatic Dehalogenases," EMBL Database, Genetic Sequence, Entry Name: EMBL:BD057138 (2002).

Akiyama et al. "N-Hydroxy Amides, Part 8. Synthesis and Fe (III) Holding Properties of di0 and Trihydroxamic Acids Extending from Benezenedi- and Tricarbonyl Units through Oligo(ethyleneoxy) Arms," J Chem Soc Perkin Transactions, 2 Physical Org Chem, 9, pp. 1213-1218 (1989).

Amat-Guerri et al., "Methacrylate-tethered analogs o the laser dye PM567 synthesis, copolymerization, with methyl methacrylate and photostabilit of the copolymers," Phytochem Photobiol, 77(6), pp. 577-584 (2003).

Anonymous, "Lecturer Abstracts" The 2N Symposium on Biological Imaging, Online: URL:http://www.promega-rd/info/bioimage/2002/abstracts/lecturer/default.asp [Abstract] (2003).

Anonymous, "The Second Symposium on Biological Imaging: New Dimensions in In Vivo Imaging," Lecturer Abstracts, obtained from www.promega-rd.info/bioimage2003/abstracts/lecture/default.asp (2003).

U.S. Appl. No. 10/768,976—Final Office Action (mailed Mar. 14, 2006) 9 pgs.

U.S. Appl. No. 10/768,976—Non Final Office Action (mailed Aug. 1, 2006) 7 pgs.

U.S. Appl. No. 10/768,976—Non Final Office Action (mailed Sep. 9, 2005) 12 pgs.

U.S. Appl. No. 10/768,976—Notice of Allowance mailed Dec. 15, 2006, 11 pgs.

U.S. Appl. No. 10/768,976—Preliminary Amendment and Response to Restriction Requirement filed Aug. 5, 2005, 22 pgs.

U.S. Appl. No. 10/768,976—Response filed Jan. 24, 2006 to Non Final office action mailed Sep. 9, 2005, 21 pgs.

U.S. Appl. No. 10/768,976—Response filed Jul. 11, 2006 to Final Office Action mailed Mar. 14, 2006 13 pgs.

U.S. Appl. No. 10/768,976—Response filed Nov. 1, 2006 to Non Final Office Action mailed Aug. 1, 2006 (13 pgs).

U.S. Appl. No. 10/768,976—Restriction Requirement mailed Jun. 2, 2005, 11 pgs.

U.S. Appl. No. 11/006,031—Advisory Action Mailed May 7, 2007, 3 pgs.

U.S. Appl. No. 11/006,031—Amendment and Response filed Apr. 25, 2007 to Final Office Action mailed Feb. 8, 2007 34 pgs.

U.S. Appl. No. 11/006,031—Non Final office Action mailed Mar. 15, 2006, 15 pgs.

U.S. Appl. No. 11/006,031—Response filed Feb. 17, 2006 to Restriction Requirement mailed Dec. 21, 2005, 34 pgs.

U.S. Appl. No. 11/006,031—Response filed Jul. 5, 2007 to Advisory Action mailed May 7, 2007 and Final Office Acton mailed May 28, 2007, 32 pgs.

U.S. Appl. No. 11/006,031—Response filed Aug. 31, 2007 to Restriction Requirement mailed Jul. 31, 2007, 37 pgs.

U.S. Appl. No. 11/006,031—Response filed Dec. 22, 2006 to Non Final Office Action mailed Aug. 9, 2006, 37 pgs.

U.S. Appl. No. 11/006,031—Restriction Requirement mailed Dec. 21, 2005, 20 pgs.

U.S. Appl. No. 11/006,031—Final office Action Mailed Feb. 8, 2007 8 pgs.

U.S. Appl. No. 11/006,031—Non Final Office Action mailed Aug. 9, 2006, 13 pgs.

U.S. Appl. No. 11/006,031—Notice of Allowance mailed Apr. 24, 2008, 7 pgs.

U.S. Appl. No. 11/006,031—Notice of Allowance mailed Oct. 30, 2007 8 pgs.

U.S. Appl. No. 11/006,031—Response filed Jul. 6, 2006 to Non Final Office Action mailed Mar. 15, 2006, 35 pgs.

U.S. Appl. No. 11/006,031—Restriction Requirement mailed Jul. 31, 2007, 8 pgs.

U.S. Appl. No. 11/194,110—Non Final Office Action, mailed Mar. 29, 2007 21 pgs.

U.S. Appl. No. 11/194,110—Notice of Allowance mailed Aug. 15, 2007 12 pgs.

U.S. Appl. No. 11/194,110—Notice of Allowance Mailed Dec. 3, 2007, 6 pgs.

U.S. Appl. No. 11/194,110—Preliminary Amendment mailed Oct. 31, 2007, 6 pgs.

U.S. Appl. No. 11/194,110—Response and Preliminary Amendment filed Feb. 7, 2007 to Restriction Requirement mailed Jan. 4, 2007, 21 pgs.

U.S. Appl. No. 11/194,110—Restriction Requirement mailed Jan. 4, 2007 14 pgs.

U.S. Appl. No. 11/194,110—Response filed Jun. 29, 2007 to Non Final Office Action mailed Mar. 29, 2007, 20 pgs.

U.S. Appl. No. 11/194,110—Supplementary Preliminary Amendment mailed Nov. 14, 2007, 6pgs.

U.S. Appl. No. 11/704,150—Response filed May 6, 2009 to Restriction Requirement mailed Mar. 30, 2009, 10 pgs.

(56) References Cited

OTHER PUBLICATIONS

U.S. Appl. No. 11/704,150—Restriction Requirement mailed Mar. 30, 2009, 11 pgs.
U.S. Appl. No. 11/704,150 Non Final Office Action mailed Sep. 8, 2009 12pgs.
U.S. Appl. No. 11/709,150—Preliminary Amendment filed May 11, 2007 12 pgs.
U.S. Appl. No. 11/786,792—Preliminary Amendment Filed Apr. 12, 2007.
U.S. Appl. No. 11/786,792—Preliminary Amendment Filed Aug. 17, 2007.
U.S. Appl. No. 12/220,478—Preliminary Amendment filed Dec. 2, 2008 3 pgs.
U.S. Appl. No. 12/284,010—Non Final Office Action Mailed Mar. 23, 2009, 30 pgs.
U.S. Appl. No. 12/284,010—Preliminary Amendment Filed Aug. 17, 2008 18 pgs.
U.S. Appl. No. 12/284,010—Response filed Jul. 10, 2009 to Non Final Office Action mailed Mar. 23, 2009 17 pgs.
Arand et al., "Sequence similarity of mammalian epoxide hydrolases to the bacterial haloalkane dehalogenase and other related proteins," FEBS Lett, 338, pp. 251-256 (1994).
Indian Patent Office Action for Application No. 3867/DELNP/2005 dated Sep. 9, 2008.
Instant Notes—Chemistry for Biologists, 2nd edition, Fisher and Arnolds, Garland Science/Bios Scientific Publishers, pp. 245-256 (2004).
International Application No. PCT/US2005/027307—International Preliminary Report on Patentability mailed Feb. 20, 2007.
International Search Report and Written Opinion for Application No. PCT/US2007/023205 dated Nov. 3, 2008.
International Search Report and Written Opinion for Application No. PCT/US2005/027307 dated Jan. 29, 2007.
International Search Report and Written Opinion for Application No. PCT/US2007/003416 dated Sep. 14, 2007.
Japanese Office Action for Application No. 2006-503174 mailed Oct. 27, 2009.
Jeong et al., "Kinase assay based on thiophosphorylation and biotinylation," Biotechniques, 27 (6), pp. 1232-1238 (1999).
Jones et al., "Solvolysis mechanisms, SN1-like behavior of methyl chloromethyl ether, sensitivity to solvent ionizing power and alpha-deuterium isotope effect," J Amer Chem Soc, 89, pp. 4863-4867 (1967).
Keppler et al., "A general method for the covalent labeling of fusion proteins with small molecules in vivo," Nature Biotechnol, 21, pp. 86-89 (2003).
Kulakova et al., "The plasmid-located Haloalkane Dehalogenase Gene From *Rhodococcus rhodochrous* NCIMB 13064," Microbiology, 143, pp. 109-115 (1997).
Kurihara et al., "Comprehensive Site-directed Mutagenesis of L-2Halo Acid Dehalogenase to Probe Catalytic Amino Acid Residue," J Biochem, 117, pp. 1317-1322 (1995).
Kwon et al., "Antibody Arrays Prepared by Cutinase-Mediated Immobilization on Self-Assembled Monolayers," Anal Chem, 76, pp. 5713-5720 (2004).
Lautens et al., "An Expedient Route for the Stereoselective Construction of Bridged Polyheterocyclic Ring Systems Using the Tandem "Pincer" Diels-Alder Reaction," J Org Chem, 62, pp. 4418-4427 (1997).
Lewis et al., "Detection and quantification of biotinylated proteins using the storm 840 optical scanner," J Nutri Biochem, 14, pp. 196-202 (2003).
Li et al., "A Modified Mammalian Tandem Affinity Purification Procedure to Prepare Functional Polycystin-2 Channel" FEBS Letters, 576, pp. 231-236 (2004).
Lin et al., "Methods for Labeling Quantum Dots to Biomolecules," J Neurosci Nanotechnol, 4, pp. 641-645 (2004).
Los et al., "Chapter 14—The Halo Tagtm—a novel technology for cell imaging and protein analysis," Methods Molec Biol, 356, pp. 195-208 (2007).
Luo et al., "A Glucose based on Chitsosan-Glucose Oxidase-Gold Nanoparticles Biocomposite Formed by One-Step Endrodeposition," Analytical Biochem, 334, pp. 284-289 (2004).
Manoury et al., "Synthesis of a series of compounds related to betaxolol, a new beta 1-adrenoceptor antagonist with a pharmacological and pharmacokinetic profile optimized for the treatment of chronic cardiovascular diseases," J Med Chem, 30, pp. 1003-1011 (1987).
Mathieu et al., "Monitoring E-Selection-Mediated Adhesion Using Green and Red Fluorescent Proteins," J Immunol Methods, 272, pp. 81-92 (2003).
Michl et al., Electronic Aspects of Organic Photochemistry, John Wiley and Sons, pp. 61-78 (1990).
Miller et al., "Selective chemical labeling of proteins in living cells," Curr Opin Chem Biol, 9, pp. 56-61 (2005).
Momose et al., "Novel 5-Substituted-1H-Tetrazole Derivatives as Potent Glucose and Lipid Lowering Agents," Chemical & Pharmaceutical Bulletin, Pharmaceutical Society of Japan, 50, pp. 100-111 (2002).
Morzycki et al., "Synthesis of Dimeric Steroids as Components of Lipid Membranes," Tetrahedron, 53(30), pp. 10579-10590 (1997).
PCT Application No. PCT/US2004/002607 International Preliminary Report on Patentability mailed Jun. 23, 2005 16 pgs.
Pieters, et al., "Design and Synthesis of Reagants for phage display screening of dehalogenases," Bioorganic & Medicinal Chem Lett, 9, pp. 161-166 (1999).
Pries et al., "Activation of an Asp-124 -> Asn Mutant of Haloalkane Dehalogenase by Hydrolytic Deamidation of Asparagine," FEBS Lett, 358, pp. 171-174 (1995).
Pries et al., "Histidine 289 is essential for hydrolysis for the alkyl-enzyme intermediate of haloalkane dehalogenase," J Biol Chem, 270, pp. 10405-10411 (1995).
Puig et al., "The Tandem Affinity Purification (TAP) Method: A General Procedure of Protein Complex Function," Methods, 24, pp. 218-229 (2001).
Rohila et al., "Improved Tandem Affinity Purification Tag and Methods for Isolation of Protein Heterocomplexes from Plants," Plant J, 38, pp. 172-181 (2004).
Santra et al., "Luminescent Nanoparticle Probes for Bioimaging," J Nanosci Nanotechnol, 4, pp. 590-599 (2004).
Stroffekova et al., "The protein-labeling reagent FLASH-EDT2 binds not only to CCXXCC motifs but also nonspecifically to endogenous cysteine-rich proteins," Pfulgers Arch, 442, pp. 859-866 (2001).
Stryer, et al. "Biochemistry," Third Edition, pp. 757-758 (1988).
Tou et al., "Kinetic study of the stabilities of chloromethyl ether and bis(chloromethyl) ether in humid air," Analyt. Chem, 46, pp. 1866-1869 (1974).
US Patent Office Action for U.S. Appl. No. 11/006,031 dated May 7, 2007.
US Patent Office Action for U.S. Appl. No. 11/509,796 dated Mar. 28, 2008.
US Patent Office Action for U.S. Appl. No. 11/509,796 dated Apr. 11, 2007.
US Patent Office Action for U.S. Appl. No. 11/509,796 dated Sep. 24, 2007.
US Patent Office Action for U.S. Appl. No. 11/509,796 dated Nov. 12, 2008.
US Patent Office Action for U.S. Appl. No. 11/786,792 dated Nov. 2, 2009.
US Patent Office Action for U.S. Appl. No. 12/075,160 dated Nov. 16, 2009.
US Patent Office Action for U.S. Appl. No. 12/075,160 dated May 24, 2010.
US Patent Office Action for U.S. Appl. No. 12/220,478 dated Jun. 10, 2010.
US Patent Office Action for U.S. Appl. No. 12/284,010 dated Sep. 29, 2009.
US Patent Office Action for U.S. Appl. No. 12/284,010 dated Jul. 10, 2010.
Aravind, "An evolutionary classification of the metallo-beta-lactamase fold proteins, " In Silico Biol, 1(2), pp. 69-91 (1999).

(56) References Cited

OTHER PUBLICATIONS

Australian Application Serial No. 2004211584, First Examiner Report mailed Jan. 6, 2009.
Banas et al., "Mechanism of enhanced conversion of 1,2,3-trichloropropane by mutant haloalkane dehalogenase revealed by molecular modeling," J Comp Aided Molec Design, 20(6), pp. 375-383 (2006).
Banks et al., "Understanding Fluorescene Polarization and its Data Analysis—Physical Principles of Fluorescene Polarization," http://www.perkinelmer.com/lifesciences, 12 pgs. (2001).
Bier, "Covalys—one tag does it all," Market Portrait, pp. 46-47 (2003).
Bodwell et al., "Synthesis, Structure and AM1 Conformational Study of [3] Paracyclo [3] (1,3) indolophane, a Novel Chiral Cyclophane," Tetrahedron, 55(45): pp. 12939-12956 (1999).
Bosma et al., "Biodegradation of 1,2,3-trichloropropane through directed evolution and heterologous expression of a haloalkane dehalogenase gene," Appl Environ Microbiol, pp. 3582-3587 (2002).
Campbell et al., "A Monomeric Red Fluorescent Protein," PNAS, 99(12), pp. 7877-7882 (2002).
Castro et al., "Biodehalogenation, reductive reactivities of microbial and mammalian cytochromes P-450 compared with heme and whole—cell models," J Agric Food Chem, 36,pp. 915-919 (1988).
Chaloupkova, "Modification of activity and specificity of haloalkane dehalogenase from Sphingomonas paucimobilis UT26 by engineering of its entrance tunnel," J Biol Chem, pp. 52622-52628 (2003).
Chen et al., "Site-specific labeling of proteins with small molecules in live cells," Curr Opin Biotech, 16, pp. 35-40 (2005).
Chen et al., "Relocation of the Catalytic Carboxylate Group in Class a Beta-lactamase: The Structure and Function of the Mutant Enzyme Glu-166-Gln: Asn-170" Protein Engineer, 12(7), pp. 573-579 (1999).
Cheuk, "Synthesis of Optically Active Poly(Phenylacetylenes) Containing Amino Acid Pendent Groups," Polymeric Mater Sci Engineer, 82, pp. 56-57 (2000).
Chinese Application Serial No. 200480008194.4 Response filed to Second Office Action mailed May 22, 2009 14 pgs.
Chinese Patent Application No. 200480008194.4—Office Action dated Oct. 9, 2009 with English transl.
Chinese Patent Application No. 20048000819A First Office Action mailed Dec. 22, 2006, 8 pgs.
Chinese Patent Application No. 20048000819A Response filed Jul. 6, 2007 to the First Action mailed Dec. 22, 2006, 27 Pg.
Cohen et al., "Synthesis of Some Substituted Dibenzodiazenpinones and Pyridobenzodiazepinones," J Heter Chem, 35, pp. 675-686 (1998).
Dahl et al., "The reactivity of affinity labels: a kinetic study of the reaction of alkyl halides with thiolate anions—a model reaction for protein alkylation," Bioorg Chem, 10, pp. 329-341 (2005).
Database EMBL EBI, Accession No. BD051738 (2004).
Dorwald et al., "Side reactions in organic synthesis," A Guide of Successful Synthesis Design, Wiley: VCH, (2005) 4 pages.
Doubrovin et al., "Reviews—Multimodality in Vivo Molecular—Genetic Imaging," Bioconjugate Chem, 15, pp. 1376-1388 (2004).
European Application Serial No. 04707032.1—Communication mailed Jun. 22, 2009 14 pgs.
European Patent Application Ser No. 0407032.1—Communication pursuant to Article 96(2) EPC mailed Mar. 12, 2007 3 pgs.
European Patent Application Ser No. 0407032.1 Response Filed Sep. 18, 2007 to Examining Division's Communication mailed Mar. 12, 2007, 37 pgs.
European Patent Office Action for Application No. 05857556.4 dated May 7, 2009.
European Patent Office Action for Application No. 07763411.1 dated Dec. 17, 2008.
European Patent Office Action for Application No. 07763411.1 dated Mar. 17, 2009.
European Patent Office Action for Application No. 07867352.2 dated Feb. 1, 2010.
Franken et al., "Crystal Structure of haloalkane dehalogenase: an enzyme to detoxify halogenated alkanes," EMBO J, 10(6), pp. 1297-1302 (1991).
Gambhir, "Molecular Imaging of Cancer with Positron Emission Tomography," Nature Reviews, 2, pp. 683-693 (2002).
Gao et al., "Construction of murine phage antibody library and selection of ricin-specific single chanin antibodies," IUBMB Life, 48(5), pp. 513-517 (1999).
Gibbons et al., "Chipper: Discovering Transcription Factor Targets from Chromatin Immunoprecipitation Microarrays Using Variance Stabilization," Genome Biology, 6(11), Article R96 (2005).
Gite et al., "Ultrasensitive Fluorescence-Based Detection of Nascent Proteins in Gels," Analytical Biochem, 279, pp. 218-225 (2000).
Gould et al., "Tandem Affinity Purification and Identification of Protein Complex Components," Methods, 33, pp. 239-244 (2004).
Gray et al., "Rapid Evolution of reversible denaturation and elevated melting temperature in a microbial haloalkane dehalogenase," Adv. Synth. Catayl, pp. 601-617 (2001).
Griffin et al., "Specific covalent labeling of recombinant protein molecules inside live cells," Science, 281, pp. 269-72 (1998).
Gurskaya et al., " GFP-like Chromoproteins as a Source of Far-red Fluorescent Proteins," FEBS Letters, 507, pp. 16-20 (2001).
Hall et al., "Regulation of Gene Expression by a Metabolic Enzyme," Science, 306, pp. 482-484 (2004).
Heck et al., "Aromatic haloethylation with palladium and copper halides," J Amer Chem Soc, 90, pp. 5538-5542 (1968).
Henze et al., "The number of structurally isomeric alcohols of the methanol series," J Amer Chem Soc, 53, pp. 3042-3046 (1931).
Hodneland et al., "Selective Immobilization of Proteins to Self-Assembled Monolayers Presenting Active Site-Directed Directed Capture Ligands," Proc Natl Acad Sci USA, 99(8), pp. 5048-5052 (2002).
Holloway et al., "A Colorimetric Assay for Detecting Haloalkine Dehalogenase Activity," J Microbiol Materials, 32, pp. 31-36 (1998).
Horton et al., "Reactions with reactive alkyl halidies," Meth Enyzmol, 11, pp. 556-565 (1967).
Huber et al., "SPR-based Interaction Studies with Small Molecular Weight Ligands Using hAGT Fusion Proteins," Anayl Biochem, 333, pp. 280-88 (2004).
Hynkova et al., "Identification of the Catalytic Triad in the Haloalkane Dehalogenase from Sphingomonas paucimobilis UT26" FEBS Letters, 446, pp. 177-181 (1999).
Ichiyama et al., "Novel Catalytic Mechanism of Nucleophilic Subsitution by Asparagine Residue Involving Cyanoalanine Intermediate Revealed by Mass Spectrometric Monitoring of an Enzyme Reaction," J Biol Chem, 275, pp. 40804-40809 (2000).
Indian Application Serial No. 3867/DELNP/2005 First Examination Report dated Sep. 28, 2007.
Vincze et al., "Three-Dimensional Trace Element Analysis by Cofocal X-Ray Microfluorescence Imaging," Analytical Chem, 76, pp. 6786-6791 (2004).
Wada et al., "Application of the remote photocyclization with a pair system of phthamlimide and methylthio groups. A photochemical synthesis of crown ether analogs," Chem Pharm Bull, 31, pp. 429-435 (1983).
Wada et al., "Codon usage tabulated from the GenBank genetic sequence data," Nucleic Acids Res, pp. 2111-2118 (1992).
Wang et al., "Detection of Tumor Marker CA125 in Ovarian Carcinoma Using Quantum Dots," Acta Biochem Biophys, 36(10), pp. 681-686 (2004).
Wayback Machine, http://www.promega-rd.info/bioimage2003/abstracts/lecturer/default.asap (Mar. 17,2007).
Weissleder et al., "Shedding Light Onto Live Molecular Targets," Nature Med, 9, pp. 123-128 (2003).
Wheeler et al., "Conjugation of haloalkanes by bacterial and mammalian glutathione transferases: mono and vicinal dihaloethanes," Chem Res Toxicol, 14, 1107-1117 (2001).
Winberg et al., "The Catalytic Triad in Short-Chain Dehyrdogenases," Dept of Biochem, Inst. of Med Biol, Univ of Tromso, Abstract, (2002).
Wolfgang et al., "Nonhuman primate transgenesis: progress and prospects," Trends in Biotechnol, 20(11), pp. 479-484 (2002).

(56) References Cited

OTHER PUBLICATIONS

Yang, G. et al., "Identification of Active Site Residues Essential to 4-chlorobenzoyl-Coenzyme a Dehalogenase Catalysis by Chemical Modification and Site Directed Mutagenesis," Biochemistry, 35, pp. 10879-10885 (1996).

Yang, M. et al., "Whole-Body Optical Imaging of Green Fluorescent Protein-Expressing Tumors and Metastases," PNAS, 97, pp. 1206-1211 (2000).

Yokota et al., "Purification and Properties of Haloalkane Dehalogenase from *Corynebacterium* Sp. Strain M15-3," J Bacteriology, 169, pp. 4094-4054.

Zawadzke et al., "Elimination of the hydrolytic water molecule in a class a beta-lactamase mutant: crystal structure and kinetics," Biochemistry, pp. 16475-16485 (1996).

Zeph et al., "Use of biotinylated DNA probe to detect bacteria transduced by bacteriophage P1 in soil," Appl Environ Microbiol, 55(3), pp. 661-665 (1989).

Fetzner S. et al., "Bacterial dehalogenases: biochemistry, gentetics, and biotechnological applications." Microbiological Reviews 1994, 58(4):641-685, 1994.

Hes Van R. et al., "SLV310, a novel, potential antipsychotic, combining potent dopamine D2 receptor antagonism with serotonin reuptake inhibition." Bioorganic & Medical Chemistry Letters 2003, 1393):405-408.

Curragh et al., "Haloalkane degradation and assimilation by *Rhodococcus rhodochrous* NCIMB 13064." Microbiology 1994, 140:1433-1442.

"Functional group," Encyclopedia Britannica Article online, http://www.searced.com/eb/article-9035655 (Mar. 19, 2007).

International Search Report for Corresponding PCT application No. PCT/US2004/002607 (Oct. 26, 2004).

Partial Search Report for corresponding PCT Application No. PCT/US2005/027307 (Jun. 11, 2006).

"Valence" Hawley's Condensed Chemical Dictionary (14th Ed) Online, John Wiley and Sons, 2002, http://www.knovel.com/knovel2/Toc.jsp?BookID=704&VerticlID=0 (Mar. 20, 2007).

Ladd et al., "Polymeric Gadolinium Chelate Magnetic Resonance Imaging Contrast Agents: Design, Synthesis, and Properties." Bioconjugate Chem. 1999, 10: 361-370.

Froidevaux et al., "A Gallium-Labeled Dota-α-Melanocyte—Stimulating Hormone Analog for PET Imaging of Melanoma Metastases." J. Nucl. Med. 2004; 45:116-123.

Meares et al., "Macrocytic chelattes of radiometals for diagnosis and therapy." Br. J. Cancer 1990, 62 (Suppl. X): 21-26.

Aime et al., "Novel Paramagnetic Macromolecular Complexes Derived from the Linkage of a Macrocyclic Gd(III) Complex to Polyamino Acids through a Squaric Acid Moiety." Bioconjugate Chem. 1999, 10:192-199.

1 2 3 4   5 6

1 2 3 4 5 6 7 8 9 10 11 12 13 14

1 2 3 4 5 6 7 8 9 10

1 2 3 4 5 6 7         1 2 3 4 5 6 7 8
  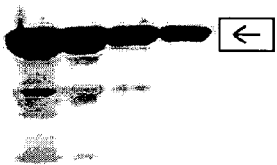
FIG. 14A              FIG. 14B
1 2 3 4 5 6 7 8
FIG. 15

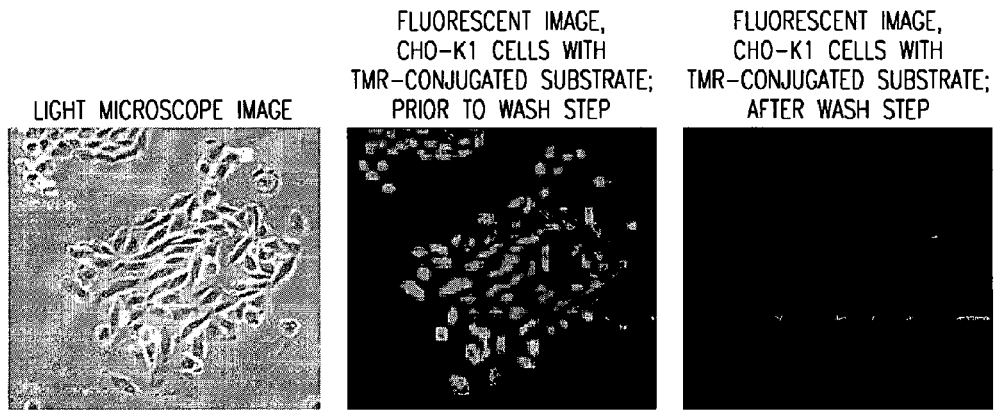

LIGHT MICROSCOPE IMAGE

FIG. 16A

FLUORESCENT IMAGE, CHO-K1 CELLS WITH TMR-CONJUGATED SUBSTRATE; PRIOR TO WASH STEP

FIG. 16B

FLUORESCENT IMAGE, CHO-K1 CELLS WITH TMR-CONJUGATED SUBSTRATE; AFTER WASH STEP

FIG. 16C

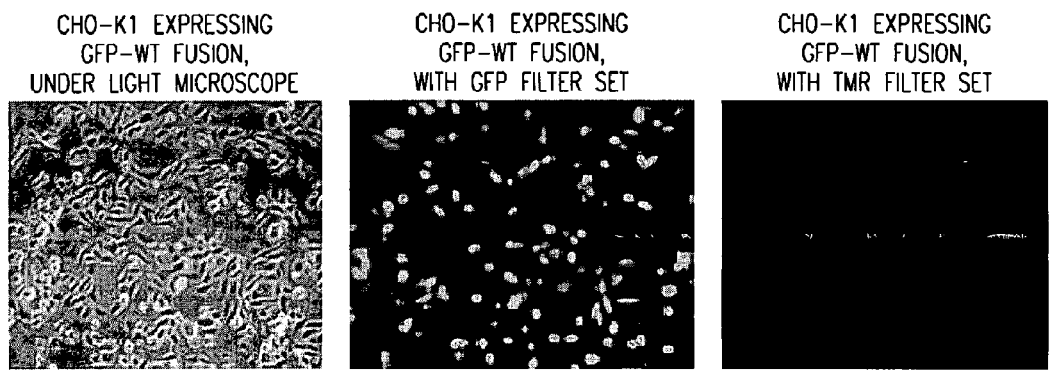

CHO-K1 EXPRESSING GFP-WT FUSION, UNDER LIGHT MICROSCOPE

FIG. 17A

CHO-K1 EXPRESSING GFP-WT FUSION, WITH GFP FILTER SET

FIG. 17B

CHO-K1 EXPRESSING GFP-WT FUSION, WITH TMR FILTER SET

FIG. 17C

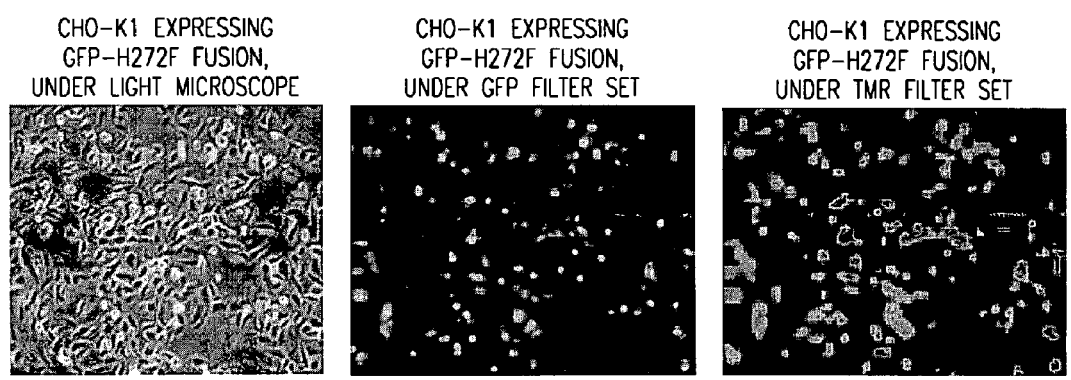

CHO-K1 EXPRESSING GFP-H272F FUSION, UNDER LIGHT MICROSCOPE

FIG. 17D

CHO-K1 EXPRESSING GFP-H272F FUSION, UNDER GFP FILTER SET

FIG. 17E

CHO-K1 EXPRESSING GFP-H272F FUSION, UNDER TMR FILTER SET

FIG. 17F

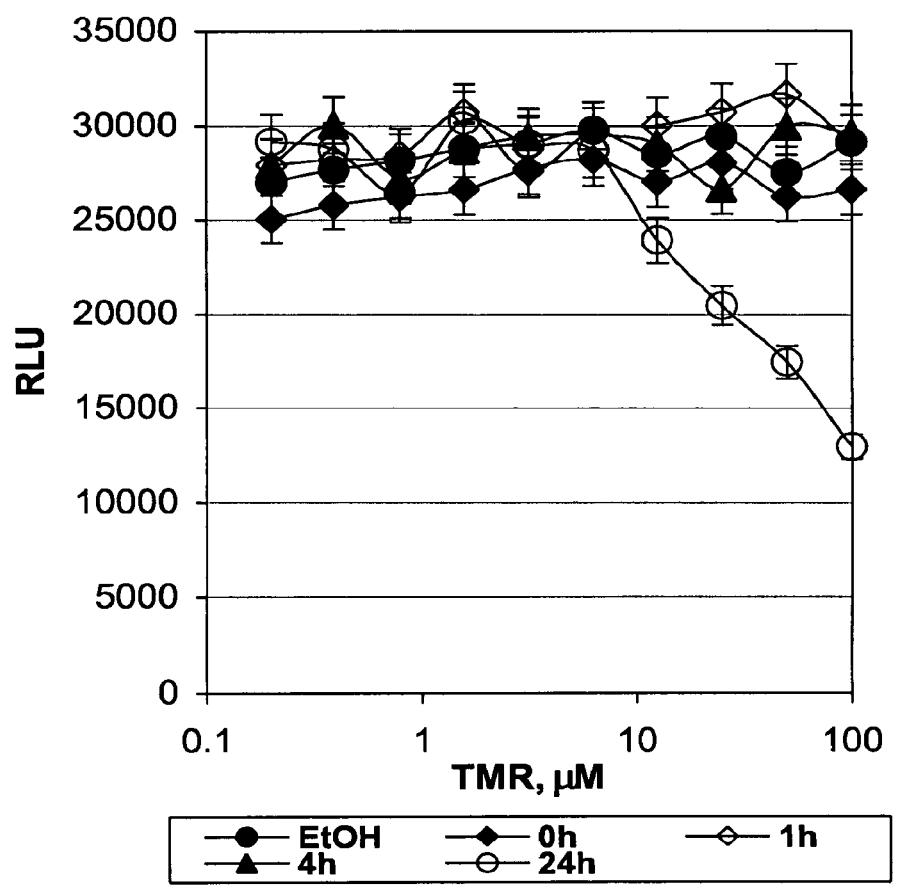
FIG. 18
FIG. 19A 1 2 3 4 5
FIG. 22
1 2 3 4 5
FIG. 23

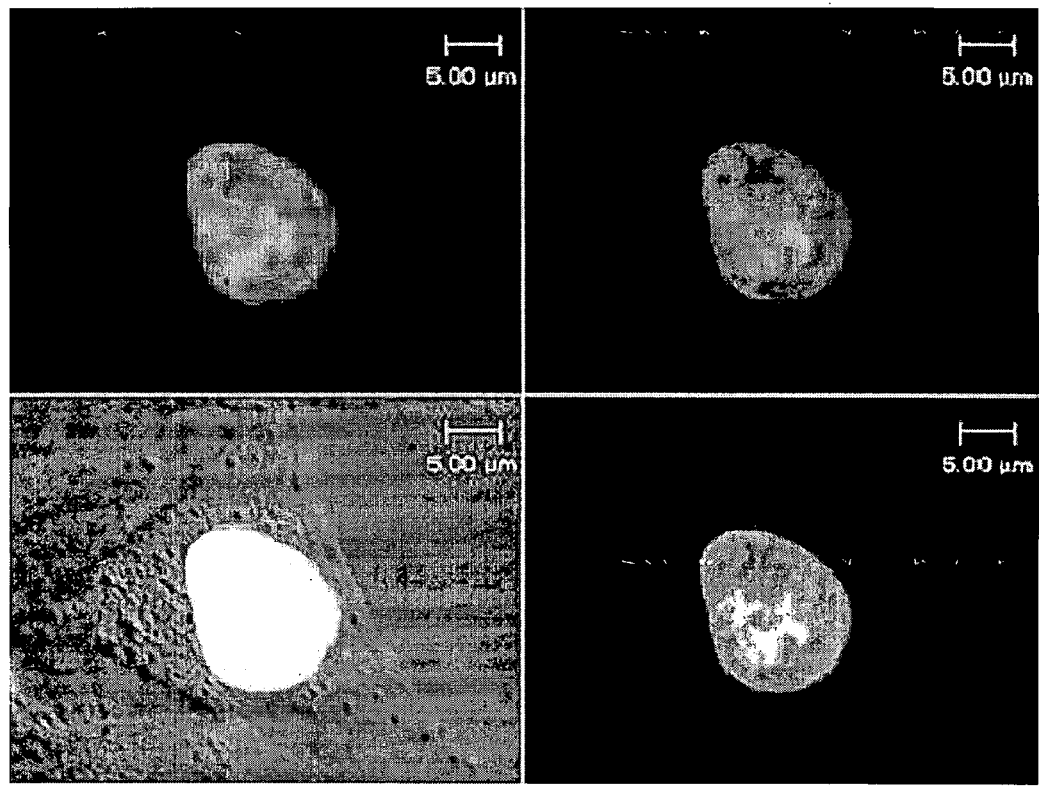
FIG. 24
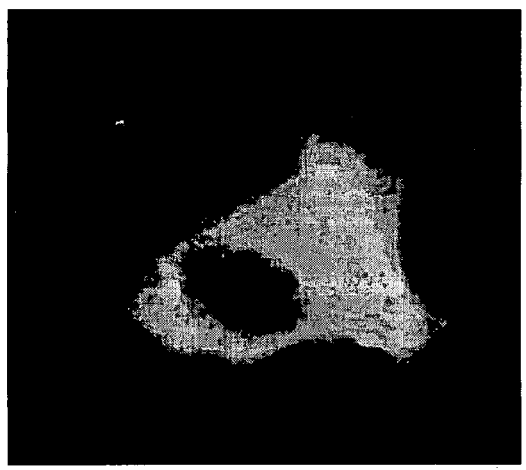 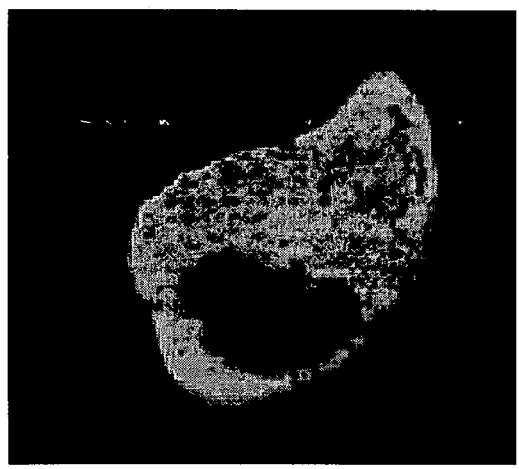
FIG. 25A  FIG. 25B 1  2  3

1  2  3

SEQUENCE LISTING

<160> NUMBER OF SEQ ID NOS: 64

<210> SEQ ID NO 1
<211> LENGTH: 31
<212> TYPE: DNA
<213> ORGANISM: Rhodococcus rhodochrous

<400> SEQUENCE: 1
gcttcacttg tcgtcatcgt ccttgtagtc a                                    31

<210> SEQ ID NO 2
<211> LENGTH: 31
<212> TYPE: DNA
<213> ORGANISM: Rhodococcus rhodochrous

<400> SEQUENCE: 2
gcttcacttg tcgtcatcgt ccttgtagtc a                                   31

<210> SEQ ID NO 3
<211> LENGTH: 27
<212> TYPE: DNA
<213> ORGANISM: Artificial Sequence
<220> FEATURE:
<223> OTHER INFORMATION: A synthetic primer

<400> SEQUENCE: 3
ccgggattgt tctacctcca ggaagac                                        27

<210> SEQ ID NO 4
<211> LENGTH: 27
<212> TYPE: DNA
<213> ORGANISM: Artificial Sequence
<220> FEATURE:
<223> OTHER INFORMATION: A synthetic primer

<400> SEQUENCE: 4
ccgggattgg cctacctcca ggaagac                                        27

<210> SEQ ID NO 5
<211> LENGTH: 27
<212> TYPE: DNA
<213> ORGANISM: Artificial Sequence
<220> FEATURE:
<223> OTHER INFORMATION: A synthetic primer

<400> SEQUENCE: 5
ccgggattgc agtacctcca ggaagac                                        27

<210> SEQ ID NO 6
<211> LENGTH: 27
<212> TYPE: DNA
<213> ORGANISM: Artificial Sequence
<220> FEATURE:
<223> OTHER INFORMATION: A synthetic primer

<400> SEQUENCE: 6
ccgggattgg gctacctcca ggaagac                                        27

<210> SEQ ID NO 7
<211> LENGTH: 37
<212> TYPE: DNA
<213> ORGANISM: Artificial Sequence
<220> FEATURE:
<223> OTHER INFORMATION: A synthetic primer

<400> SEQUENCE: 7
acgcgtcgac gccgccatgt cagaaatcgg tacaggc                             37

<210> SEQ ID NO 8
<211> LENGTH: 55
<212> TYPE: DNA
<213> ORGANISM: Artificial Sequence
<220> FEATURE:
<223> OTHER INFORMATION: A synthetic primer

<400> SEQUENCE: 8
ataagaatgc ggccgctcaa gcgcttcaac cggtgagtgc ggggagccag cgcgc          55

<210> SEQ ID NO 9
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 9
ccggtgacta caaggacgat gacgacaagt gaagc          35

<210> SEQ ID NO 10
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 10
gcttcacttg tcgtcatcgt ccttgtagtc a          31

<210> SEQ ID NO 11
<211> LENGTH: 31
<212> TYPE: DNA
<213> ORGANISM: Artificial Sequence
<220> FEATURE:
<223> OTHER INFORMATION: A synthetic primer

<400> SEQUENCE: 11
gcttcacttg tcgtcatcgt ccttgtagtc a          31

<210> SEQ ID NO 12
<211> LENGTH: 31
<212> TYPE: DNA
<213> ORGANISM: Artificial Sequence
<220> FEATURE:
<223> OTHER INFORMATION: A synthetic primer

<400> SEQUENCE: 12
gcttcacttg tcgtcatcgt ccttgtagtc a          31

<210> SEQ ID NO 13
<211> LENGTH: 43
<212> TYPE: DNA
<213> ORGANISM: Artificial Sequence
<220> FEATURE:
<223> OTHER INFORMATION: A synthetic primer

<400> SEQUENCE: 13
cttgggtttg gaagaggtcg tcctggtcat ccactgctgg ggc          43

<210> SEQ ID NO 14
<211> LENGTH: 42
<212> TYPE: DNA
<213> ORGANISM: Artificial Sequence
<220> FEATURE:
<223> OTHER INFORMATION: A synthetic primer

<400> SEQUENCE: 14
tgagccccag cagtggatga ccaggacgac ctcttccaaa cc          42

<210> SEQ ID NO 15
<211> LENGTH: 29

```
<212> TYPE: DNA
<213> ORGANISM: Artificial Sequence
<220> FEATURE:
<223> OTHER INFORMATION: A synthetic primer

<400> SEQUENCE: 15
ggaatgggcc ctctagagcg acgatgtca                                 29

<210> SEQ ID NO 16
<211> LENGTH: 26
<212> TYPE: DNA
<213> ORGANISM: Artificial Sequence
<220> FEATURE:
<223> OTHER INFORMATION: A synthetic primer

<400> SEQUENCE: 16
cagtcagtca cgatggatcc gctcaa                                    26

<210> SEQ ID NO 17

<400> SEQUENCE: 17

000

<210> SEQ ID NO 18

<400> SEQUENCE: 18

000

<210> SEQ ID NO 19
<211> LENGTH: 5
<212> TYPE: PRT
<213> ORGANISM: Artificial Sequence
<220> FEATURE:
<223> OTHER INFORMATION: A synthetic affinity molecule

<400> SEQUENCE: 19

His His His His His
1               5

<210> SEQ ID NO 20
<211> LENGTH: 6
<212> TYPE: PRT
<213> ORGANISM: Artificial Sequence
<220> FEATURE:
<223> OTHER INFORMATION: A synthetic affinity molecule

<400> SEQUENCE: 20

His His His His His His
1               5

<210> SEQ ID NO 21
<211> LENGTH: 10
<212> TYPE: PRT
<213> ORGANISM: Artificial Sequence
<220> FEATURE:
<223> OTHER INFORMATION: A synthetic affinity molecule

<400> SEQUENCE: 21

Glu Gln Lys Leu Ile Ser Glu Glu Asp Leu
1               5                   10

<210> SEQ ID NO 22
<211> LENGTH: 8
<212> TYPE: PRT
<213> ORGANISM: Artificial Sequence
```

```
<220> FEATURE:
<223> OTHER INFORMATION: A synthetic affinity molecule

<400> SEQUENCE: 22

Asp Tyr Lys Asp Asp Asp Asp Lys
1               5

<210> SEQ ID NO 23
<211> LENGTH: 8
<212> TYPE: PRT
<213> ORGANISM: Artificial Sequence
<220> FEATURE:
<223> OTHER INFORMATION: A synthetic affinity molecule

<400> SEQUENCE: 23

Trp Ser His Pro Gln Phe Glu Lys
1               5

<210> SEQ ID NO 24
<211> LENGTH: 9
<212> TYPE: PRT
<213> ORGANISM: Artificial Sequence
<220> FEATURE:
<223> OTHER INFORMATION: A synthetic affinity molecule

<400> SEQUENCE: 24

Tyr Pro Tyr Asp Val Pro Asp Tyr Ala
1               5

<210> SEQ ID NO 25

<400> SEQUENCE: 25

000

<210> SEQ ID NO 26
<211> LENGTH: 45
<212> TYPE: DNA
<213> ORGANISM: Artificial Sequence
<220> FEATURE:
<223> OTHER INFORMATION: A synthetic oligonucleotide

<400> SEQUENCE: 26
atcgaaggtc gtgggatccc caggaattcc cgggtcgacg ccgcc          45

<210> SEQ ID NO 27
<211> LENGTH: 15
<212> TYPE: PRT
<213> ORGANISM: Artificial Sequence
<220> FEATURE:
<223> OTHER INFORMATION: A synthetic peptide

<400> SEQUENCE: 27

Ile Glu Gly Arg Gly Ile Pro Arg Asn Ser Arg Val Asp Ala Ala
1               5                   10                  15

<210> SEQ ID NO 28
<211> LENGTH: 51
<212> TYPE: DNA
<213> ORGANISM: Artificial Sequence
<220> FEATURE:
<223> OTHER INFORMATION: A synthetic oligonucleotide

<400> SEQUENCE: 28
tccggatcaa gcttgggcga cgaggtggac ggcgggccct ctagagccac c     51
```

```
<210> SEQ ID NO 29
<211> LENGTH: 17
<212> TYPE: PRT
<213> ORGANISM: Artificial Sequence
<220> FEATURE:
<223> OTHER INFORMATION: A synthetic peptide

<400> SEQUENCE: 29

Ser Gly Ser Ser Leu Gly Asp Glu Val Asp Gly Gly Pro Ser Arg Ala
1               5                   10                  15

Thr

<210> SEQ ID NO 30
<211> LENGTH: 45
<212> TYPE: DNA
<213> ORGANISM: Artificial Sequence
<220> FEATURE:
<223> OTHER INFORMATION: A synthetic oligonucleotide

<400> SEQUENCE: 30
accggttccg gatcaagctt gcggtaccgc gggccctcta gagcc              45

<210> SEQ ID NO 31
<211> LENGTH: 15
<212> TYPE: PRT
<213> ORGANISM: Artificial Sequence
<220> FEATURE:
<223> OTHER INFORMATION: A synthetic peptide

<400> SEQUENCE: 31

Thr Gly Ser Gly Ser Ser Leu Arg Tyr Arg Gly Pro Ser Arg Ala
1               5                   10                  15

<210> SEQ ID NO 32
<211> LENGTH: 51
<212> TYPE: DNA
<213> ORGANISM: Artificial Sequence
<220> FEATURE:
<223> OTHER INFORMATION: A synthetic oligonucleotide

<400> SEQUENCE: 32
tccggatcaa gcttgcggta ccgcgggccc tctagagccg tcgacgccgc c        51

<210> SEQ ID NO 33
<211> LENGTH: 17
<212> TYPE: PRT
<213> ORGANISM: Artificial Sequence
<220> FEATURE:
<223> OTHER INFORMATION: A synthetic peptide

<400> SEQUENCE: 33

Ser Gly Ser Ser Leu Arg Tyr Arg Gly Pro Ser Arg Ala Val Asp Ala
1               5                   10                  15

Ala

<210> SEQ ID NO 34
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 34
cttgggtttg gaagaggtcg tcctggtcat ccaccagtgg ggc                43
```

<210> SEQ ID NO 35
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 35
tgagccccac tggtggatga ccaggacgac ctcttccaaa cc                          42

<210> SEQ ID NO 36
<211> LENGTH: 1053
<212> TYPE: DNA
<213> ORGANISM: Staphylococcus aureus

<400> SEQUENCE: 36
agcttactat gccattatta ataacttagc catttcaaca ccttctttca aatatttata       60
ataaactatt gacaccgata ttacaattgt aatattattg atttataaaa attacaactg      120
taatatcgga gggtttattt tgaaaaagtt aatattttta attgtaattg ctttagtttt      180
aagtgcatgt aattcaaaca gttcacatgc caaagagtta aatgatttag aaaaaaaata      240
taatgctcat attggtgttt atgctttaga tactaaaagt ggtaaggaag taaaatttaa      300
ttcagataag agatttgcct atgcttcaac ttcaaaagcg ataaatagtg ctattttgtt      360
agaacaagta cctttataata agttaaataa aaaagtacat attaacaaag atgatatagt     420
tgcttattct cctatttag aaaaatatgt aggaaaagat atcactttaa aagcacttat       480
tgaggcttca atgacatata gtgataatac agcaaacaat aaaattataa aagaaatcgg      540
tggaatcaaa aaagttaaac aacgtctaaa agaactagga gataaagtaa caaatccagt      600
tagatatgag atagaattaa attactattc accaaagagc aaaaaagata cttcaacacc      660
tgctgccttc ggtaagaccc ttaataaact tatcgccaat ggaaaattaa gcaaagaaaa      720
caaaaaattc ttacttgatt taatgttaaa taataaaagc ggagatactt taattaaaga      780
cggtgttcca aaagactata aggttgctga taaaagtggt caagcaataa catatgcttc      840
tagaaatgat gttgcttttg tttatcctaa gggccaatct gaacctattg ttttagtcat      900
ttttacgaat aaagacaata aaagtgataa gccaaatgat aagttgataa gtgaaaccgc      960
caagagtgta atgaaggaat tttaatattc taaatgcata ataaatactg ataacatctt     1020
atattttgta ttatattttg tattatcgtt gac                                  1053

<210> SEQ ID NO 37
<211> LENGTH: 81
<212> TYPE: DNA
<213> ORGANISM: Artificial Sequence
<220> FEATURE:
<223> OTHER INFORMATION: A synthetic oligonucleotide

<400> SEQUENCE: 37
ccggtgatcc aaaaaagaag agaaaggtag atccaaaaaa gaagagaaag gtagatccaa       60 aaagaagag aaaggtatga g                                                 81

<210> SEQ ID NO 38
<211> LENGTH: 81
<212> TYPE: DNA
<213> ORGANISM: Artificial Sequence
<220> FEATURE:
<223> OTHER INFORMATION: A synthetic oligonucleotide

<400> SEQUENCE: 38
gatcctcata cctttctctt cttttttgga tctacctttc tcttcttttt tggatctacc    60
tttctcttct tttttggatc a    81

<210> SEQ ID NO 39
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 39
attatgctga gtgatatccc    20

<210> SEQ ID NO 40
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 40
ctcggtacca agctccttgt agtca    25

<210> SEQ ID NO 41
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 41
caaaggtatt gcatgtatgc agttcatccg gcctatcccg    40

<210> SEQ ID NO 42
<211> LENGTH: 44
<212> TYPE: DNA
<213> ORGANISM: Artificial Sequence
<220> FEATURE:
<223> OTHER INFORMATION: A synthetic oligonucleotide

<400> SEQUENCE: 42
gtcaaaggta ttgcatgtat gctgttcatc cggcctatcc cgac    44

<210> SEQ ID NO 43
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 43
aggtattgca tgtatggcgt tcatccggcc tatccc    36

<210> SEQ ID NO 44
<211> LENGTH: 23
<212> TYPE: DNA
<213> ORGANISM: Artificial Sequence
<220> FEATURE:
<223> OTHER INFORMATION: A synthetic primer

<400> SEQUENCE: 44
gggctggcaa gccacgtttg gtg    23

<210> SEQ ID NO 45
<211> LENGTH: 10

-continued

<212> TYPE: DNA
<213> ORGANISM: Artificial Sequence
<220> FEATURE:
<223> OTHER INFORMATION: A synthetic improved Kozak sequence

<400> SEQUENCE: 45
gccaccatgg                                                                 10

<210> SEQ ID NO 46
<211> LENGTH: 36
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: (1)..(36)
<223> OTHER INFORMATION: n = A, T, G, or C

<400> SEQUENCE: 46
nnnngctagc cagctggcga tatcgccacc atggga                                    36

<210> SEQ ID NO 47
<211> LENGTH: 30
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: (1)..(34)
<223> OTHER INFORMATION: n = A, T, G, or C

<400> SEQUENCE: 47
taatagttaa ttaagtaagc ggccgcnnnn                                           30

<210> SEQ ID NO 48
<211> LENGTH: 296
<212> TYPE: PRT
<213> ORGANISM: Artificial Sequence
<220> FEATURE:
<223> OTHER INFORMATION: A synthetic peptide

<400> SEQUENCE: 48

Met Gly Ser Glu Ile Gly Thr Gly Phe Pro Phe Asp Pro His Tyr Val
1               5                   10                  15

Glu Val Leu Gly Glu Arg Met His Tyr Val Asp Val Gly Pro Arg Asp
            20                  25                  30

Gly Thr Pro Val Leu Phe Leu His Gly Asn Pro Thr Ser Ser Tyr Leu
        35                  40                  45

Trp Arg Asn Ile Ile Pro His Val Ala Pro Ser His Arg Cys Ile Ala
    50                  55                  60

Pro Asp Leu Ile Gly Met Gly Lys Ser Asp Lys Pro Asp Leu Asp Tyr
65                  70                  75                  80

Phe Phe Asp Asp His Val Arg Tyr Leu Asp Ala Phe Ile Glu Ala Leu
                85                  90                  95

Gly Leu Glu Glu Val Val Leu Val Ile His Asp Trp Gly Ser Ala Leu
            100                 105                 110

Gly Phe His Trp Ala Lys Arg Asn Pro Glu Arg Val Lys Gly Ile Ala
        115                 120                 125

Cys Met Glu Phe Ile Arg Pro Ile Pro Thr Trp Asp Glu Trp Pro Glu
    130                 135                 140

Phe Ala Arg Glu Thr Phe Gln Ala Phe Arg Thr Ala Asp Val Gly Arg

```
                    145                 150                 155                 160
            Glu Leu Ile Ile Asp Gln Asn Ala Phe Ile Glu Gly Ala Leu Pro Lys
                            165                 170                 175

Cys Val Val Arg Pro Leu Thr Glu Val Glu Met Asp His Tyr Arg Glu
                            180                 185                 190

Pro Phe Leu Lys Pro Val Asp Arg Glu Pro Leu Trp Arg Phe Pro Asn
                            195                 200                 205

Glu Leu Pro Ile Ala Gly Glu Pro Ala Asn Ile Val Ala Leu Val Glu
                            210                 215                 220

Ala Tyr Met Asn Trp Leu His Gln Ser Pro Val Pro Lys Leu Leu Phe
            225                 230                 235                 240

Trp Gly Thr Pro Gly Val Leu Ile Pro Pro Ala Glu Ala Ala Arg Leu
                            245                 250                 255

Ala Glu Ser Leu Pro Asn Cys Lys Thr Val Asp Ile Gly Pro Gly Leu
                            260                 265                 270

Phe Tyr Leu Gln Glu Asp Asn Pro Asp Leu Ile Gly Ser Glu Ile Ala
                            275                 280                 285

Arg Trp Leu Pro Gly Leu Ala Gly
                            290                 295

<210> SEQ ID NO 49
<211> LENGTH: 948
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: (1)..(948)
<223> OTHER INFORMATION: n = A, C, T, or G

<400> SEQUENCE: 49
nnnngctagc cagctggcga tatcgccacc atgggatccg agattgggac agggtttcct       60
tttgatcctc attatgtgga ggtgctgggg gagagaatgc attatgtgga tgtggggcct      120
agagatggga cacctgtgct gtttctgcat gggaatccta catcttctta tctgtggaga      180
aatattattc ctcatgtggc tccttctcat agatgtattg ctcctgatct gattgggatg      240
gggaagtctg ataagcctga tctggattat tttttttgatg atcatgtgag atatctggat     300
gcttttattg aggctctggg gctggaggag gtggtgctgg tgattcatga ttgggggtct      360
gctctggggt tcattgggc taagagaaat cctgagagag tgaaggggat tgcttgtatg       420
gagtttatta gacctattcc tacatgggat gagtggcctg agtttgctag agagacattt      480
caggctttta gaacagctga tgtggggaga gagctgatta ttgatcagaa tgcttttatt      540
gagggggctc tgcctaagtg tgtggtgaga cctctgacag aggtgagat ggatcattat       600 agagagcctt ttctgaagcc tgtggataga gagcctctgt ggagatttcc taatgagctg      660
cctattgctg gggagcctgc taatattgtg gctctggtgg aggcttatat gaattggctg      720
catcagtctc ctgtgcctaa gctgctgttt tgggggacac ctggggtgct gattcctcct      780
gctgaggctg ctagactggc tgagtctctg cctaattgta agacagtgga tattgggcct      840
gggctgtttt atctgcagga ggataatcct gatctgattg gtctgagat tgctagatgg      900 ctgcccgggc tggccggcta atagttaatt aagtaagcgg ccgcnnnn                   948

<210> SEQ ID NO 50
<211> LENGTH: 951
<212> TYPE: DNA
```

<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: (1)..(951)
<223> OTHER INFORMATION: n = A, T, G, or C

<400> SEQUENCE: 50

| | | | |
|---|---|---|---|
| nnnngctagc cagctggcgc ggatatcgcc accatgggat ccgagattgg gacagggttc | | | 60 |
| ccttttgatc ctcactatgt tgaagtgctg ggggaaagaa tgcactacgt ggatgtgggg | | | 120 |
| cctagagatg ggaccccagt gctgttcctc cacgggaacc ctacatctag ctacctgtgg | | | 180 |
| agaaatatta tacctcatgt tgctcctagt cataggtgca ttgctcctga tctgatcggg | | | 240 |
| atggggaagt ctgataagcc tgacttagac tacttttttg atgatcatgt tcgatacttg | | | 300 |
| gatgctttca ttgaggctct ggggctggag gaggtggtgc tggtgataca cgactggggg | | | 360 |
| tctgctctgg ggtttcactg gctaaaagg aatccggaga gagtgaaggg gattgcttgc | | | 420 |
| atggagttta ttcgacctat tcctacttgg gatgaatggc cagagtttgc cagagagaca | | | 480 |
| tttcaagcct ttagaactgc cgatgtgggc agggagctga ttatagacca gaatgctttc | | | 540 |
| atcgagggg ctctgcctaa atgtgtagtc agacctctca ctgaagtaga gatggaccat | | | 600 |
| tatagagagc cctttctgaa gcctgtggat cgcgagcctc tgtggaggtt tccaaatgag | | | 660 |
| ctgcctattg ctggggagcc tgctaatatt gtggctctgg tggaagccta tatgaactgg | | | 720 |
| ctgcatcaga gtccagtgcc caagctactc ttttggggga ctccgggagt tctgattcct | | | 780 |
| cctgccgagc tgctagact ggctgaatcc ctgcccaatt gtaagaccgt ggacatcggc | | | 840 |
| cctgggctgt tttacctcca agaggacaac cctgatctca tcgggtctga gatcgcacgg | | | 900 |
| tggctgcccg ggctggccgg ctaatagtta attaagtagg cggccgcnnn n | | | 951 |

<210> SEQ ID NO 51
<211> LENGTH: 882
<212> TYPE: DNA
<213> ORGANISM: Rhodococcus rhodochrous

<400> SEQUENCE: 51

| | | | |
|---|---|---|---|
| atgtcagaaa tcggtacagg cttccccttc gaccccatt atgtggaagt cctgggcgag | | | 60 |
| cgtatgcact acgtcgatgt tggaccgcgg gatggcacgc ctgtgctgtt cctgcacggt | | | 120 |
| aacccgacct cgtcctacct gtggcgcaac atcatcccgc atgtagcacc gagtcatcgg | | | 180 |
| tgcattgctc cagacctgat cgggatggga aaatcggaca aaccagacct cgattatttc | | | 240 |
| ttcgacgacc acgtccgcta cctcgatgcc ttcatcgaag ccttgggttt ggaagaggtc | | | 300 |
| gtcctggtca tccacgactg gggctcagct ctcggattcc actgggccaa gcgcaatccg | | | 360 |
| gaacgggtca aaggtattgc atgtatggaa ttcatccggc ctatcccgac gtgggacgaa | | | 420 |
| tggccggaat cgcccgtga gaccttccag gccttccgga ccgccgacgt cggccgagag | | | 480 |
| ttgatcatcg atcagaacgc tttcatcgag ggtgcgctcc cgaaatgcgt cgtccgtccg | | | 540 |
| cttacggagg tcgagatgga ccactatcgc gagcccttcc tcaagcctgt gaccgagag | | | 600 |
| ccactgtggc gattccccaa cgagctgccc atcgccggtg agcccgcgaa catcgtcgcg | | | 660 |
| ctcgtcgagg catacatgaa ctggctgcac cagtcacctg tcccgaagtt gttgttctgg | | | 720 |
| ggcacacccg gcgtactgat cccccggcc gaagccgcga gacttgccga aagcctcccc | | | 780 |
| aactgcaaga cagtggacat cggcccggga ttgcactacc tccaggaaga caacccggac | | | 840 |
| cttatcggca gtgagatcgc gcgctggctc cccgcactct ag | | | 882 |

<210> SEQ ID NO 52
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 52
cttgggtttg gaagaggtcg tcctggtcat ccacgaatgg ggc        43

<210> SEQ ID NO 53
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 53
tgagccccat tcgtggatga ccaggacgac ctcttccaaa cc         42

<210> SEQ ID NO 54
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 54
cttgggtttg gaagaggtcg tcctggtcat ccactactgg ggc        43

<210> SEQ ID NO 55
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 55
tgagccccag tagtggatga ccaggacgac ctcttccaaa cc         42

<210> SEQ ID NO 56
<211> LENGTH: 38
<212> TYPE: DNA
<213> ORGANISM: Artificial Sequence
<220> FEATURE:
<223> OTHER INFORMATION: A synthetic primer

<400> SEQUENCE: 56
ccagttagat atgacataga attaaattac tattcacc              38

<210> SEQ ID NO 57
<211> LENGTH: 38
<212> TYPE: DNA
<213> ORGANISM: Artificial Sequence
<220> FEATURE:
<223> OTHER INFORMATION: A synthetic primer

<400> SEQUENCE: 57
ggtgaatagt aatttaattc tatgtcatat ctaactgg              38

<210> SEQ ID NO 58
<211> LENGTH: 38
<212> TYPE: DNA
<213> ORGANISM: Artificial Sequence
<220> FEATURE:

<223> OTHER INFORMATION: A synthetic primer

<400> SEQUENCE: 58
ccagttagat atgagataga attacagtac tattcacc                                38

<210> SEQ ID NO 59
<211> LENGTH: 38
<212> TYPE: DNA
<213> ORGANISM: Artificial Sequence
<220> FEATURE:
<223> OTHER INFORMATION: A synthetic primer

<400> SEQUENCE: 59
ggtgaatagt actgtaattc tatctcatat ctaactgg                                38

<210> SEQ ID NO 60
<211> LENGTH: 38
<212> TYPE: DNA
<213> ORGANISM: Artificial Sequence
<220> FEATURE:
<223> OTHER INFORMATION: A synthetic primer

<400> SEQUENCE: 60
ccagttagat atgacataga attacagtac tattcacc                                38

<210> SEQ ID NO 61
<211> LENGTH: 38
<212> TYPE: DNA
<213> ORGANISM: Artificial Sequence
<220> FEATURE:
<223> OTHER INFORMATION: A synthetic primer

<400> SEQUENCE: 61
ggtgaatagt actgtaattc tatgtcatat ctaactgg                                38

<210> SEQ ID NO 62
<211> LENGTH: 40
<212> TYPE: DNA
<213> ORGANISM: Artificial Sequence
<220> FEATURE:
<223> OTHER INFORMATION: A synthetic primer

<400> SEQUENCE: 62
caacaggtcg acgccgccat gaaagagtta aatgatttag                              40

<210> SEQ ID NO 63
<211> LENGTH: 36
<212> TYPE: DNA
<213> ORGANISM: Artificial Sequence
<220> FEATURE:
<223> OTHER INFORMATION: A synthetic primer

<400> SEQUENCE: 63
gtagtcaccg gtaaattcct tcattacact cttggc                                  36

<210> SEQ ID NO 64
<211> LENGTH: 4
<212> TYPE: PRT
<213> ORGANISM: Artificial Sequence
<220> FEATURE:
<223> OTHER INFORMATION: A synthetic peptide

<400> SEQUENCE: 64

Asp Glu Val Asp
1

COMPOSITIONS COMPRISING A DEHALOGENASE SUBSTRATE AND A RADIONUCLIDE AND METHODS OF USE

CROSS-REFERENCE TO RELATED APPLICATIONS

This application is a continuation of U.S. application Ser. No. 12/975,020, filed Dec. 21, 2010, which is a divisional of U.S. patent application Ser. No. 11/786,792, filed Apr. 12, 2007, issued as U.S. Pat. No. 7,867,726 on Jan. 11, 2011, which is a Divisional of U.S. patent application Ser. No. 10/768,976, filed Jan. 30, 2004, issued as U.S. Pat. No. 7,238,842 on Jul. 3, 2007, which claims the benefit of the filing date of to U.S. application Ser. No. 60/444,094 filed Jan. 31, 2003 and U.S. application Ser. No. 60/474,659 filed May 30, 2003, under U.S.C. §119(e), and incorporates those applications by reference herein.

FIELD OF THE INVENTION

This invention relates to the field of biochemical assays and reagents. More specifically, this invention relates to mutant proteins covalently linked (tethered) to one or more functional groups and to methods for their use.

BACKGROUND OF THE INVENTION

The specific detection of molecules is a keystone in understanding the role of that molecule in the cell. Labels, e.g., those that are covalently linked to a molecule of interest, permit the ready detection of that molecule in a complex mixture. The label may be one that is added by chemical synthesis in vitro or attached in vivo, e.g., via recombinant techniques. For instance, the attachment of fluorescent or other labels onto proteins has traditionally been accomplished by in vitro chemical modification after protein purification (Hermanson, 1996). For in vivo attachment of a label, green fluorescent protein (GFP) from the jellyfish *Aequorea victoria* can be genetically fused with many host proteins to produce fluorescent chimeras in situ (Tsien, 1998; Chalfie et al., 1998). However, while GFP-based indicators are currently employed in a variety of assays, e.g., measuring pH (Kneen et al., 1998; Llopis et al., 1998; Miesenböck et al., 1998), $Ca^{2+}$ (Miyawaki et al., 1997; Rosomer et al., 1997), and membrane potential (Siegel et al., 1997), the fluorescence of intrinsically labeled proteins such as GFP is limited by the properties of protein structure, e.g., a limited range of fluorescent colors and relatively low intrinsic brightness (Cubitt et al., 1995; Ormö et al., 1996), and To address the deficiencies of GFP labeling in situ, Griffen et al. (1998) synthesized a tight-binding pair of molecular components: a small receptor domain composed of as few as six natural amino acids and a small (<700 dalton), synthetic ligand that could be linked to various spectroscopic probes or crosslinks. The receptor domain included four cysteines at the i, i+1, i+4, and i+5 positions of an αhelix and the ligand was 4',5'-bis(1,3,2-dithioarsolan-2-yl)fluorescein (FLASH). Griffen et al. disclose that the ligand had relatively few binding sites in nontransfected mammalian cells, was membrane-permeant and was nonfluorescent until it bound with high affinity and specificity to a tetracysteine domain in a recombinant protein, resulting in cells being fluorescently labeled ("FLASH" labeled) with a nanomolar or lower dissociation constant. However, with respect to background binding in cells, Stroffekova et al. (2001) disclose that FLASH-$EDT_2$ binds non-specifically to endogenous cysteine-rich proteins. Furthermore, labeling proteins by FLASH is limited by the range of fluorophores that may be used.

Receptor-mediated targeting methods use genetically encoded targeting sequences to localize fluorophores to virtually any cellular site, provided that the targeted protein is able to fold properly. For example, Farinas et al. (1999) disclose that cDNA transfection was used to target a single-chain antibody (sFv) to a specified site in a cell. Farinas et al. disclose that conjugates of a hapten (4-ethoxymethylene-2-phenyl-2-oxazolin-5-one, phOx) and a fluorescent probe (e.g., BODIPY Fl, tetramethylrhodamine, and fluorescein) were bound with high affinity (about 5 nM) to the subcellular site for the sFv in living Chinese hamster ovary cells, indicating that the targeted antibody functioned as a high affinity receptor for the cell-permeable hapten-fluorophore conjugates. Nevertheless, functional sFv expression may be relatively poor in reducing environments.

Thus, what is needed is an improved method to label a desired protein.

SUMMARY OF THE INVENTION

The invention provides methods, compositions and kits for tethering (linking), e.g., via a covalent or otherwise stable bond, one or more functional groups to a protein of the invention or to a fusion protein (chimera) which includes a protein of the invention. A protein of the invention is structurally related to a wild-type (native) hydrolase but comprises at least one amino acid substitution relative to the corresponding wild-type hydrolase and binds a substrate of the corresponding wild-type hydrolase but lacks or has reduced catalytic activity relative to the corresponding wild-type hydrolase (which mutant protein is referred to herein as a mutant hydrolase). The aforementioned tethering occurs, for instance, in solution or suspension, in a cell, on a solid support or at solution/surface interfaces, by employing a substrate for a hydrolase which includes a reactive group and which has been modified to include one or more functional groups. As used herein, a "substrate" includes a substrate having a reactive group and optionally one or more functional groups. A substrate which includes one or more functional groups is generally referred to herein as a substrate of the invention. As used herein, a "functional group" is a molecule which is detectable or is capable of detection (e.g., a chromophore, fluorophore or luminophore), or can be bound or attached to a second molecule (e.g., biotin, hapten, or a cross-linking group) or includes one or more amino acids, e.g., a peptide or polypeptide including an antibody or receptor, one or more nucleotides, lipids including lipid bilayers, a solid support, e.g., a sedimental particle, and the like. A functional group may have more than one property such as being capable of detection and being bound to another molecule. As used herein a "reactive group" is the minimum number of atoms in a substrate which are specifically recognized by a particular wild-type or mutant hydrolase of the invention. The interaction of a reactive group in a substrate and a wild-type hydrolase results in a product and the regeneration of the wild-type hydrolase. A substrate, e.g., a substrate of the invention, may also optionally include a linker, e.g., a cleavable linker.

A substrate useful in the invention is one which is specifically bound by a mutant hydrolase, and preferably results in a bond formed with an amino acid, e.g., the reactive residue, of the mutant hydrolase which bond is more stable than the bond formed between the substrate and the corresponding amino acid of the wild-type hydrolase. While the mutant hydrolase specifically binds substrates which may be specifically bound by the corresponding wild-type hydrolase, no product or substantially less product, e.g., 2-, 10-, 100-, or 1000-fold less, is formed from the interaction between the mutant hydrolase and the substrate under conditions which result in product formation by a reaction between the corresponding wild-type hydrolase and substrate. The lack of, or reduced amounts of, product formation by the mutant hydrolase is due to at least one substitution in the mutant hydrolase, which substitution results in the mutant hydrolase forming a bond with the substrate which is more stable than the bond formed between the corresponding wild-type hydrolase and the substrate. Preferably, the bond formed between a mutant hydrolase and a substrate of the invention has a half-life (i.e., $t_{1/2}$) that is at least 2-fold, and more preferably at least 4- or even 10-fold, and up to 100-, 1000- or 10,000-fold, greater than the $t_{1/2}$ of the bond formed between a corresponding wild-type hydrolase and the substrate under conditions which result in product formation by the corresponding wild-type hydrolase. Preferably, the bond formed between the mutant hydrolase and the substrate has a $t_{1/2}$ of at least 30 minutes and preferably at least 4 hours, and up to at least 10 hours, and is resistant to disruption by washing, protein denaturants, and/or high temperatures, e.g., the bond is stable to boiling in SDS.

In one embodiment, the substrate is a substrate for a dehalogenase, e.g., a haloalkane dehalogenase or a dehalogenase that cleaves carbon-halogen bonds in an aliphatic or aromatic halogenated substrate, such as a substrate for *Rhodococcus, Staphylococcus, Pseudomonas, Burkholderia, Agrobacterium* or *Xanthobacter* dehalogenase, or a substrate for a serine beta-lactamase. In one embodiment, a substrate of the invention optionally includes a linker which physically separates one or more functional groups from the reactive group in the substrate. For instance, for some mutant hydrolases, i.e., those with deep catalytic pockets, a substrate of the invention can include a linker of sufficient length and structure so that the one or more functional groups of the substrate of the invention do not disturb the 3-D structure of the hydrolase (wild-type or mutant). For example, one example of a substrate of the invention for a dehalogenase includes a reactive group such as $(CH_2)_{2-3}X$ where X is a halide and a functional group such as tetramethylrhodamine (TAMRA), e.g., TAMRA-$C_{14}H_{24}O_4$—Cl.

In one embodiment, a linker is preferably 12 to 30 atoms in length. The linker may not always be present in a substrate of the invention, however, in some embodiments, the physical separation of the reactive group and the functional group may be needed so that the reactive group can interact with the reactive residue in the mutant hydrolase to form a covalent bond. Preferably, when present, the linker does not substantially alter, e.g., impair, the specificity or reactivity of a substrate having the linker with the wild-type or mutant hydrolase relative to the specificity or reactivity of a corresponding substrate which lacks the linker with the wild-type or mutant hydrolase. Further, the presence of the linker preferably does not substantially alter, e.g., impair, one or more properties, e.g., the function, of the functional group.

Thus, the invention provides a compound of formula (I): R-linker-A-X, wherein R is one or more functional groups, wherein the linker is a multiatom straight or branched chain including C, N, S, or O, wherein A-X is a substrate for a dehalogenase, and wherein X is a halogen. In one embodiment, an alkylhalide is covalently attached to a linker, L, which is a group or groups that covalently attach one or more functional groups to form a substrate for a dehalogenase. As described herein, a mutant dehalogenase, DhaA.H272F, was bound to substrates for DhaA which included 5-(and 6-) carboxy fluorescein (FAM), e.g., FAM-$C_{14}H_{24}O_4$—Cl, TAMRA, e.g., TAMRA-$C_{14}H_{24}O_4$—Cl, and biotin, e.g., biotin-$C_{18}H_{32}O_4$—Cl, and there was no significant quenching effect of this binding on FAM or TAMRA fluorescence or on biotin binding to streptavidin. As also described herein, a mutant dehalogenase, e.g., DhaA.D106C and DhaA.D106E as well as DhaA.D106C:H272F and DhaA.D106E:H272F, bound FAM-$C_{14}H_{24}O_4$—Cl and/or TAMRA-$C_{14}H_{24}O_4$—Cl. In one embodiment, the substrate is R—$(CH_2)_2O(CH_2)_2O(CH_2)_2O(CH_2)_6Cl$, wherein R is a functional group. To prepare such a substrate, a functional group may be reacted with a molecule such as $NH(CH_2)_2O(CH_2)_2O(CH_2)_2O(CH_2)_6Cl$.

In one embodiment, substrates of the invention are permeable to the plasma membranes of cells. For instance, as described herein the plasma membranes of prokaryotic (*E. coli*) and eukaryotic (CHO—K1) cells were permeable to TAMRA-$C_{14}H_{24}O_4$—Cl and biotin-$C_{18}H_{32}O_4$—Cl and, these substrates were rapidly and efficiently loaded into and washed out of cells in the absence of a mutant hydrolase. In the presence of a mutant hydrolase, at least a portion of the substrate was prevented from being washed out of the cells. Thus, the bound portion of the substrate can serve as a marker or as a means to capture the mutant hydrolase or a fusion thereof.

The invention further provides methods for preparing a substrate for a hydrolase which substrate is modified to include one or more functional groups. Exemplary functional groups for use in the invention include, but are not limited to, an amino acid, protein, e.g., enzyme, antibody or other immunogenic protein, a radionuclide, a nucleic acid molecule, a drug, a lipid, biotin, avidin, streptavidin, a magnetic bead, a solid support, an electron opaque molecule, chromophore, MRI contrast agent, a dye, e.g., a xanthene dye, a calcium sensitive dye, e.g., 1-[2-amino-5-(2,7-dichloro-6-hydroxy-3-oxy-9-xanthenyl)-phenoxy]-2-(2'-amino-5'-methylphenoxy) ethane-N,N,N',N'-tetraacetic acid (Fluo-3), a sodium sensitive dye, e.g., 1,3-benzenedicarboxylic acid, 4,4'-[1,4,10,13-tetraoxa-7,16-diazacyclooctadecane-7,16-diylbis(5-methoxy-6,2-benzofurandiyl)]bis(PBFI), a NO sensitive dye, e.g., 4-amino-5-methylamino-2',7'-difluorescein, or other fluorophore. In one embodiment, the functional group is an immunogenic molecule, i.e., one which is bound by antibodies specific for that molecule. In one embodiment, the functional group is not a radionuclide.

The invention also includes a mutant hydrolase which comprises at least one amino acid substitution relative to a corresponding wild-type hydrolase, which substitution(s) renders the mutant hydrolase capable of forming a bond, e.g., a covalent bond with a substrate for the corresponding hydrolase, e.g., a substrate of the invention, which is more stable than the bond formed between a corresponding wild-type hydrolase and the substrate.

In one embodiment, the mutant hydrolase of the invention comprises at least one amino acid substitution in a residue which, in the wild-type hydrolase, is associated with activating a water molecule, e.g., a residue in a catalytic triad or an auxiliary residue, wherein the activated water molecule cleaves the bond formed between a catalytic residue in the wild-type hydrolase and a substrate of the hydrolase. As used herein, an "auxiliary residue" is a residue which alters the activity of another residue, e.g., it enhances the activity of a residue that activates a water molecule. Residues which activate water within the scope of the invention include but are not limited to those involved in acid-base catalysis, for instance, histidine, aspartic acid and glutamic acid. In another embodiment, the mutant hydrolase of the invention comprises at least one amino acid substitution in a residue which, in the wild-type hydrolase, forms an ester intermediate by nucleophilic attack of a substrate for the hydrolase.

For example, wild-type dehalogenase DhaA cleaves carbon-halogen bonds in halogenated hydrocarbons (HaloC$_3$-HaloC$_{10}$). The catalytic center of DhaA is a classic catalytic triad including a nucleophile, an acid and a histidine residue. The amino acids in the triad are located deep inside the catalytic pocket of DhaA (about 10 Å long and about 20 Å$^2$ in cross section). The halogen atom in a halogenated substrate for DhaA, for instance, the chlorine atom of a Cl-alkane substrate, is positioned in close proximity to the catalytic center of DhaA. DhaA binds the substrate, likely forms an ES complex, and an ester intermediate is formed by nucleophilic attack of the substrate by Asp106 (the numbering is based on the protein sequence of DhaA) of DhaA (FIG. 1). His272 of DhaA then activates water and the activated water hydrolyzes the intermediate, releasing product from the catalytic center. As described herein, mutant DhaAs, e.g., a DhaA.H272F mutant, which likely retains the 3-D structure based on a computer modeling study and basic physico-chemical characteristics of wild-type DhaA (DhaA.WT), were not capable of hydrolyzing one or more substrates of the wild-type enzyme, e.g., for Cl-alkanes, releasing the corresponding alcohol released by the wild-type enzyme. As further described herein, mutant serine beta-lactamases, e.g., a blaZ.E166D mutant, a blaZ.N170Q mutant and a blaZ.E166D:N170Q mutant, were not capable of hydrolyzing one or more substrates of a wild-type serine beta-lactamase.

Thus, in one embodiment of the invention, a mutant hydrolase is a mutant dehalogenase comprising at least one amino acid substitution in a residue which, in the wild-type dehalogenase, is associated with activating a water molecule, e.g., a residue in a catalytic triad or an auxiliary residue, wherein the activated water molecule cleaves the bond formed between a catalytic residue in the wild-type dehalogenase and a substrate of the dehalogenase. In one embodiment, at least one substitution is in a residue corresponding to residue 272 in DhaA from *Rhodococcus rhodochrous*. A "corresponding residue" is a residue which has the same activity (function) in one wild-type protein relative to a reference wild-type protein and optionally is in the same relative position when the primary sequences of the two proteins are aligned. For example, a residue which forms part of a catalytic triad and activates a water molecule in one enzyme may be residue 272 in that enzyme, which residue 272 corresponds to residue 73 in another enzyme, wherein residue 73 forms part of a catalytic triad and activates a water molecule. Thus, in one embodiment, a mutant dehalogenase of the invention has a phenylalanine residue at a position corresponding to residue 272 in DhaA from *Rhodococcus rhodochrous*. In another embodiment of the invention, a mutant hydrolase is a mutant dehalogenase comprising at least one amino acid substitution in a residue corresponding to residue 106 in DhaA from *Rhodococcus rhodochrous*. For example, a mutant dehalogenase of the invention has a cysteine or a glutamate residue at a position corresponding to residue 106 in DhaA from *Rhodococcus rhodochrous*. In a further embodiment, the mutant hydrolase is a mutant dehalogenase comprising at least two amino acid substitutions, one in a residue corresponding to residue 106 and one in a residue corresponding to residue 272 in DhaA from *Rhodococcus rhodochrous*. In yet a further embodiment, the mutant hydrolase is a mutant serine beta-lactamase comprising at least one amino acid substitution in a residue corresponding to residue 166 or residue 170 in a serine beta-lactamase of *Staphylococcus aureus* PC1.

The mutant hydrolase may be a fusion protein, e.g., a fusion protein expressed from a recombinant DNA which encodes the mutant hydrolase and at least one protein of interest or a fusion protein formed by chemical synthesis. For instance, the fusion protein may comprise a mutant hydrolase and an enzyme of interest, e.g., luciferase, RNasin or RNase, and/or a channel protein, a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, a transporter protein and/or a targeting sequence, e.g., a myristilation sequence, a mitochondrial localization sequence, or a nuclear localization sequence, that directs the mutant hydrolase, for example, a fusion protein, to a particular location. The protein of interest may be fused to the N-terminus or the C-terminus of the mutant hydrolase. In one embodiment, the fusion protein comprises a protein of interest at the N-terminus, and another protein, e.g., a different protein, at the C-terminus, of the mutant hydrolase. For example, the protein of interest may be a fluorescent protein or an antibody. Optionally, the proteins in the fusion are separated by a connector sequence, e.g., preferably one having at least 2 amino acid residues, such as one having 13 to 17 amino acid residues. The presence of a connector sequence in a fusion protein of the invention does not substantially alter the function of either protein in the fusion relative to the function of each individual protein. Thus, for a fusion of a mutant dehalogenase and *Renilla* luciferase, the presence of a connector sequence does not substantially alter the stability of the bond formed between the mutant dehalogenase and a substrate therefor or the activity of the luciferase. For any particular combination of proteins in a fusion, a wide variety of connector sequences may be employed. In one embodiment, the connector sequence is a sequence recognized by an enzyme, e.g., a cleavable sequence. For instance, the connector sequence may be one recognized by a caspase, e.g., DEVD (SEQ ID NO:64), or is a photocleavable sequence.

In one embodiment, the fusion protein may comprise a protein of interest at the N-terminus and, preferably, a different protein of interest at the C-terminus of the mutant hydrolase. As described herein, fusions of a mutant DhaA with GST (at the N-terminus), a Flag sequence (at the C-terminus) and *Renilla* luciferase (at the N-terminus or C-terminus) had no detectable effect on bond formation between the mutant DhaA and a substrate for wild-type DhaA which includes a functional group. Moreover, a fusion of a Flag sequence and DhaA.H272F could be attached to a solid support via a streptavidin-biotin-C$_{18}$H$_{32}$O$_4$-DhaA.H272F bridge (an SFlag-ELISA experiment). Further, a fusion of *Renilla* luciferase (R.Luc) and DhaA.H272F could be attached to Magnesil™ particles coated with a substrate for wild-type DhaA which includes a functional group. In addition, the attached fusion comprising R.Luc was shown to be enzymatically active.

Exemplary proteins of interest include, but are not limited to, an immunogenic protein, fluorescent protein, selectable marker protein, membrane protein, cytosolic protein, nuclear protein, structural protein, enzyme, e.g., RNase, enzyme substrate, receptor protein, transporter protein, transcription factor, channel protein, e.g., ion channel protein, phospho-protein, kinase, signaling protein, metabolic protein, mitochondrial protein, receptor associated protein, nucleic acid binding protein, extracellular matrix protein, secreted protein, receptor ligand, serum protein, or a protein with reactive cysteines.

The invention also includes compositions and kits comprising a substrate for a hydrolase which includes a linker, a substrate for a hydrolase which includes one or more functional groups and optionally a linker, a linker which includes one or more functional groups, a substrate for a hydrolase which lacks one or more functional groups and optionally includes a linker, a linker, or a mutant hydrolase, or any combination thereof. For example, the invention includes a solid support comprising a substrate of the invention, a kit comprising a substrate of the invention, a kit comprising a vector encoding a dehalogenase of the invention, or a kit comprising a vector encoding a serine beta-lactamase of the invention.

Also provided is an isolated nucleic acid molecule (polynucleotide) comprising a nucleic acid sequence encoding a hydrolase. In one embodiment, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. In one embodiment, the polynucleotide includes a nucleic acid sequence encoding a dehalogenase, which nucleic acid sequence is optimized for expression in a selected host cell. In one embodiment, the optimized polynucleotide no longer hybridizes to the corresponding non-optimized sequence, e.g., does not hybridize to the non-optimized sequence under medium or high stringency conditions. In another embodiment, the polynucleotide has less than 90%, e.g., less than 80%, nucleic acid sequence identity to the corresponding non-optimized sequence and optionally encodes a polypeptide having at least 80%, e.g., at least 85%, 90% or more, amino acid sequence identity with the polypeptide encoded by the non-optimized sequence. Constructs, e.g., expression cassettes, and vectors comprising the isolated nucleic acid molecule, as well as kits comprising the isolated nucleic acid molecule, construct or vector are also provided.

Further provided is a method of expressing a mutant hydrolase of the invention. The method comprises introducing to a host cell a recombinant nucleic acid molecule encoding a mutant hydrolase of the invention so as to express the mutant hydrolase. In one embodiment, the mutant hydrolase may be isolated from the cell. The mutant hydrolase may be expressed transiently or stably, constitutively or under tissue-specific or drug-regulated promoters, and the like. Also provided is an isolated host cell comprising a recombinant nucleic acid molecule encoding a mutant hydrolase of the invention.

In one embodiment, the invention provides a method to detect or determine the presence or amount of a mutant hydrolase. The method includes contacting a mutant hydrolase with a hydrolase substrate which comprises one or more functional groups. The mutant hydrolase comprises at least one amino acid substitution relative to a corresponding wild-type hydrolase, wherein the at least one amino acid substitution results in the mutant hydrolase forming a bond with the substrate which is more stable than the bond formed between the corresponding wild-type hydrolase and the substrate, and wherein the at least one amino acid substitution in the mutant hydrolase is a substitution at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate. The presence or amount of the functional group is detected or determined, thereby detecting or determining the presence or amount of the mutant hydrolase. In one embodiment, the mutant hydrolase is in or on the surface of a cell. In another embodiment, the mutant hydrolase is in a cell lysate.

Also provided are methods of using a mutant hydrolase and a substrate for a corresponding hydrolase which includes one or more functional groups, e.g., to isolate a molecule or to detect or determine the presence or amount of, location, e.g., intracellular, subcellular or extracellular location, or movement of certain molecules in cells. In one embodiment, a method to isolate a molecule of interest in a sample is provided. The method includes contacting a sample with a fusion protein comprising a mutant hydrolase and a protein which binds a molecule of interest with a hydrolase substrate which comprises one or more functional groups. The mutant hydrolase comprises at least one amino acid substitution relative to a corresponding wild-type hydrolase, wherein the at least one amino acid substitution results in the mutant hydrolase forming a bond with the substrate which is more stable than the bond formed between the corresponding wild-type hydrolase and the substrate, and wherein the at least one amino acid substitution in the mutant hydrolase is a substitution at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate. In one embodiment, at least one functional group is a solid support or a molecule which binds to a solid support. In one embodiment, the sample contains intact cells while in another embodiment, the sample is a cell lysate or subcellular fraction. Then the molecule of interest is isolated.

For example, the invention includes method to isolate a protein of interest. The method includes contacting a fusion protein comprising a mutant hydrolase and a protein of interest with a hydrolase substrate which comprises at least one functional group. The mutant hydrolase comprises at least one amino acid substitution relative to a corresponding wild-type hydrolase, wherein the at least one amino acid substitution results in the mutant hydrolase forming a bond with the substrate which is more stable than the bond formed between the wild-type hydrolase and the substrate, and wherein the at least one amino acid substitution in the mutant hydrolase is a substitution at an amino acid residue in the wild-type hydrolase that is associated with activating a water molecule which cleaves a bond formed between the wild-type hydrolase and the substrate or at an amino acid residue in the wild-type hydrolase that forms an ester intermediate with the substrate. In one embodiment, at least one functional group is a solid support or a molecule which binds to a solid support. Then the protein of interest is isolated.

In another embodiment, the invention includes a method to identify an agent that alters the interaction of a protein of interest with a molecule suspected of interacting with the protein of interest. The method includes contacting at least one agent with the molecule suspected of interacting with the protein of interest, a fusion protein comprising mutant hydrolase and the protein of interest, and a hydrolase substrate which comprises one or more functional groups. The mutant hydrolase comprises at least one amino acid substitution relative to a corresponding wild-type hydrolase, wherein the at least one amino acid substitution results in the mutant hydrolase forming a bond with the substrate which is more stable than the bond formed between the corresponding wild-type hydrolase and the substrate, and wherein the at least one amino acid substitution in the mutant hydrolase is a substitution at an amino acid residue in the corresponding wild-type hydrolase that is associated with activating a water molecule which cleaves a bond formed between the corresponding wild-type hydrolase and the substrate at an amino acid residue in the wild-type hydrolase that forms an ester intermediate with the substrate. In one embodiment at least one functional group is a solid support or a molecule which binds to a solid support. Then it is determined whether the agent alters the interaction between the protein of interest and the molecule suspected of interacting with the protein of interest.

Moreover, a substrate of the invention bound to a solid support or a mutant hydrolase bound to a solid support may be used to generate protein arrays, cell arrays, vesicle/organelle arrays and cell membrane arrays.

The invention thus provides methods to monitor the expression, location and/or movement (trafficking) of proteins in a cell as well as to monitor changes in microenvironments within a cell. In one embodiment, the use of a mutant hydrolase and a substrate of the invention permits functional analysis of proteins, e.g., ion channels. In another embodiment, the use of two pairs of a mutant hydrolase/substrate permits multiplexing, simultaneous detection, and FRET- or BRET-based assays. For example, mutant dehalogenases with substitutions at different residues of a catalytic triad may each preferentially bind certain substrates of the invention but not others or a mutant dehalogenase and a mutant beta-lactamase may be employed with their respective substrates, thus permitting multiplexing. Other applications include capturing the stable complex which results from contacting the mutant hydrolase with a corresponding substrate of the invention, on a solid substrate for analytical or industrial purposes (e.g., to study kinetic parameters of the tethered enzyme, to generate enzyme chains/arrays, to metabolize industrial components, and the like), to detect protein-protein interactions, to determine the effect of different compounds/drugs on an interaction between a fusion protein comprising a protein of interest and a mutant hydrolase with other molecules, to isolate or purify molecules which bind to a protein of interest fused to the mutant hydrolase, or to isolate or purify cells, organelles or fragments thereof. For example, a protein of interest may be fused to a mutant hydrolase and then linked to a solid support via the specific interaction of a functional group which is a ligand for an acceptor group and is present in a substrate of the invention, with an acceptor group present on the solid support. Such a substrate may be contacted with the fusion protein prior to contact with the solid support, contacted with the solid support prior to contact with the fusion protein, or simultaneously contacted with the fusion protein and the solid support. Such a system permits the resulting complex to be employed to detect or isolate molecules which bind to the protein of interest. The binding molecule may be a protein, e.g., a fusion of the binding protein and a functional group, e.g., GFP, luciferase, an antibody, e.g., one conjugated to horseradish peroxidase (HRP), alkaline phosphatase (AP) or a fluorophore.

To isolate, sort or purify cells, the mutant hydrolase may be expressed on the outside surface of cells (e.g., via a fusion with a plasma membrane protein). To isolate, purify or separate organelles, the mutant hydrolase is expressed on the cytosolic surface of the organelle of interest. In another embodiment, to create an optimal platform for growing different cells, the mutant hydrolase is fused with an extracellular matrix component or an outer membrane protein and tethered to a three-dimensional cell culture or a platform for tissue engineering. As an example, primary neurons or embryonic stem cells may be grown on the platform to form a feeder layer.

Other applications include detecting or labeling cells. Thus, the use of a mutant hydrolase and a corresponding substrate of the invention permits the detection of cells, for instance, to detect cell migration in vitro or in vivo after implantation or injection into animals (e.g., angiogenesis/chemotaxis assays, migration of implanted neurons, normal, malignant, or recombinantly modified cells implanted/injected into animals, and the like), and live cell imaging followed by immunocytochemistry. In another embodiment, the invention provides a method to label newly synthesized proteins. For example, cells comprising a vector which expresses a mutant hydrolase of the invention or a fusion thereof, are contacted with a substrate for the hydrolase which lacks a functional group. Cells are then contacted with an agent, e.g., an inducer of gene expression, and a substrate for the hydrolase which contains one or more functional groups. The presence, amount or location of the mutant hydrolase or fusion thereof is then detected or determined. The presence, amount or location of the mutant hydrolase or fusion thereof is due to newly synthesized mutant hydrolase or a fusion thereof. Alternatively, cells comprising a vector which expresses a mutant hydrolase of the invention or a fusion thereof, are contacted with a substrate for the hydrolase having a functional group, e.g., a green fluorophore, then contacted with an agent and a substrate having a different functional group, e.g., a red fluorophore. In one embodiment, the mutant hydrolase is fused to a membrane localization signal and so can be employed to monitor events in or near the membrane.

Accordingly, the invention provides a method to label a cell. The method includes contacting a cell comprising a mutant hydrolase with a hydrolase substrate which comprises one or more functional groups. The mutant hydrolase comprises at least one amino acid substitution relative to a corresponding wild-type hydrolase, wherein the at least one amino acid substitution results in the mutant hydrolase forming a bond with the substrate which is more stable than the bond formed between the corresponding wild-type hydrolase and the substrate, and wherein the at least one amino acid substitution in the mutant hydrolase is a substitution at an amino acid residue in the corresponding wild-type hydrolase that is associated with activating a water molecule which cleaves a bond formed between the corresponding wild-type hydrolase and the substrate or at an amino acid residue in the corresponding wild-type hydrolase that forms an ester intermediate with the substrate. Then the presence or amount of the functional group is detected or determined.

Cells expressing selectable marker proteins, such as ones encoding resistance to neomycin, hygromycin, or puromycin, are used to stably transform cells with foreign DNA. It may be desirable to observe which cells contain selectable marker proteins as well as fluorescently labeled molecules. For instance, it may be preferable to label the selectable marker protein with a fluorescent molecule that is added exogenously to living cells. By this method, the selectable marker protein becomes visible when only when needed by addition of the fluorophore, and the fluorescence will subsequently be lost when selectable marker proteins are naturally regenerated through cellular metabolism. Thus, in one embodiment, the invention provides a method for labeling a cell which expresses a selectable marker protein. The method includes providing a cell comprising an expression cassette comprising a nucleic acid sequence encoding a fusion protein. The fusion protein comprises a selectable marker protein, e.g., one which confers resistance to at least one antibiotic, and a second protein that is capable of stably and optionally irreversibly binding a substrate or a portion thereof which includes an optically detectable molecule. For instance, the protein may be an alkyl transferase which irreversibly transfers an alkyl group and an optically detectable molecule from a substrate to itself, thereby labeling the alkyl transferase, e.g., an alkyl transferase such as $O^6$-alkylguanine DNA alkyltransferase. Exemplary proteins useful in this embodiment of the invention include, but are not limited to, alkyl transferases, peptidyl glycine-alpha-amidating monoxygenases, type I topoisomerases, hydrolases, e.g., serine and epoxide hydrolases as well as the mutant hydrolases described herein, aminotransferases, cytochrome P450 monooxygenases, acetyl transferases, decarboxylases, oxidases, e.g., monoamine oxidases, reductases, e.g., ribonucleotide reductase, synthetases, e.g., cyclic ADP ribose synthetase or thymidylate synthetase, dehydrogenases, e.g., aldehyde dehydrogenase, synthases, e.g., nitric oxide synthase (NOS), lactamases, cystathionine gamma-lyases, peptidases, e.g., carboxypeptidase A, aromatase, proteases, e.g., serine protease, xylanases, glucosidases, mannosidases, and demethylases and other proteins, including wild-type proteins, which form an irreversible or otherwise stable bond with one or more substrates, e.g., enzymes which are capable of mechanism-based inactivation. Thus, in this embodiment, a stable bond, i.e., one which is formed between a substrate and a wild-type or mutant enzyme, has a $t_{1/2}$ of at least 30 minutes and preferably at least 4 hours, and up to at least 10 hours, and is resistant to disruption by washing, protein denaturants, and/or high temperatures, e.g., the bond is stable to boiling in SDS.

The cell which expresses the fusion protein is contacted with the substrate so as to label the cell. In one embodiment, the cell is fixed prior to contact with the substrate. In another embodiment, the substrate and fixative are contacted with the cell at the same time. In yet another embodiment, the fixative is added to the cell after the cell is contacted with the substrate. In one embodiment, the fusion protein forms an ester bond with the substrate. In another embodiment, the fusion protein forms a thioester bond with the substrate. Also provided is a fusion gene encoding the fusion protein, and a cell which expresses the fusion protein.

When performing image analysis on a cell, it may be desirable to fix the cell with a preservative (fixative) such as paraformaldehyde, acetone or methanol which generally maintains most features of cellular structure. Such fixed cells are then often analyzed by adding fluorescent stains or fluorescently labeled antibodies to reveal specific structures within the cells. Another method to fluorescently label cells is to express a fluorescent protein, e.g., GFP, in cells prior to fixation. Unfortunately, the efficient fluorescence of these proteins is dependent on protein structure, which can be disrupted by preservatives, thus decreasing the efficiency of imaging in those cells.

Accordingly, the invention provides a method for labeling a cell with a functional group, e.g., fluorophore. The method includes providing a cell which expresses a mutant hydrolase of the invention or a fusion thereof, and contacting the cell with a hydrolase substrate which includes at least one functional group. In one embodiment, the cell is fixed prior to contact with the substrate. In another embodiment, the substrate and fixative are contacted with the cell at the same time. In yet another embodiment, the fixative is added to the cell after the cell is contacted with the substrate. Then the presence or location of the mutant hydrolase, or fusion thereof, in the cell is detected or determined. In one embodiment, the mutant hydrolase forms an ester bond with the substrate, while in another embodiment, the mutant hydrolase forms a thioester bond with the substrate.

The invention also provides processes and intermediates disclosed herein that are useful for preparing compounds, compositions, nucleic acids, proteins, or other materials of the invention.

BRIEF DESCRIPTION OF THE FIGURES

FIG. 14 shows SDS-PAGE analysis of two-fold serial dilutions of *E. coli* expressing either wild-type DhaA (DhaA.WT-Flag, lanes 1-4 of each panel) or mutant DhaA.H272F (DhaA.H272F-Flag, lanes 5-7 of each panel) treated with biotin-$C_{18}H_{32}O_4$—Cl (panel A) or TAMRA-$C_{12}H_{24}O_4$—Cl (panel B) in vivo. Arrows mark proteins with $M_r$ corresponding to $M_r$ of DhaA-Flag.

FIG. 15 shows the binding of TAMRA-$C_{12}H_{24}O_4$—Cl to eukaryotic cell proteins in vivo. Two-fold serial dilutions of proteins from CHO—K1 cells expressing either DhaA.WT-Flag (lanes 1-4) or DhaA.H272F-Flag (lanes 5-8) were treated with TAMRA-$C_{12}H_{24}O_4$—Cl. Arrows mark proteins with Mr corresponding to Mr of DhaA-Flag.

FIG. 16 illustrates the permeability of TAMRA-$C_{12}H_{24}O_4$—Cl to CHO—K1 cells. CHO—K1 cells (A, bright field image) were treated with TAMRA-$C_{12}H_{28}O_4$—Cl (25 µM, for 5 minutes at 37° C.) and quickly washed with PBS (panel B). Panel C shows the cells after the washing procedure.

FIG. 17 shows images of cells transfected with GFP-connector-DhaA.WT-Flag or GFP-connector-DhaA.H272F-Flag. CHO—K1 cells were transfected with DNA coding GFP-connector-DhaA.WT-Flag (panels A-C) or GFP-connector-DhaA.H272F-Flag (panels D-F) and treated with TAMRA-$C_{12}H_{28}O_4$—Cl. Panels A, D-bright field; panels B, E-GFP filter set; and panels C, F-TAMRA filter set.

FIG. 18 shows Western blot analysis of proteins from cells transfected with GFP-connector-DhaA.WT-Flag (lanes 1-4) or GFP-connector-DhaA.H272F-Flag (lanes 5-8). CHO—K1 cells were transfected with either GFP-connector-DhaA.WT-Flag or GFP-connector-DhaA.H272F-Flag and then treated with TAMRA-$C_{14}H_{24}O_4$—Cl (25 µM) for 0, 5, 15 or 60 minutes, washed with PBS (4×1.0 ml), and collected in SDS-sample buffer. The samples were resolved on SDS-PAGE, and analyzed on a fluoroimager. Lanes 1-4, GFP-connector-DhaA.WT-Flag treated for 0, 5, 15, or 60 minutes, respectively. Lanes 5-8, GFP-connector-DhaA.H272F-Flag treated for 0, 5, 15, 60 minutes, respectively. Arrows mark proteins with $M_r$ corresponding to $M_r$ of GFP-connector-DhaA.H272F-Flag.

FIG. 22 shows the binding of bocellin to fusions of GST and blaZ.E166D, blaZ.N170Q or blaZ.E166D:N170Q. Lane 1-dye/no blaZ; lane 2-blaZ.WT; lane 3-blaZ.E166D; lane 4-blaZ.N170Q; and lane 5-blaZ.E166D:N170Q.

FIG. 23 shows the binding of CCF2 to fusions of GST and blaZ.E166D, blaZ.N170Q or blaZ.E166D:N170Q. Lane 1-dye/no blaZ; lane 2-GST-blaZ.WT; lane 3-GST-blaZ.E166D; lane 4-GST-blaZ.N170Q; and lane 5-GST-blaZ.E166D:N170Q.

FIG. 24 provides fluorescence and DIC images of living CHO—K1 cells transfected with a construct encoding GFP-connector-DhaA.H272F-NLS3 and stained with TAMRA-$C_{14}H_{24}O_4$—Cl. TAMRA filter-top left; GFP filter-top right; "A" and "B" overlaid-bottom left; overlaid image "C" and DIC image of the cell-bottom right. NLS3=tandem repeat of a nuclear localization sequence from SV40 T antigen.

FIG. 25 shows fluorescence images of living CHO—K1 cells transfected with a construct encoding GFP-β-arresting (left) and a construct encoding DhaA.H272F-β-arrestin2 and stained with TAMRA-$C_{14}H_{24}O_4$ (right).

FIGS. 30 C-D illustrate analyses of hR.Luc-DhaA captured on SA coated beads. CHO—K1 cells transiently expressing hR.Luc-connector-DhaA.H272F-Flag were treated with or without biotin-$C_{18}H_{32}O_4$—Cl (25 µM, 0.1% DMSO, 60 minutes, 37° C.). Cells were lysed, and 10 µl of cell lysate was incubated with 5 µl of SA-coated beads (Pierce) for 60 minutes at room temperature. Unbound material was washed out, and hR.Luc activity determined using Promega's "*Renilla* Luciferase Assay System" (C) or captured hR.Luc analyzed by Western blot (D). C) Column 1, cells treated with biotin-$C_{18}H_{32}O_4$—Cl, and excess biotin-$C_{18}H_{32}O_4$—Cl washed out; column 2, untreated cells; and column 3, cells treated with biotin-$C_{18}H_{32}O_4$—Cl without washing out excess biotin-$C_{18}H_{32}O_4$—Cl. D) Cell lysate (lane 1), proteins which were not bound to beads (lane 2), and proteins which were bound to beads (lane 3) were resolved on SDS-PAGE, transferred to nitrocellulose membrane, and probed with anti-R.Luc antibody (Chemicon).

DETAILED DESCRIPTION OF THE INVENTION

Definitions

Figure 1:
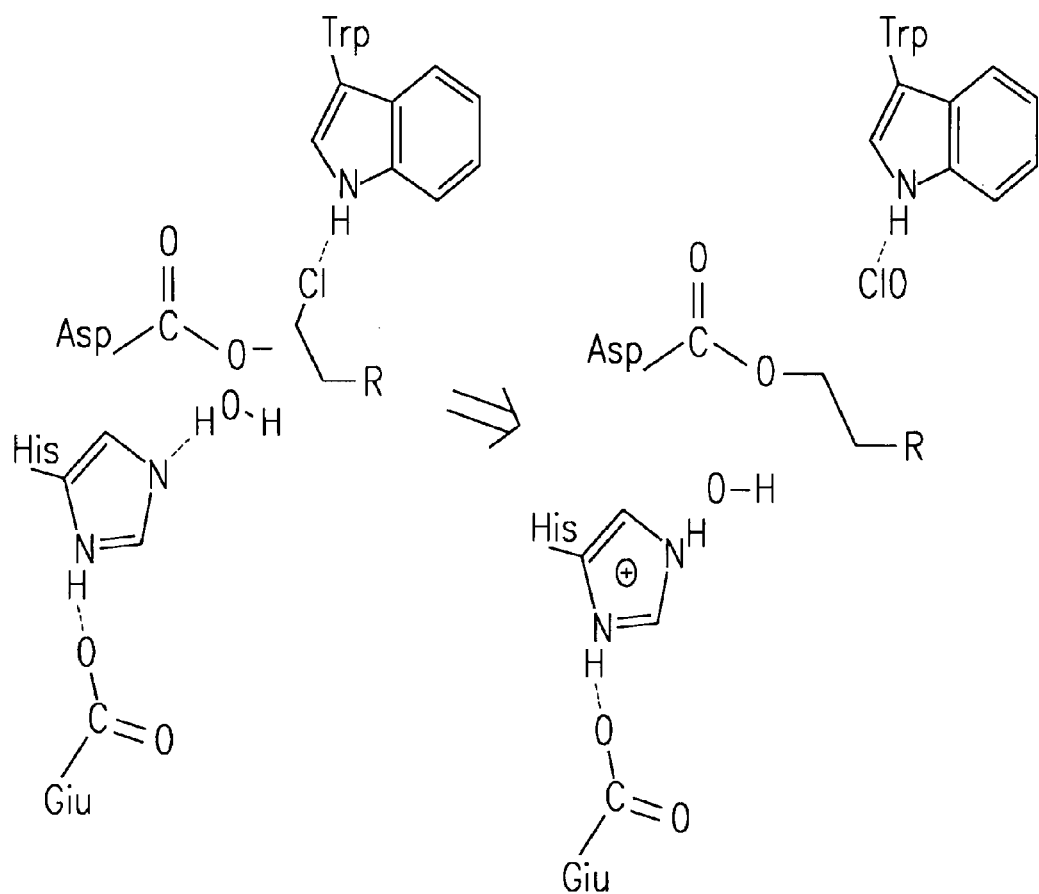
FIG. 1 is a schematic of a reaction in the catalytic triad of *Rhodococcus rhodochrous* dehalogenase with an alkylhalide substrate.

A "nucleophile" is a molecule which donates electrons.

A "selectable marker protein" encodes an enzymatic activity that confers to a cell the ability to grow in medium lacking what would otherwise be an essential nutrient (e.g., the TRP1 gene in yeast cells) or in a medium with an antibiotic or other drug, i.e., the expression of the gene encoding the selectable marker protein in a cell confers resistance to an antibiotic or drug to that cell relative to a corresponding cell without the gene. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers. Common selectable marker gene sequences include those for resistance to antibiotics such as ampicillin, tetracycline, kanamycin, puromycin, bleomycin, streptomycin, hygromycin, neomycin, Zeocin™, and the like. Selectable auxotrophic gene sequences include, for example, hisD, which allows growth in histidine free media in the presence of histidinol. Suitable selectable marker genes include a bleomycin-resistance gene, a metallothionein gene, a hygromycin B-phosphotransferase gene, the AUR1 gene, an adenosine deaminase gene, an aminoglycoside phosphotransferase gene, a dihydrofolate reductase gene, a thymidine kinase gene, a xanthine-guanine phosphoribosyltransferase gene, and the like.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides. A "polynucleotide", as used herein, is a nucleic acid containing a sequence that is greater than about 100 nucleotides in length. An "oligonucleotide" or "primer", as used herein, is a short polynucleotide or a portion of a polynucleotide. The term "oligonucleotide" or "oligo" as used herein is defined as a molecule comprised of 2 or more deoxyribonucleotides or ribonucleotides, preferably more than 3, and usually more than 10, but less than 250, preferably less than 200, deoxyribonucleotides or ribonucleotides. The oligonucleotide may be generated in any manner, including chemical synthesis, DNA replication, amplification, e.g., polymerase chain reaction (PCR), reverse transcription (RT), or a combination thereof. A "primer" is an oligonucleotide which is capable of acting as a point of initiation for nucleic acid synthesis when placed under conditions in which primer extension is initiated. A primer is selected to have on its 3' end a region that is substantially complementary to a specific sequence of the target (template). A primer must be sufficiently complementary to hybridize with a target for primer elongation to occur. A primer sequence need not reflect the exact sequence of the target. For example, a non-complementary nucleotide fragment may be attached to the 5' end of the primer, with the remainder of the primer sequence being substantially complementary to the target. Non-complementary bases or longer sequences can be interspersed into the primer provided that the primer sequence has sufficient complementarity with the sequence of the target to hybridize and thereby form a complex for synthesis of the extension product of the primer. Primers matching or complementary to a gene sequence may be used in amplification reactions, RT-PCR and the like.

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporation into a polypeptide chain, or a start or stop signal. The term "coding region" when used in reference to structural gene refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the terms "isolated and/or purified" refer to in vitro preparation, isolation and/or purification of a nucleic acid molecule, a polypeptide, peptide or protein, so that it is not associated with in vivo substances. Thus, the term "isolated" when used in relation to a nucleic acid, as in "isolated oligonucleotide" or "isolated polynucleotide" refers to a nucleic acid sequence that is identified and separated from at least one contaminant with which it is ordinarily associated in its source. An isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. Hence, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. The isolated nucleic acid molecule may be present in single-stranded or double-stranded form. When a nucleic acid molecule is to be utilized to express a protein, the nucleic acid contains at a minimum, the sense or coding strand (i.e., the nucleic acid may be single-stranded), but may contain both the sense and anti-sense strands (i.e., the nucleic acid may be double-stranded).

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA molecule" means a hybrid DNA sequence comprising at least two nucleotide sequences not normally found together in nature.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector", "expression vector" or "construct" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenylation signal and optionally an enhancer sequence.

A polynucleotide having a nucleotide sequence "encoding a peptide, protein or polypeptide" means a nucleic acid sequence comprising the coding region of a gene, or a fragment thereof which encodes a gene product having substantially the same activity as the corresponding full-length peptide, protein or polypeptide. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "transcription regulatory element" or "transcription regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene (Uetsuki et al., 1989; Kim et al., 1990; and Mizushima and Nagata, 1990) and the long terminal repeats of the Rous sarcoma virus (Gorman et al., 1982); and the human cytomegalovirus (Boshart et al., 1985).

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook et al., 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamH I/Bcl I restriction fragment and directs both termination and polyadenylation (Sambrook et al., 1989).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in situ" refers to cell culture. The term "in vivo" refers to the natural environment (e.g., an animal or a cell) and to processes or reaction that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of sources (e.g., the American Type Culture Collection, Rockland, Md.). The method of transformation or transfection and the choice of expression vehicle will depend on the host system selected. Transformation and transfection methods are described, e.g., in Sambrook et al., 1989. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

The term "gene" refers to a DNA sequence that comprises coding sequences and optionally control sequences necessary for the production of a polypeptide from the DNA sequence. The polypeptide can be encoded by a full-length coding sequence or by any portion of the coding sequence so long as the portion encodes a gene product with substantially the same activity as the full-length polypeptide.

Nucleic acids are known to contain different types of mutations. A "point" mutation refers to an alteration in the sequence of a nucleotide at a single base position from the wild-type sequence. Mutations may also refer to insertion or deletion of one or more bases, so that the nucleic acid sequence differs from a reference, e.g., a wild-type, sequence.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989; Nucleic Acid Hybridization, A Practical Approach, IRL Press, Washington D.C., 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4^-$ $H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" include conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

By "peptide", "protein" and "polypeptide" is meant any chain of amino acids, regardless of length or post-translational modification (e.g., glycosylation or phosphorylation). Unless otherwise specified, the terms are interchangeable. The nucleic acid molecules of the invention encode a variant (mutant) of a naturally-occurring (wild-type) protein or fragment thereof which has substantially the same activity as the full length mutant protein. Preferably, such a mutant protein has an amino acid sequence that is at least 85%, preferably 90%, and most preferably 95% or 99%, identical to the amino acid sequence of a corresponding wild-type protein.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide (1) is not associated with proteins found in nature, (2) is free of other proteins from the same source, e.g., free of human proteins, (3) is expressed by a cell from a different species, or (4) does not occur in nature. In contrast, non-isolated polypeptides (e.g., proteins and enzymes) are found in the state they exist in nature. The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The term "fusion polypeptide" as used herein refers to a chimeric protein containing a protein of interest (e.g., luciferase, an affinity tag or a targeting sequence) joined to a different protein, e.g., a mutant hydrolase.

As used herein, the term "antibody" refers to a protein having one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins, or as modifications in a variety of forms including, for example, $FabFc_2$, Fab, Fv, Fd, $(Fab')_2$, an Fv fragment containing only the light and heavy chain variable regions, a Fab or $(Fab)'_2$ fragment containing the variable regions and parts of the constant regions, a single-chain antibody, e.g., scFv, CDR-grafted antibodies and the like. The heavy and light chain of a Fv may be derived from the same antibody or different antibodies thereby producing a chimeric Fv region. The antibody may be of animal (especially mouse or rat) or human origin or may be chimeric or humanized. As used herein the term "antibody" includes these various forms.

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably transfected cell line capable of producing the protein or polypeptide encoded by the nucleic acid molecule. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "purified" or "to purify" means the result of any process that removes some of a contaminant from the component of interest, such as a protein or nucleic acid. The percent of a purified component is thereby increased in the sample.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide, or a precursor thereof, e.g., the pre- or prepro-form of the protein or polypeptide, is produced.

All amino acid residues identified herein are in the natural L-configuration. In keeping with standard polypeptide nomenclature, abbreviations for amino acid residues are as shown in the following Table of Correspondence.

TABLE OF CORRESPONDENCE

| 1-Letter | 3-Letter | AMINO ACID |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |

-continued

TABLE OF CORRESPONDENCE

| 1-Letter | 3-Letter | AMINO ACID |
| --- | --- | --- |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

As used herein, the term "poly-histidine tract" or (His tag) refers to a molecule comprising two to ten histidine residues, e.g., a poly-histidine tract of five to ten residues. A poly-histidine tract allows the affinity purification of a covalently linked molecule on an immobilized metal, e.g., nickel, zinc, cobalt or copper, chelate column or through an interaction with another molecule (e.g., an antibody reactive with the His tag).

As used herein, "pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a "substantially pure" composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

I. Mutant Hydrolases and Fusions Thereof

Mutant hydrolases within the scope of the invention include but are not limited to those prepared via recombinant techniques, e.g., site-directed mutagenesis or recursive mutagenesis, and comprise one or more amino acid substitutions which render the mutant hydrolase capable of forming a stable, e.g., covalent, bond with a substrate, such as a substrate modified to contain one or more functional groups, for a corresponding nonmutant (wild-type) hydrolase. Hydrolases within the scope of the invention include, but are not limited to, peptidases, esterases (e.g., cholesterol esterase), glycosidases (e.g., glucosamylase), phosphatases (e.g., alkaline phosphatase) and the like. For instance, hydrolases include, but are not limited to, enzymes acting on ester bonds such as carboxylic ester hydrolases, thiolester hydrolases, phosphoric monoester hydrolases, phosphoric diester hydrolases, triphosphoric monoester hydrolases, sulfuric ester hydrolases, diphosphoric monoester hydrolases, phosphoric triester hydrolases, exodeoxyribonucleases producing 5'-phosphomonoesters, exoribonucleases producing 5'-phosphomonoesters, exoribonucleases producing 3'-phosphomonoesters, exonucleases active with either ribo- or deoxyribonucleic acid, exonucleases active with either ribo- or deoxyribonucleic acid, endodeoxyribonucleases producing 5'-phosphomonoesters, endodeoxyribonucleases producing other than 5'-phosphomonoesters, site-specific endodeoxyribonucleases specific for altered bases, endoribonucleases producing 5'-phosphomonoesters, endoribonucleases producing other than 5'-phosphomonoesters, endoribonucleases active with either ribo- or deoxyribonucleic, endoribonucleases active with either ribo- or deoxyribonucleic glycosylases; glycosidases, e.g., enzymes hydrolyzing O- and S-glycosyl, and hydrolyzing N-glycosyl compounds; acting on ether bonds such as trialkylsulfonium hydrolases or ether hydrolases; enzymes acting on peptide bonds (peptide hydrolases) such as aminopeptidases, dipeptidases, dipeptidyl-peptidases and tripeptidyl-peptidases, peptidyl-dipeptidases, serine-type carboxypeptidases, metallocarboxypeptidases, cysteine-type carboxypeptidases, omega peptidases, serine endopeptidases, cysteine endopeptidases, aspartic endopeptidases, metalloendopeptidases, threonine endopeptidases, and endopeptidases of unknown catalytic mechanism; enzymes acting on carbon-nitrogen bonds, other than peptide bonds, such as those in linear amides, in cyclic amides, in linear amidines, in cyclic amidines, in nitriles, or other compounds; enzymes acting on acid anhydrides such as those in phosphorous-containing anhydrides and in sulfonyl-containing anhydrides; enzymes acting on acid anhydrides (catalyzing transmembrane movement); enzymes acting on acid anhydrides or involved in cellular and subcellular movement; enzymes acting on carbon-carbon bonds (e.g., in ketonic substances); enzymes acting on halide bonds (e.g., in C-halide compounds); enzymes acting on phosphorus-nitrogen bonds; enzymes acting on sulfur-nitrogen bonds; enzymes acting on carbon-phosphorus bonds; and enzymes acting on sulfur-sulfur bonds. Exemplary hydrolases acting on halide bonds include, but are not limited to, alkylhalidase, 2-haloacid dehalogenase, haloacetate dehalogenase, thyroxine deiodinase, haloalkane dehalogenase, 4-chlorobenzoate dehalogenase, 4-chlorobenzoyl-CoA dehalogenase, and atrazine chlorohydrolase. Exemplary hydrolases that act on carbon-nitrogen bonds in cyclic amides include, but are not limited to, barbiturase, dihydropyrimidinase, dihydroorotase, carboxymethylhydantoinase, allantoinase, β-lactamase, imidazolonepropionase, 5-oxoprolinase (ATP-hydrolysing), creatininase, L-lysine-lactamase, 6-aminohexanoate-cyclic-dimer hydrolase, 2,5-dioxopiperazine hydrolase, N-methylhydantoinase (ATP-hydrolysing), cyanuric acid amidohydrolase, maleimide hydrolase. "Beta-lactamase" as used herein includes Class A, Class C and Class D beta-lactamases as well as D-ala carboxypeptidase/transpeptidase, esterase EstB, penicillin binding protein 2X, penicillin binding protein 5, and D-amino peptidase. Preferably, the beta-lactamase is a serine beta-lactamase, e.g., one having a catalytic serine residue at a position corresponding to residue 70 in the serine beta-lactamase of *S. aureus* PC1, and a glutamic acid residue at a position corresponding to residue 166 in the serine beta-lactamase of *S. aureus* PC1, optionally having a lysine residue at a position corresponding to residue 73, and also optionally having a lysine residue at a position corresponding to residue 234, in the beta-lactamase of *S. aureus* PC1.

In one embodiment, the mutant hydrolase is a haloalkane dehalogenase, e.g., such as those found in Gram-negative (Keuning et al., 1985) and Gram-positive haloalkane-utilizing bacteria (Keuning et al., 1985; Yokota et al., 1987; Scholtz et al., 1987; Sallis et al., 1990). Haloalkane dehalogenases, including DhlA from *Xanthobacter autotrophicus* GJ10 (Janssen et al., 1988, 1989) and DhaA from *Rhodococcus rhodochrous*, are enzymes which catalyze hydrolytic dehalogenation of corresponding hydrocarbons. Halogenated aliphatic hydrocarbons subject to conversion include $C_2$-$C_{10}$ saturated aliphatic hydrocarbons which have one or more halogen groups attached, wherein at least two of the halogens are on adjacent carbon atoms. Such aliphatic hydrocarbons include volatile chlorinated aliphatic (VCA) hydrocarbons. VCA's include, for example, aliphatic hydrocarbons such as dichloroethane, 1,2-dichloro-propane, 1,2-dichlorobutane and 1,2,3-trichloropropane. The term "halogenated hydrocarbon" as used herein means a halogenated aliphatic hydrocarbon. As used herein the term "halogen" includes chlorine, bromine, iodine, fluorine, astatine and the like. A preferred halogen is chlorine.

As described herein, the invention includes a fusion protein comprising a mutant hydrolase and amino acid sequences for a protein of interest, e.g., sequences for a marker protein or affinity tag, e.g., luciferase, GFP, or a polyhistidine sequence, a nucleic acid binding protein, an extracellular matrix protein, a secreted protein, a receptor ligand, a serum protein, an immunogenic protein, a fluorescent protein, a protein with reactive cysteines, a receptor protein, e.g., NMDA receptor, a channel protein, e.g., a sodium-, potassium- or a calcium-sensitive channel protein including a HERG channel protein, or a transporter protein, e.g., EAAT1-4 glutamate transporter, as well as targeting signals, e.g., a plastid targeting signal, a nuclear localization signal or a myristilation sequence.

II. Optimized Hydrolase Sequences, and Vectors and Host Cells Encoding the Hydrolase A nucleic acid molecule comprising a nucleic acid sequence encoding a hydrolase or a fusion thereof is optionally optimized for expression in a particular host cell and also optionally operably linked to transcription regulatory sequences, e.g., one or more enhancers, a promoter, a transcription termination sequence or a combination thereof, to form an expression cassette.

In one embodiment, a nucleic acid sequence encoding a hydrolase or a fusion thereof is optimized by replacing codons in a wild-type or mutant hydrolase sequence with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. Thus, the optimized nucleic acid product has an improved level of expression due to improved codon usage frequency, and a reduced risk of inappropriate transcriptional behavior due to a reduced number of undesirable transcription regulatory sequences.

An isolated and optimized nucleic acid molecule of the invention may have a codon composition that differs from that of the corresponding wild-type nucleic acid sequence at more than 30%, 35%, 40% or more than 45%, e.g., 50%, 55%, 60% or more of the codons. Preferred codons for use in the invention are those which are employed more frequently than at least one other codon for the same amino acid in a particular organism and, more preferably, are also not low-usage codons in that organism and are not low-usage codons in the organism used to clone or screen for the expression of the nucleic acid molecule. Moreover, preferred codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In one embodiment of the invention, the codons that are different are those employed more frequently in a mammal, while in another embodiment the codons that are different are those employed more frequently in a plant. Preferred codons for different organisms are known to the art, e.g., see www.kazusa.or.jp./codon/. A particular type of mammal, e.g., a human, may have a different set of preferred codons than another type of mammal. Likewise, a particular type of plant may have a different set of preferred codons than another type of plant. In one embodiment of the invention, the majority of the codons that differ are ones that are preferred codons in a desired host cell. Preferred codons for organisms including mammals (e.g., humans) and plants are known to the art (e.g., Wada et al., 1990; Ausubel et al., 1997). For example, preferred human codons include, but are not limited to, CGC (Arg), CTG (Leu), TCT (Ser), AGC (Ser), ACC (Thr), CCA (Pro), CCT (Pro), GCC (Ala), GGC (Gly), GTG (Val), ATC (Ile), ATT (Ile), AAG (Lys), AAC (Asn), CAG (Gln), CAC (His), GAG (Glu), GAC (Asp), TAC (Tyr), TGC (Cys) and TTC (Phe) (Wada et al., 1990). Thus, in one embodiment, synthetic nucleic acid molecules of the invention have a codon composition which differs from a wild type nucleic acid sequence by having an increased number of the preferred human codons, e.g., CGC, CTG, TCT, AGC, ACC, CCA, CCT, GCC, GGC, GTG, ATC, ATT, AAG, AAC, CAG, CAC, GAG, GAC, TAC, TGC, TTC, or any combination thereof. For example, the nucleic acid molecule of the invention may have an increased number of CTG or TTG leucine-encoding codons, GTG or GTC valine-encoding codons, GGC or GGT glycine-encoding codons, ATC or ATT isoleucine-encoding codons, CCA or CCT proline-encoding codons, CGC or CGT arginine-encoding codons, AGC or TCT serine-encoding codons, ACC or ACT threonine-encoding codon, GCC or GCT alanine-encoding codons, or any combination thereof, relative to the wild-type nucleic acid sequence. In another embodiment, preferred C. elegans codons include, but are not limited, to UUC (Phe), UUU (Phe), CUU (Leu), UUG (Leu), AUU (Ile), GUU (Val), GUG (Val), UCA (Ser), UCU (Ser), CCA (Pro), ACA (Thr), ACU (Thr), GCU (Ala), GCA (Ala), UAU (Tyr), CAU (His), CAA (Gln), AAU (Asn), AAA (Lys), GAU (Asp), GAA (Glu), UGU (Cys), AGA (Arg), CGA (Arg), CGU (Arg), GGA (Gly), or any combination thereof. In yet another embodiment, preferred Drosophilia codons include, but are not limited to, UUC (Phe), CUG (Leu), CUC (Leu), AUC (Ile), AUU (Ile), GUG (Val), GUC (Val), AGC (Ser), UCC (Ser), CCC (Pro), CCG (Pro), ACC (Thr), ACG (Thr), GCC (Ala), GCU (Ala), UAC (Tyr), CAC (His), CAG (Gln), AAC (Asn), AAG (Lys), GAU (Asp), GAG (Glu), UGC (Cys), CGC (Arg), GGC (Gly), GGA (gly), or any combination thereof. Preferred yeast codons include but are not limited to UUU (Phe), UUG (Leu), UUA (Leu), CCU (Leu), AUU (Ile), GUU (Val), UCU (Ser), UCA (Ser), CCA (Pro), CCU (Pro), ACU (Thr), ACA (Thr), GCU (Ala), GCA (Ala), UAU (Tyr), UAC (Tyr), CAU (His), CAA (Gln), AAU (Asn), AAC (Asn), AAA (Lys), AAG (Lys), GAU (Asp), GAA (Glu), GAG (Glu), UGU (Cys), CGU (Trp), AGA (Arg), CGU (Arg), GGU (Gly), GGA (Gly), or any combination thereof. Similarly, nucleic acid molecules having an increased number of codons that are employed more frequently in plants, have a codon composition which differs from a wild-type or parent nucleic acid sequence by having an increased number of the plant codons including, but not limited to, CGC (Arg), CTT (Leu), TCT (Ser), TCC (Ser), ACC (Thr), CCA (Pro), CCT (Pro), GCT (Ser), GGA (Gly), GTG (Val), ATC (Ile), ATT (Ile), AAG (Lys), AAC (Asn), CAA (Gln), CAC (His), GAG (Glu), GAC (Asp), TAC (Tyr), TGC (Cys), TTC (Phe), or any combination thereof (Murray et al., 1989). Preferred codons may differ for different types of plants (Wada et al., 1990).

In one embodiment, an optimized nucleic acid sequence encoding a hydrolase or fusion thereof has less than 100%, e.g., less than 90% or less than 80%, nucleic acid sequence identity relative to a non-optimized nucleic acid sequence encoding a corresponding hydrolase or fusion thereof. For instance, an optimized nucleic acid sequence encoding DhaA has less than about 80% nucleic acid sequence identity relative to non-optimized (wild-type) nucleic acid sequence encoding a corresponding DhaA, and the DhaA encoded by the optimized nucleic acid sequence optionally has at least 85% amino acid sequence identity to a corresponding wild-type DhaA. In one embodiment, the activity of a DhaA encoded by the optimized nucleic acid sequence is at least 10%, e.g., 50% or more, of the activity of a DhaA encoded by the non-optimized sequence, e.g., a mutant DhaA encoded by the optimized nucleic acid sequence binds a substrate with substantially the same efficiency, i.e., at least 50%, 80%, 100% or more, as the mutant DhaA encoded by the non-optimized nucleic acid sequence binds the same substrate.

The nucleic acid molecule or expression cassette may be introduced to a vector, e.g., a plasmid or viral vector, which optionally includes a selectable marker gene, and the vector introduced to a cell of interest, for example, a prokaryotic cell such as E. coli, Streptomyces spp., Bacillus spp., Staphylococcus spp. and the like, as well as eukaryotic cells including a plant (dicot or monocot), fungus, yeast, e.g., Pichia, Saccharomyces or Schizosaccharomyces, or mammalian cell. Preferred mammalian cells include bovine, caprine, ovine, canine, feline, non-human primate, e.g., simian, and human cells. Preferred mammalian cell lines include, but are not limited to, CHO, COS, 293, Hela, CV-1, SH-SY5Y (human neuroblastoma cells), HEK293, and NIH3T3 cells.

The expression of the encoded mutant hydrolase may be controlled by any promoter capable of expression in prokaryotic cells or eukaryotic cells. Preferred prokaryotic promoters include, but are not limited to, SP6, T7, T5, tac, bla, trp, gal, lac or maltose promoters. Preferred eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Preferred vectors for bacterial expression include pGEX-5X-3, and for eukaryotic expression include pCIneo-CMV.

The nucleic acid molecule, expression cassette and/or vector of the invention may be introduced to a cell by any method including, but not limited to, calcium-mediated transformation, electroporation, microinjection, lipofection, particle bombardment and the like.

III. Functional Groups

Functional groups useful in the substrates and methods of the invention are molecules that are detectable or capable of detection. A functional group within the scope of the invention is capable of being covalently linked to one reactive substituent of a bifunctional linker or a substrate for a hydrolase, and, as part of a substrate of the invention, has substantially the same activity as a functional group which is not linked to a substrate found in nature and is capable of forming a stable complex with a mutant hydrolase. Functional groups thus have one or more properties that facilitate detection, and optionally the isolation, of stable complexes between a substrate having that functional group and a mutant hydrolase. For instance, functional groups include those with a characteristic electromagnetic spectral property such as emission or absorbance, magnetism, electron spin resonance, electrical capacitance, dielectric constant or electrical conductivity as well as functional groups which are ferromagnetic, paramagnetic, diamagnetic, luminescent, electrochemiluminescent, fluorescent, phosphorescent, chromatic, antigenic, or have a distinctive mass. A functional group includes, but is not limited to, a nucleic acid molecule, i.e., DNA or RNA, e.g., an oligonucleotide or nucleotide, a protein, e.g., a luminescent protein, a peptide, for instance, an epitope recognized by a ligand, e.g., biotin or streptavidin, a hapten, an amino acid, a lipid, a lipid bilayer, a solid support, a fluorophore, a chromophore, a reporter molecule, a radionuclide, an electron opaque molecule, a MRI contrast agent, e.g., manganese, gadolinium (III) or iron-oxide particles, and the like. Methods to detect a particular functional group are known to the art. For example, a nucleic acid molecule can be detected by hybridization, amplification, binding to a nucleic acid binding protein specific for the nucleic acid molecule, enzymatic assays (e.g., if the nucleic acid molecule is a ribozyme), or, if the nucleic acid molecule itself comprises a molecule which is detectable or capable of detection, for instance, a radiolabel or biotin, it can be detected by an assay suitable for that molecule.

Exemplary functional groups include haptens, e.g., molecules useful to enhance immunogenicity such as keyhole limpet hemacyanin (KLH), cleavable labels, for instance, photocleavable biotin, and fluorescent labels, e.g., N-hydroxysuccinimide (NHS) modified coumarin and succinimide or sulfonosuccinimide modified BODIPY (which can be detected by UV and/or visible excited fluorescence detection), rhodamine, e.g., R110, rhodols, CRG6, Texas Methyl Red (TAMRA), Rox5, FAM, or fluoroscein, coumarin derivatives, e.g., 7 aminocoumarin, and 7-hydroxycoumarin, 2-amino-4-methoxynapthalene, 1-hydroxypyrene, resorufin, phenalenones or benzphenalenones (U.S. Pat. No. 4,812,409), acridinones (U.S. Pat. No. 4,810,636), anthracenes, and derivatives of α- and β-napthol, fluorinated xanthene derivatives including fluorinated fluoresceins and rhodols (e.g., U.S. Pat. No. 6,162,931), and bioluminescent molecules, e.g., luciferase or GFP. A fluorescent (or bioluminescent) functional group linked to a mutant hydrolase by virtue of being linked to a substrate for a corresponding wild-type hydrolase, may be used to sense changes in a system, like phosphorylation, in real time. Moreover, a fluorescent molecule, such as a chemosensor of metal ions, e.g., a 9-carbonylanthracene modified glycyl-histidyl-lysine (GHK) for $Cu^{2+}$, in a substrate of the invention may be employed to label proteins which bind the substrate. A bioluminescent or fluorescent functional group such as BODIPY, rhodamine green, GFP, or infrared dyes, also finds use as a functional group and may, for instance, be employed in interaction studies, e.g., using BRET, FRET, LRET or electrophoresis.

Another class of functional group is a molecule that selectively interacts with molecules containing acceptor groups (an "affinity" molecule). Thus, a substrate for a hydrolase which includes an affinity molecule can facilitate the separation of complexes having such a substrate and a mutant hydrolase, because of the selective interaction of the affinity molecule with another molecule, e.g., an acceptor molecule, that may be biological or non-biological in origin. For example, the specific molecule with which the affinity molecule interacts (referred to as the acceptor molecule) could be a small organic molecule, a chemical group such as a sulfhydryl group (—SH) or a large biomolecule such as an antibody or other naturally occurring ligand for the affinity molecule. The binding is normally chemical in nature and may involve the formation of covalent or non-covalent bonds or interactions such as ionic or hydrogen bonding. The acceptor molecule might be free in solution or itself bound to a solid or semi-solid surface, a polymer matrix, or reside on the surface of a solid or semi-solid substrate. The interaction may also be triggered by an external agent such as light, temperature, pressure or the addition of a chemical or biological molecule that acts as a catalyst. The detection and/or separation of the complex from the reaction mixture occurs because of the interaction, normally a type of binding, between the affinity molecule and the acceptor molecule.

Examples of affinity molecules include molecules such as immunogenic molecules, e.g., epitopes of proteins, peptides, carbohydrates or lipids, i.e., any molecule which is useful to prepare antibodies specific for that molecule; biotin, avidin, streptavidin, and derivatives thereof; metal binding molecules; and fragments and combinations of these molecules. Exemplary affinity molecules include His5 (HHHHH) (SEQ ID NO:19), His X6 (HHHHHH) (SEQ ID NO:20), C-myc (EQKLISEEDL) (SEQ ID NO:21), Flag (DYKDDDDK) (SEQ ID NO:22), SteptTag (WSHPQFEK) (SEQ ID NO:23), HA Tag (YPYDVPDYA) (SEQ ID NO:24), thioredoxin, cellulose binding domain, chitin binding domain, S-peptide, T7 peptide, calmodulin binding peptide, C-end RNA tag, metal binding domains, metal binding reactive groups, amino acid reactive groups, inteins, biotin, streptavidin, and maltose binding protein. For example, a substrate for a hydrolase which includes biotin is contacted with a mutant hydrolase. The presence of the biotin in a complex between the mutant hydrolase and the substrate permits selective binding of the complex to avidin molecules, e.g., streptavidin molecules coated onto a surface, e.g., beads, microwells, nitrocellulose and the like. Suitable surfaces include resins for chromatographic separation, plastics such as tissue culture surfaces or binding plates, microtiter dishes and beads, ceramics and glasses, particles including magnetic particles, polymers and other matrices. The treated surface is washed with, for example, phosphate buffered saline (PBS), to remove molecules that lack biotin and the biotin-containing complexes isolated. In some case these materials may be part of biomolecular sensing devices such as optical fibers, chemfets, and plasmon detectors.

Another example of an affinity molecule is dansyllysine. Antibodies which interact with the dansyl ring are commercially available (Sigma Chemical; St. Louis, Mo.) or can be prepared using known protocols such as described in Antibodies: A Laboratory Manual (Harlow and Lane, 1988). For example, the anti-dansyl antibody is immobilized onto the packing material of a chromatographic column. This method, affinity column chromatography, accomplishes separation by causing the complex between a mutant hydrolase and a substrate of the invention to be retained on the column due to its interaction with the immobilized antibody, while other molecules pass through the column. The complex may then be released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.). Dansyllysine may conveniently be detected because of its fluorescent properties.

When employing an antibody as an acceptor molecule, separation can also be performed through other biochemical separation methods such as immunoprecipitation and immobilization of antibodies on filters or other surfaces such as beads, plates or resins. For example, complexes of a mutant hydrolase and a substrate of the invention may be isolated by coating magnetic beads with an affinity molecule-specific or a hydrolase-specific antibody. Beads are oftentimes separated from the mixture using magnetic fields.

Another class of functional molecules includes molecules detectable using electromagnetic radiation and includes but is not limited to xanthene fluorophores, dansyl fluorophores, coumarins and coumarin derivatives, fluorescent acridinium moieties, benzopyrene based fluorophores, as well as 7-nitrobenz-2-oxa-1,3-diazole, and 3-N-(7-nitrobenz-2-oxa-1,3-diazol-4-yl)-2,3-diamino-propionic acid. Preferably, the fluorescent molecule has a high quantum yield of fluorescence at a wavelength different from native amino acids and more preferably has high quantum yield of fluorescence that can be excited in the visible, or in both the UV and visible, portion of the spectrum. Upon excitation at a preselected wavelength, the molecule is detectable at low concentrations either visually or using conventional fluorescence detection methods. Electrochemiluminescent molecules such as ruthenium chelates and its derivatives or nitroxide amino acids and their derivatives are detectable at femtomolar ranges and below.

In addition to fluorescent molecules, a variety of molecules with physical properties based on the interaction and response of the molecule to electromagnetic fields and radiation can be used to detect complexes between a mutant hydrolase and a substrate of the invention. These properties include absorption in the UV, visible and infrared regions of the electromagnetic spectrum, presence of chromophores which are Raman active, and can be further enhanced by resonance Raman spectroscopy, electron spin resonance activity and nuclear magnetic resonances and molecular mass, e.g., via a mass spectrometer.

Methods to detect and/or isolate complexes having affinity molecules include chromatographic techniques including gel filtration, fast-pressure or high-pressure liquid chromatography, reverse-phase chromatography, affinity chromatography and ion exchange chromatography. Other methods of protein separation are also useful for detection and subsequent isolation of complexes between a mutant hydrolase and a substrate of the invention, for example, electrophoresis, isoelectric focusing and mass spectrometry.

IV. Linkers

The term "linker", which is also identified by the symbol refers to a group or groups that covalently attach one or more functional groups to a substrate which includes a reactive group or to a reactive group. A linker, as used herein, is not a single covalent bond. The structure of the linker is not crucial, provided it yields a substrate that can be bound by its target enzyme. In one embodiment, the linker can be a divalent group that separates a functional group (R) and the reactive group by about 5 angstroms to about 1000 angstroms, inclusive, in length. Other suitable linkers include linkers that separate R and the reactive group by about 5 angstroms to about 100 angstroms, as well as linkers that separate R and the substrate by about 5 angstroms to about 50 angstroms, by about 5 angstroms to about 25 angstroms, by about 5 angstroms to about 500 angstroms, or by about 30 angstroms to about 100 angstroms.

In one embodiment the linker is an amino acid.

In another embodiment, the linker is a peptide.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a non-peroxide —O—, —S— or —NH—.

In another embodiment, the linker is a divalent group of the formula —W—F—W— wherein F is $(C_1-C_{30})$alkyl, $(C_2-C_{30})$alkenyl, $(C_2-C_{30})$alkynyl, $(C_3-C_8)$cycloalkyl, or $(C_6-C_{10})$aryl, wherein W is —N(Q)C(=O)—, —C(=O)N(Q)-, —OC(=O)—, —C(=O)O—, —O—, —S—, —S(O)—, —S(O)$_2$—, —N(Q)-, —C(=O)—, or a direct bond; wherein each Q is independently H or $(C_1-C_6)$alkyl In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups.

In another embodiment, the linker is a divalent branched or unbranched carbon chain comprising from about 2 to about 30 carbon atoms, which chain optionally includes one or more (e.g., 1, 2, 3, or 4) double or triple bonds.

In another embodiment, the linker is a divalent branched or unbranched carbon chain comprising from about 2 to about 30 carbon atoms.

In another embodiment, the linker is a divalent branched or unbranched carbon chain comprising from about 2 to about 20 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups.

In another embodiment, the linker is a divalent branched or unbranched carbon chain comprising from about 2 to about 20 carbon atoms, which chain optionally includes one or more (e.g., 1, 2, 3, or 4) double or triple bonds.

In another embodiment, the linker is a divalent branched or unbranched carbon chain comprising from about 2 to about 20 carbon atoms.

In another embodiment, the linker is —(CH$_2$CH$_2$O)—$_{1-10}$.

In another embodiment, the linker is —C(=O)NH(CH$_2$)$_3$—;   —C(=O)NH(CH$_2$)$_5$C(=O)NH(CH$_2$)—;   —CH$_2$OC(=O)NH(CH$_2$)$_2$O(CH$_2$)$_2$O(CH$_2$)—;   —C(=O)NH(CH$_2$)$_2$O(CH$_2$)$_2$O(CH$_2$)$_3$—;   —CH$_2$OC(=O)NH(CH$_2$)$_2$O(CH$_2$)$_2$O(CH$_2$)$_3$—; —(CH$_2$)$_4$C(=O)NH(CH$_2$)$_2$O(CH$_2$)$_2$O(CH$_2$)$_3$—;   —C(=O)NH(CH$_2$)$_5$C(=O)NH(CH$_2$)$_2$O(CH$_2$)$_2$—O—(CH$_2$)$_3$—;

Specifically, $(C_1-C_{30})$alkyl can be methyl, ethyl, propyl, isopropyl, butyl, iso-butyl, sec-butyl, pentyl, 3-pentyl, hexyl, heptyl, octyl, nonyl, or decyl; $(C_3-C_8)$cycloalkyl can be cyclopropyl, cyclobutyl, cyclopentyl, or cyclohexyl; $(C_2-C_{33})$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, heptenyl, octenyl, nonenyl, or decenyl; $(C_2-C_{30})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, heptynyl, octynyl, nonynyl, or decynyl; and $(C_6-C_{10})$aryl can be phenyl, indenyl, or naphthyl The term "amino acid," when used with reference to a linker, comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes natural and unnatural amino acids bearing a conventional amino protecting group (e.g., acetyl or benzyloxycarbonyl), as well as natural and unnatural amino acids protected at the carboxy terminus (e.g. as a ($C_1$-$C_6$)alkyl, phenyl or benzyl ester or amide). Other suitable amino and carboxy protecting groups are known to those skilled in the art (see for example, Greene, *Protecting Groups In Organic Synthesis*; Wiley: New York, 1981, and references cited therein). An amino acid can be linked to another molecule through the carboxy terminus, the amino terminus, or through any other convenient point of attachment, such as, for example, through the sulfur of cysteine.

The term "peptide" when used with reference to a linker, describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to another molecule through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

In one embodiment, a substrate of the invention for a dehalogenase which has a linker has the formula (I):

R-linker-A-X    (I)

wherein R is one or more functional groups (such as a fluorophore, biotin, luminophore, or a fluorogenic or luminogenic molecule, or is a solid support, including microspheres, membranes, glass beads, and the like), wherein the linker is a multiatom straight or branched chain including C, N, S, or O, wherein A-X is a substrate for a dehalogenase, and wherein X is a halogen. In one embodiment, A-X is a haloaliphatic or haloaromatic substrate for a dehalogenase. In one embodiment, the linker is a divalent branched or unbranched carbon chain comprising from about 12 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a nonperoxide —O—, —S— or —NH—. In one embodiment, A is $CH_2CH_2$ or $CH_2CH_2CH_2$. In one embodiment, a linker in a substrate for a dehalogenase such as a *Rhodococcus* dehalogenase, is a multiatom straight or branched chain including C, N, S, or O, and preferably 11-30 atoms when the functional group R includes an aromatic ring system or is a solid support.

In another embodiment, a substrate of the invention for a dehalogenase which has a linker has formula (II):

R-linker-$CH_2$—$CH_2$—$CH_2$—X    (II)

where X is a halogen, preferably chloride. In one embodiment, R is one or more functional groups, such as a fluorophore, biotin, luminophore, or a fluorogenic or luminogenic molecule, or is a solid support, including microspheres, membranes, glass beads, and the like. When R is a radiolabel, or a small detectable atom such as a spectroscopically active isotope, the linker can be 0-30 atoms.

V. Syntheses for Exemplary Substrates

[2-(2-Hydroxy-ethoxy)-ethyl]-carbamic acid anthracen-9-ylmethyl ester. To a stirring slurry of 9-anthracenemethanol (10 g, 48 mmol) and 4-nitrophenyl chloroformate (13.6 g, 67.5 mmol) in 200 ml $CH_2Cl_2$ was added triethylamine (6.7 ml, 0.19 mol). The resulting gold colored solution was allowed to stir 16 hrs at room temperature. At this point, 2-(2-aminoethoxy)ethanol (14.4 ml, 0.144 mol) was added and stirring continued for another 24 hours. The $CH_2Cl_2$ reaction mixture was then washed with a 2% sodium hydroxide (w/w) solution until no p-nitrophenol was observed in the organic layer. The dichloromethane was dried with sodium sulfate, filtered, and evaporated under reduced pressure.

The crude product was further purified by column chromatography on silica gel 60, progressively eluting with 1% to 3% methanol in dichloromethane. 7.6 g (58% yield) of a yellow solid was isolated: $^1$H NMR (CDCl$_3$) δ 8.38 (s, H-10), 8.28 (d, H-1, 8), 7.94 (d, H-4, 5), 7.44 (m, H-2, 3, 6, 7), 6.06 (s, CH$_2$-anth), 5.47 (t, exchangeable, NH), 3.53 (bs, CH$_2$—OH) 3.33 (m, three —CH—). Mass spectrum, m/e Calcd for $C_{20}H_{22}NO_4^+$: 340.15. Found: 340.23. Calcd for $C_{20}H_{21}NNaO_4^+$: 340.15. Found: 340.23.

a compound of formula III

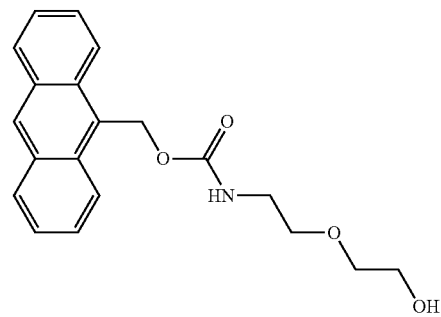

{2-[2-(6-Chloro-hexyloxy)-ethoxy]-ethyl}-carbamic acid anthracen-9-ylmethyl ester. A 100 ml round bottom flask was charged with [2-(2-Hydroxy-ethoxy)-ethyl]-carbamic acid anthracen-9-ylmethyl ester (1.12 g, 3 mmol) and fresh sodium hydride, 60% dispersion in mineral oil (360 mg, 9 mmol) under inert atmosphere. 20 ml anhydrous THF was added and the reaction allowed to stir for 30 minutes. The flask is then cooled to between −10 and −20° C. by means of an ice/NaCl bath. When the temperature is reached 1-chloro-6-Iodohexane (1 ml, 6 mmol) is added via syringe. The reaction is maintained at ice/NaCl temperature for 2 hours, then slowly allowed to warm to room temperature overnight. At this point silica gel 60 is co-absorbed onto the reaction mixture with loss of solvent under reduced pressure. Silica gel chromatography takes place initially with heptane as eluent, followed by 10%, 20%, and 25% ethyl acetate. A total of 0.57 g (41% yield) of product is isolated from appropriate fractions: $^1$H NMR (CDCl$_3$) δ 8.48 (s, H-10), 8.38 (d, H-1, 8), 8.01 (d, H-4, 5), 7.52 (dt, H-2, 3, 6, 7), 6.13 (s, CH$_2$-anth), 5.29 (bs, exchangeable, NH), 3.74 (m, 4H), 3.55-3.15 (m, 8H), 1.84 (m, 4H), 1.61 (m, 1H), 1.43 (m, 1H), 1.25 (m, 2H). Mass spectrum, m/e Calcd for $C_{26}H_{32}ClNO_4 \cdot H_2O$: 475.21 (100%), 476.22(29.6%). Found: 475.21, 476.52.

a compound of formula IV

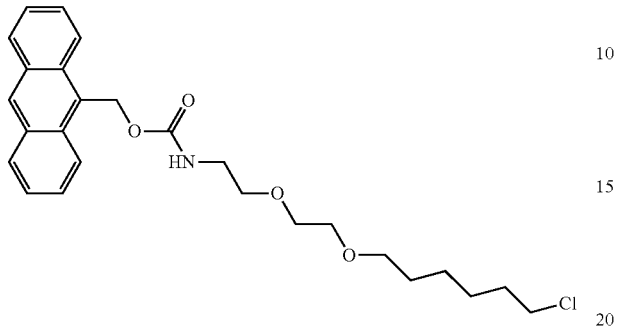

2-[2-(6-chlorohexyloxy)-ethoxy]-ethyl-ammonium trifluoro-acetate. To {2-[2-(6-Chloro-hexyloxy)-ethoxy]-ethyl}-carbamic acid anthracen-9-ylmethyl ester (0.56 g, 1.2 mmol) dissolved in 4 ml dichloromethane was added 2 drops of anisole. The reaction mixture is cooled by means of an ice/NaCl bath. After 10 minutes trifluoroacetic acid (2 ml) is added. The reaction mixture turns dark brown upon addition and is allowed to stir for 30 minutes. All volatiles are removed under reduced atmosphere. The residue is re-dissolved in $CH_2Cl_2$ and washed twice with water. The aqueous fractions are frozen and lyophilized overnight. An oily residue remains and is dissolved in anhydrous DMF to be used as a stock solution in further reactions. Mass spectrum, m/e Calcd for $C_{10}H_{23}ClNO_2^+$: 224.14(100%), 226.14(32%). Found: 224.2, 226.2.

a compound of formula V

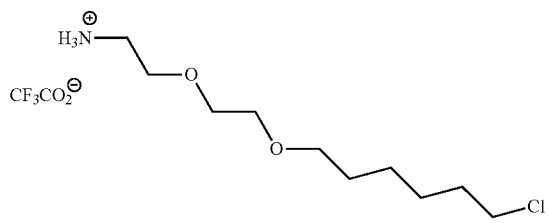

General methodology for reporter group conjugation to 2-[2-(6-chloro-hexyloxy)-ethoxy]-ethylamine. To one equivalent of the succinimidyl ester of the reporter group in DMF is added 3 equivalence of 2-[2-(6-chlorohexyloxy)-ethoxy]-ethyl-ammonium trifluoro-acetate stock solution, followed by diisopropylethylamine. The reaction is stirred from 8 to 16 hours at room temperature. Purification is accomplished by preparative scale HPLC or silica gel chromatography.

N-{2-[2-(6-Chlorohexyloxy)-ethoxy]-ethyl}-fluorescein-5-amide. The title compound was prepared using the above methodology. Purification was accomplished using preparative scale HPLC. Mass spectrum, m/e Calcd for $C_{31}H_{31}ClNO_8^-$: 580.17(100%), 581.18(32%). Found: 580.18, 581.31.

a compound of formula VI

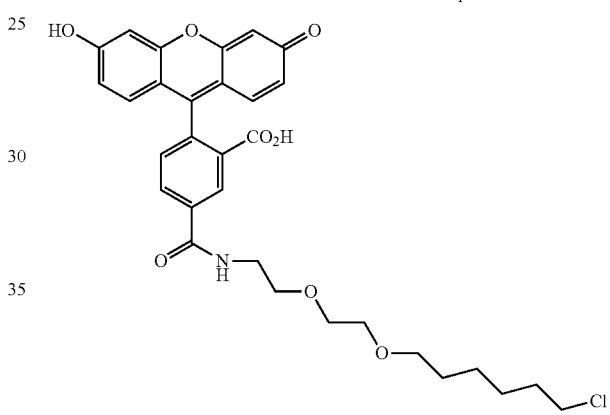

N-{2-[2-(6-Chlorohexyloxy)-ethoxy]ethyl}-biotin-amide. The title compound was prepared using the above methodology. Purification was accomplished using silica gel chromatography (2% to 5% methanol in dichloromethane). Mass spectrum, m/e Calcd for $C_{20}H_{37}ClN_3O_4S^+$: 450.22(100%), 452.22(32%). Found: 449.95, 451.89.

a compound of formula VII

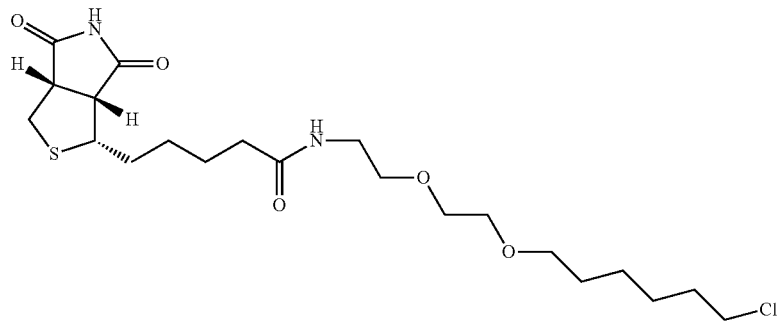

N-{2-[2-(6-Chlorohexyloxy)-ethoxy]-ethyl}-tetramethyl-rhodamine-5-(and -6)-amide. The title compound was prepared using the above methodology. Purification was accomplished using preparative scale HPLC. Separation of structural isomers was realized. Mass spectrum, m/e Calcd for $C_{35}H_{43}ClN_3O_6^+$: 636.28(100%), 637.29(39.8%), 638.28 (32.4%). Found: 636.14, 637.15, 638.14.

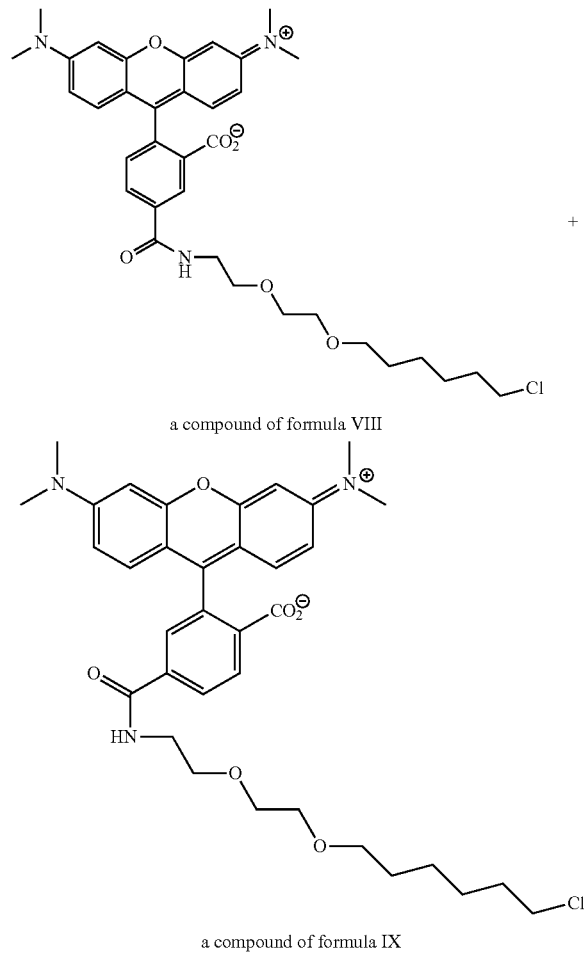

a compound of formula VIII a compound of formula IX

N-{2-[2-(6-Chlorohexyloxy)-ethoxy]ethyl}-rhodamine R110-5-(and -6)-amide. The title compound was prepared using the above methodology. Purification was accomplished using preparative scale HPLC. Separation of structural isomers was realized. Mass spectrum, m/e Calcd for $C_{31}H_{35}ClN_3O_6^+$: 580.2(100%), 581.2(35.6%), 582.2(32.4%). Found: 580.4, 581.4, 582.2.

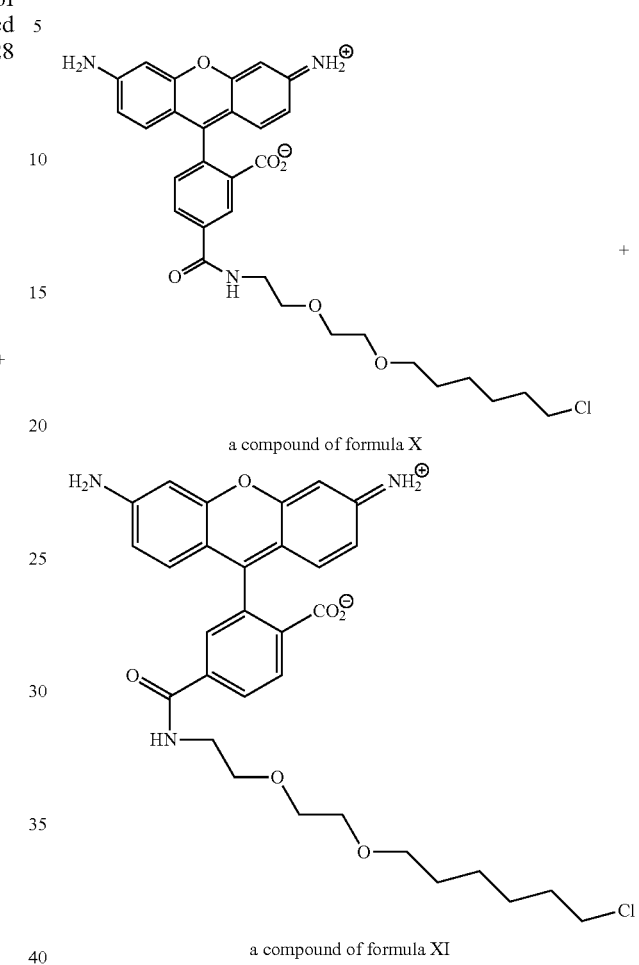

a compound of formula X a compound of formula XI 6-({4-[4,4difluoro-5-(thiophen-2-yl)-4-bora-3a-4-a-diaza-s-indacene-3-yl]phenoxy}-acetylamino)-hexanoic acid {2-[2-(6-chlorohexyloxy)-ethoxy]-ethyl}-amide. The title compound was prepared using the above methodology. Purification was accomplished using silica gel chromatography (3% to 5% methanol in dichloromethane). Mass spectrum, m/e Calcd for $C_{37}H_{47}BClF_2N_4O_5S^+$: 743.3(100%). Found: 743.4.

a compound of formula XII

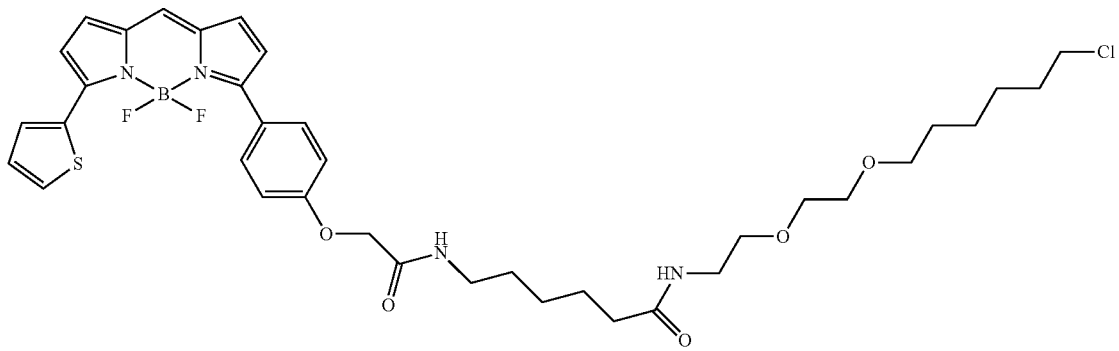

6-({4-[4-difluoro-5-(thiophen-2-yl)-4-bora-3a-4-a-diaza-s-indacene-3-yl]styryloxy}-acetylamino)-hexanoic acid {2-[2-(6-chlorohexyloxy)-ethoxy]-ethyl}-amide. The title compound was prepared using the above methodology. Purification was accomplished using silica gel chromatography (3% methanol in dichloromethane). Mass spectrum, m/e Calcd for $C_{39}H_{48}BClF_2N_4NaO_5S^+$: 791.3(100%). Found: 7.91.3.

2-tert-Butyl-4-{3-[1-(5-{2-[2-(6-chlorohexyloxy)-ethoxy]-ethylcarbamoyl}-pentyl)-3,3-dimethyl-5-sulfo-1,3-dihydro-indol-2-ylidene]-propenyl}-7-diethylamino-chromenylium chloride. The title compound was prepared using the above methodology. Purification was accomplished using preparative scale HPLC. Mass spectrum, m/e Calcd for $C_{46}H_{67}ClN_3O_7S^-$: 840.4(100%), 841.4(54.4%). Found: 840.5, 841.5.

a compound of formula XIII

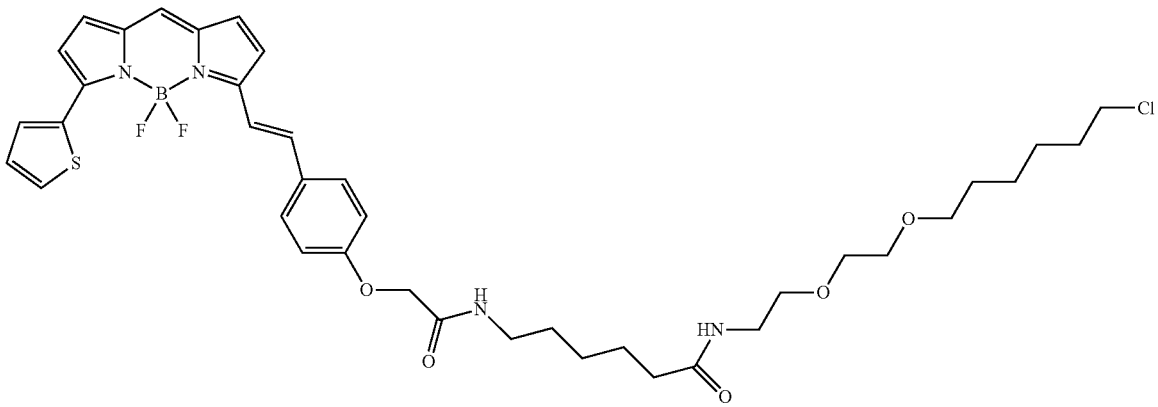

Triethylammonium 3-[5-[2-(4-tert-Butyl-7-diethylamino-chromen-2-ylidene)-ethylidene]-3-(5-{2-[2-(6-chlorohexyloxy)-ethoxy]-ethylcarbamoyl}-pentyl)-2,4,6-trioxo-tetrahydro-pyrimidin-1-yl]-propane-1-sulfonic acid anion. The title compound was prepared using the above methodology. Purification was accomplished using preparative scale HPLC. Mass spectrum, m/e Calcd for $C_{42}H_{62}ClN_4O_{10}S^-$: 849.4(100%), 850.4(48.8%), 851.4(36.4%). Found: 849.6, 850.5, 851.5.

a compound of formula XIV

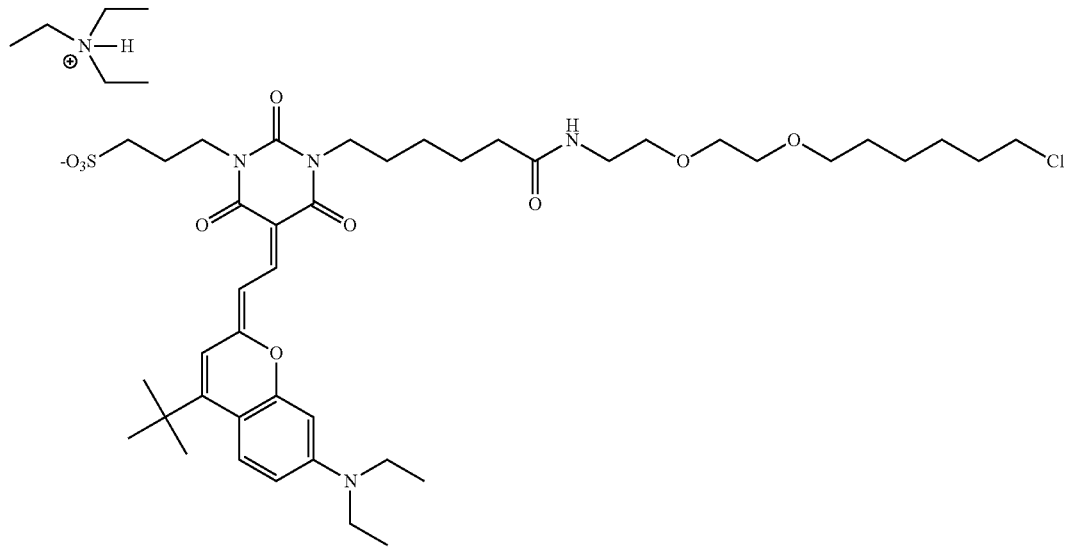

a compound of formula XV

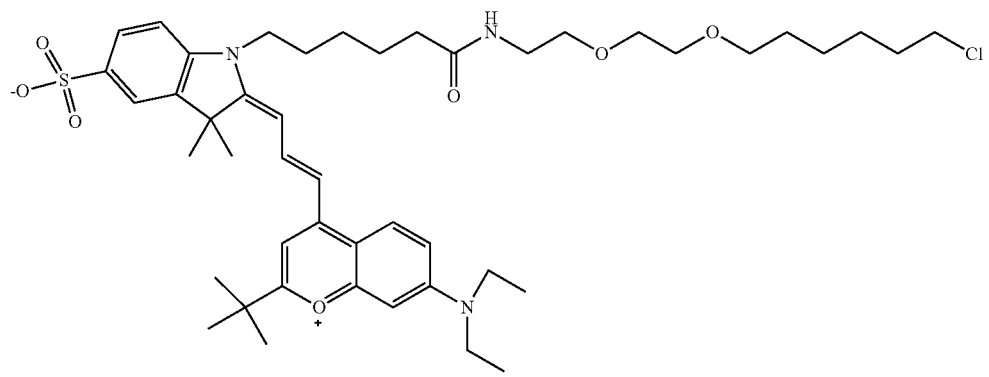

N-{2-[2-(6-Chlorohexyloxy)-ethoxy]-ethyl}-3-{4-[5-(4-dimethylamino-phenyl)-oxazol-2-yl]-benzenesulfonylamino}-propionamide. The title compound was prepared using the above methodology. Purification was accomplished using preparative scale HPLC. Mass spectrum, m/e Calcd for $C_{30}H_{40}ClN_4O_6S^-$: 619.2(100%), 620.2(35%). Found: 619.5, 620.7.

a compound of formula XVI

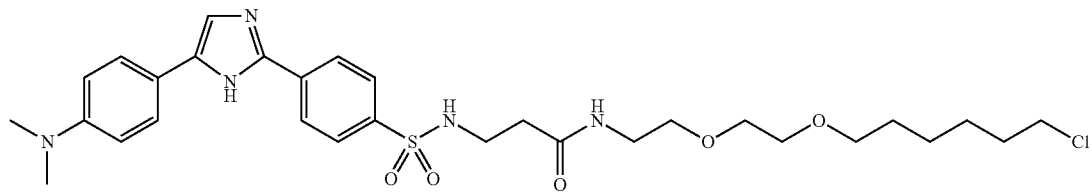

N-{2-[2-(6-Chlorohexyloxy)-ethoxy]-ethyl}-9'-chloroseminaphthofluorescein-5-(and -6)-amide. The title compound was prepared using the above methodology. Purification was accomplished using preparative scale HPLC. Separation of structural isomers was realized. Mass spectrum, m/e Calcd for $C_{35}H_{34}Cl_2NO_8^+$: 666.17(100%), 668.16 (64%), 667.17(39.8%). Found: 666.46, 668.44, 667.51.

-continued

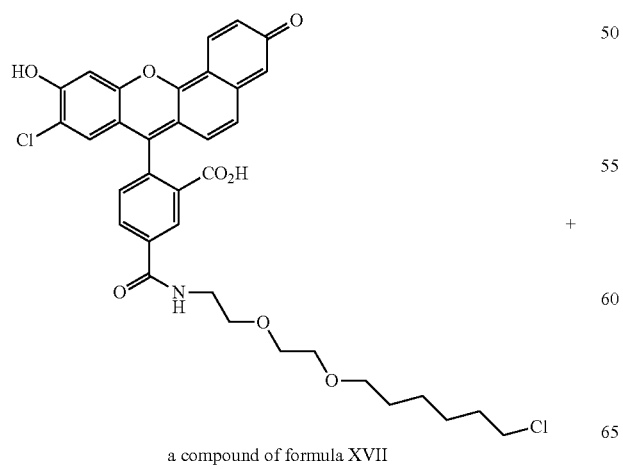

a compound of formula XVII

+

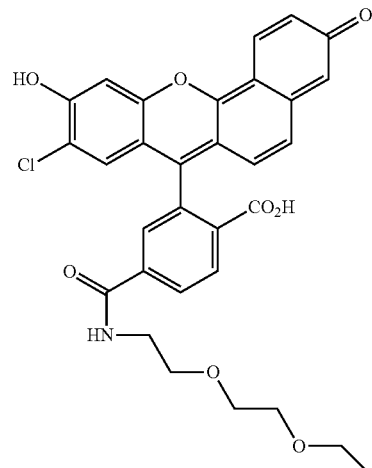

a compound of formula XVIII

N-{2-[2-(6-Chlorohexyloxy)-ethoxy]-ethyl}-seminaphthodimethylrhodamine-5-(and -6)-amide. The title compound was prepared using the above methodology. Purification was accomplished using preparative scale HPLC. Mass spectrum, m/e Calcd for $C_{37}H_{38}ClN_2O_7^-$: 657.24(100%), 658.24(42%), 659.23(32%). Found: 657.46, 658.47, 659.45.

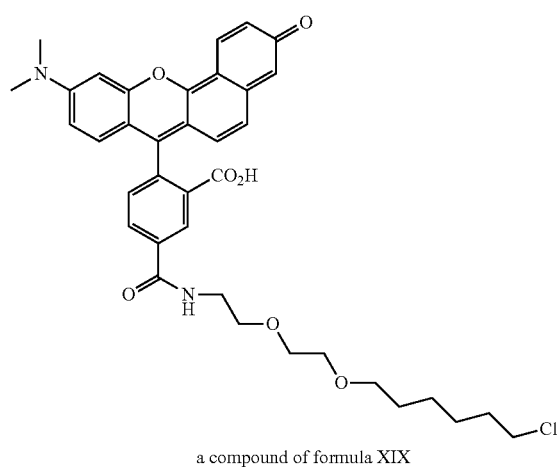

a compound of formula XIX

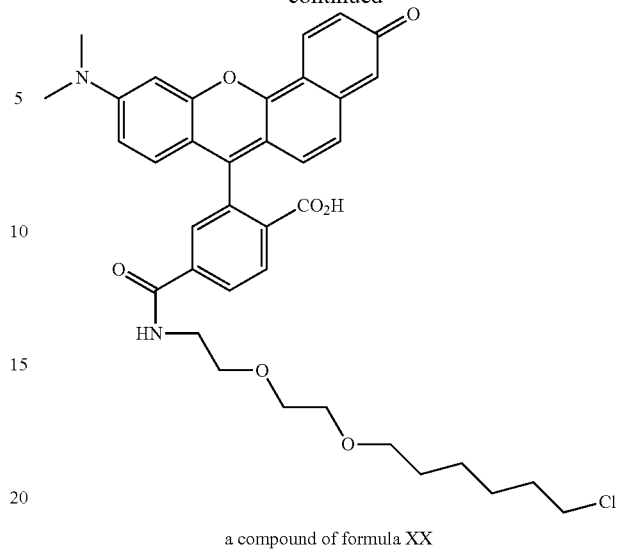

a compound of formula XX 6-(3',6'-dipivaloylfluorescein-5-(and-6)-carboxamido) hexanoic acid {2-[2-(6-chlorohexyloxy)-ethoxy]-ethyl}-amide. To a 100 ml round bottom flask containing 6-(3',6'-dipivaloylfluorescein-5-(and-6)-carboxamido) hexanoic acid succinimidyl ester (0.195 g, 0.26 mmol) was added 2-[2-(6-chlorohexyloxy)-ethoxy]-ethylamine (~0.44 mmol) in 25 ml $Et_2O$, followed by 2 ml of pyridine. The reaction mixture was allowed to stir overnight. After evaporation under reduced pressure, the residue was subjected to silica gel 60 column chromatography, progressively using 2% to 5% methanol in dichloromethane as eluent. The appropriate fractions were collected and dried under vacuum (0.186 g, 0.216 mmol, and 84% yield). Mass spectrum, m/e Calcd for $C_{47}H_{60}ClN_2O_{11}^+$: 863.39(100%), 864.39(54.4%), 865.39(34.6%). Found: 862.94, 864.07, 864.94.

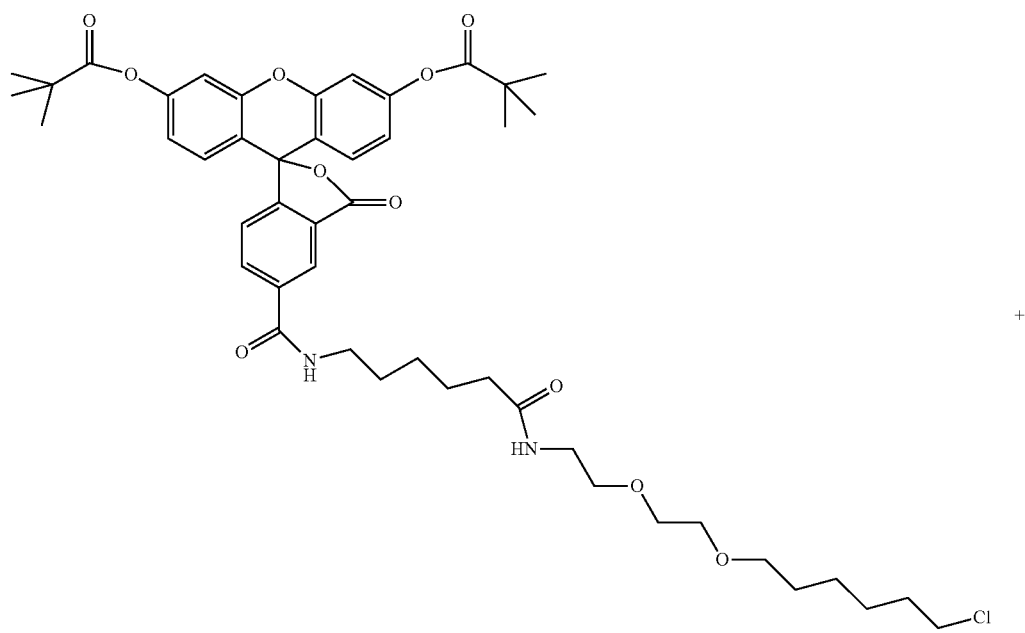

a compound of formula XXI

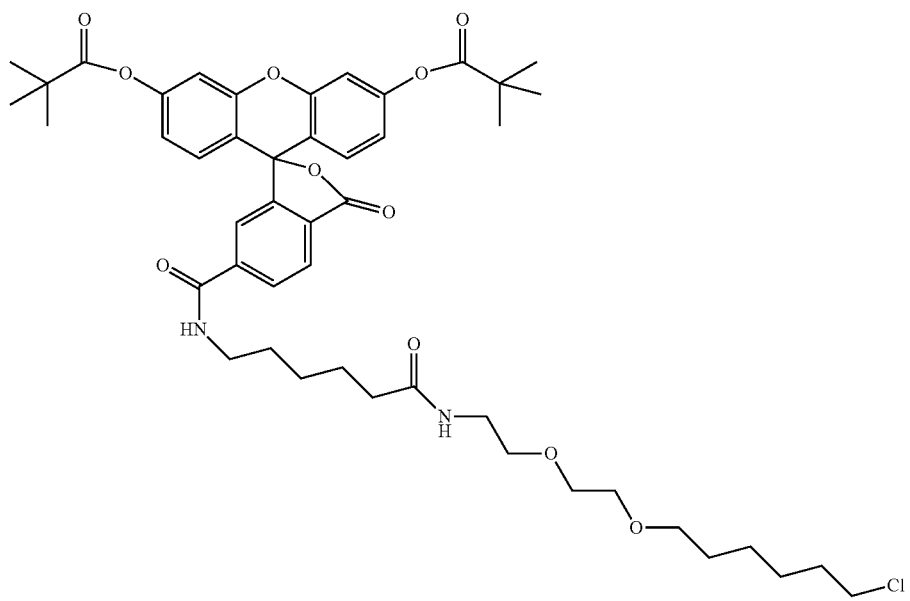

a compound of formula XXII 6-(fluorescein-5-(and-6)-carboxamido)hexanoic acid {2-[2-(6-chlorohexyloxy)-ethoxy]-ethyl}-amide. 6-(3',6'-dipivaloylfluorescein-5-(and-6)-carboxamido) hexanoic acid {2-[2-(6-chlorohexyloxy)-ethoxy]-ethyl}-amide (0.186 g, 0.216 mmol) was dissolved in 5 ml methanol and 0.5 ml 2M sodium carbonate(aq) added. The reaction mixture was stirred for 16 hours, then filtered. Purification was accomplished using preparative scale HPLC. Separation of structural isomers was realized. Mass spectrum, m/e Calcd for $C_{37}H_{44}ClN_2O_9^+$: 695.27(100.0%), 696.28(42.2%), 697.27(32.3%). Found:

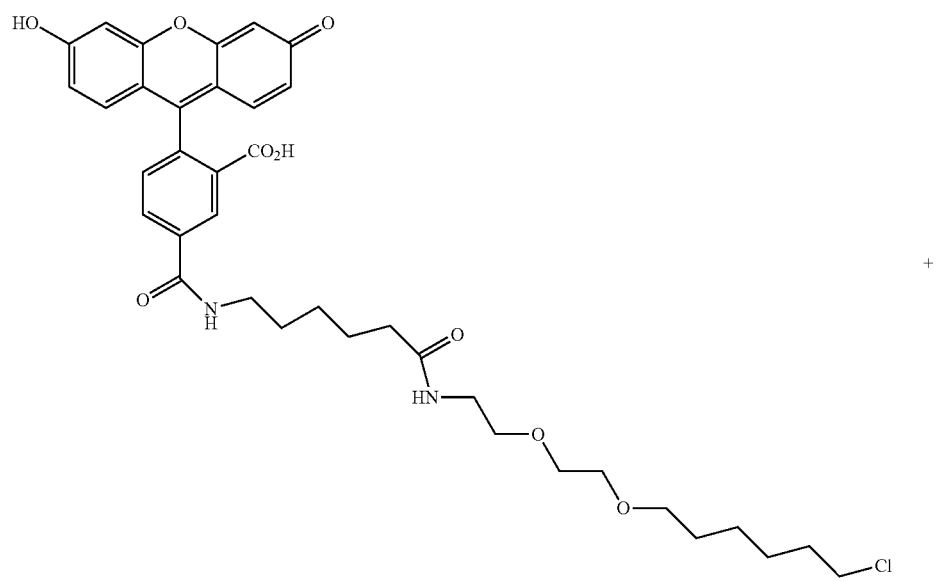

a compound of formula XXIII

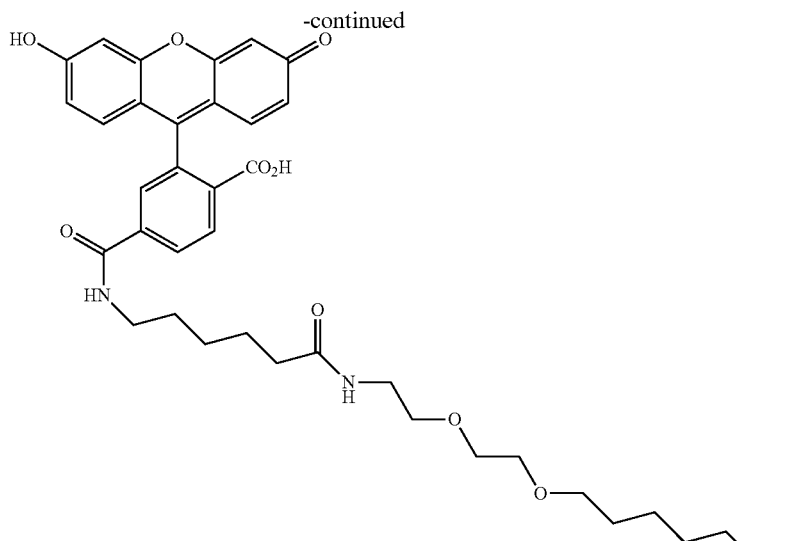

a compound of formula XXIV

{2-[2-(4-Chlorobutoxy)-ethoxy]ethyl}-carbamic acid anthracen-9-ylmethyl ester. A 50 ml round bottom flask was charged with [2-(2-Hydroxyethoxy)-ethyl]-carbamic acid anthracen-9-ylmethyl ester (0.25 g, 0.74 mmol) and fresh sodium hydride, 60% dispersion in mineral oil (150 mg, 3.75 mmol) under inert atmosphere. 10 ml anhydrous THF was added and the reaction allowed to stir for 5 minutes. After this point, 1-chloro-4-Iodobutane (180 μl, 1.5 mmol) is added via syringe. The reaction is stirred at room temperature for 24 hours. Silica gel 60 is co-absorbed onto the reaction mixture with loss of solvent under reduced pressure. Silica gel column chromatography takes place initially with heptane as eluent, followed by 10%, 20%, and 30% ethyl acetate. A total of 0.1 g (32% yield) of product is isolated from appropriate fractions: $^1$H NMR (CDCl$_3$) δ 8.50 (s, H-10), 8.40 (d, H-1, 8), 8.03 (d, H-4, 5), 7.53 (dt, H-2, 3, 6, 7), 6.15 (s, C$\underline{H}_2$-anth), 5.19 (m, exchangeable, N$\underline{H}$), 3.93-3.32 (m, 12H) 1.69-1.25 (m, 4H). Mass spectrum, m/e Calcd for C$_{24}$H$_{28}$ClNO$_4$.H$_2$O: 447.18 (100.0%), 448.18 (27.1%). Found: 447.17, 448.41.

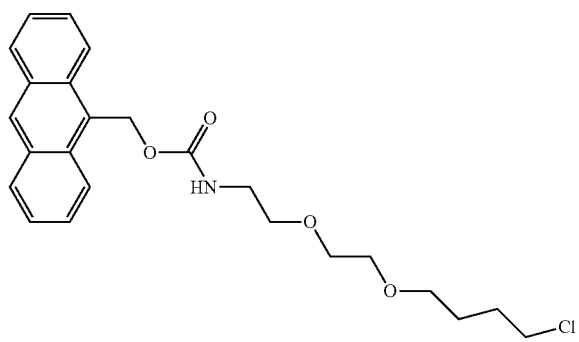

a compound of formula XXV 2-(2-{2-[2-(2-Chloroethoxy)-ethoxy]-ethoxy}-ethyl)-isoindole-1,3-dione. 2-(2-{2-[2-(2-Hydroxy-ethoxy)-ethoxy]-ethoxy}-ethyl)-isoindole-1,3-dione (0.5 g, 1.55 mmol) was prepared by the method of Nielsen, J. and Janda, K. D. (Methods: A Companion to Methods in Enzymology 6, 361-371 (1994)). To this reagent was added polystyrene-supported triphenylphosphine about 3 mmol P/g (0.67 g, 2 mmol) and 6 ml carbon tetrachloride, into a 25 ml round bottom fitted with a reflux condenser. The reaction set-up was sparged with argon then heated to reflux for 2 hours. Upon cooling, more polystyrene-supported triphenylphosphine (0.1 g, 0.3 mmol) was added and the reaction refluxed for an additional one hour. The cooled solution was filtered and the resin washed with additional carbon tetrachloride. Evaporation of solvent yielded 0.4 g (75.5% yield) of pure title compound: $^1$H NMR (CDCl$_3$) δ 7.82 (dd, 2H), 7.69 (dd, 2H), 3.88 (t, 2H), 3.71 (q, 4H), 3.63-3.56 (m, 12H). Mass spectrum, m/e Calcd for C$_{16}$H$_{21}$ClNO$_5^+$: 342.11 (100.0%), 344.11 (32.0%). Found: 341.65, 343.64.

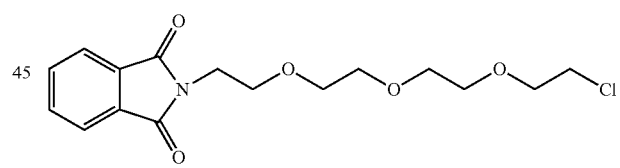

a compound of formula XXVI

2-[2-(2-{2-[2-(2-Chloroethoxy)-ethoxy]ethoxy}-ethoxy)-ethyl]-isoindole-1,3-dione. The title compound was prepared according to the previous example in 89% yield: $^1$H NMR (CDCl$_3$) δ 7.77 (dd, 2 H), δ 7.64 (dd, 2H), 3.83 (t, 2H), 3.67 (m, 4H), 3.60-3.52 (m, 14H). Mass spectrum, m/e Calcd for C$_{18}$H$_{25}$ClNO$_6^+$: 386.14 (100.0%), 388.13 (32.0%). Found: 385.88, 387.83.

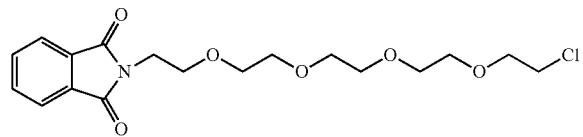

a compound of formula XXVII

2-{2-[2-(2-{2-[2-(2-Chloroethoxy)-ethoxy]ethoxy}-ethoxy)-ethoxy]-ethyl}-isoindole-1,3-dione. The title compound was prepared according to the synthesis of 2-(2-{2-[2-(2-Chloro-ethoxy)-ethoxy]-ethoxy}-ethyl)-isoindole-1,3-dione in 92% yield: $^1$H NMR (CDCl$_3$) δ 7.84 (dd, 2 H), 7.71 (dd, 2H), 3.90 (t, 2H), 3.74 (q, 4 H), 3.67-3.58 (m, 18H). Mass spectrum, m/e Calcd for $C_{20}H_{29}ClNO_7^+$: 430.16 (100.0%). Found: 429.85.

a compound of formula XXVIII

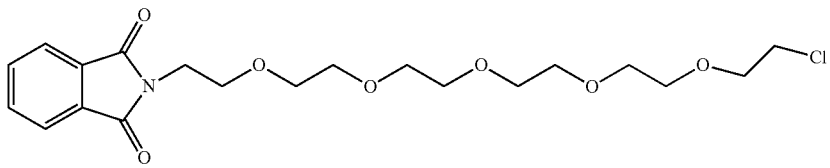

VI. Exemplary Methods of Use

The invention provides methods to monitor the expression, location and/or trafficking of molecules in a cell, as well as to monitor changes in microenvironments within a cell. In one embodiment, a mutant hydrolase and a corresponding substrate which includes a functional group are employed to label a cell, e.g., a cell in an organism or cell culture, or a cellular component. For instance, cells are contacted with a vector encoding the mutant hydrolase, such as one encoding a fusion between the mutant hydrolase and a nuclear localization signal. The expression of the vector in the cell may be transient or stable. Then the cell is contacted with a substrate of the invention recognized by the mutant hydrolase. Alternatively, cells are concurrently contacted with the vector and the substrate. Then the presence or location of the functional group of the substrate in the cell, a lysate thereof, or a subcellular fraction thereof, is detected or determined.

The substrates of the invention are preferably soluble in an aqueous or mostly aqueous solution, including water and aqueous solutions having a pH greater than or equal to about 6. Stock solutions of substrates of the invention, however, may be dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other non-hydroxylic, completely water-miscible solvents. In general, the amount of substrate of the invention employed is the minimum amount required to detect the presence of the functional group in the sample comprising a mutant hydrolase or a fusion thereof, within a reasonable time, with minimal background or undesirable labeling. The exact concentration of a substrate of the invention and a corresponding mutant hydrolase to be used is dependent upon the experimental conditions and the desired results. The concentration of a substrate of the invention typically ranges from nanomolar to micromolar. The required concentration for the substrate of the invention with a corresponding mutant hydrolase is determined by systematic variation in substrate until satisfactory labeling is accomplished. The starting ranges are readily determined from methods known in the art.

In one embodiment, a substrate which includes a functional group with optical properties is employed with a mutant hydrolase to label a sample. Such a substrate is combined with the sample of interest comprising the mutant hydrolase for a period of time sufficient for the mutant hydrolase to bind the substrate, after which the sample is illuminated at a wavelength selected to elicit the optical response of the functional group. Optionally, the sample is washed to remove residual, excess or unbound substrate. In one embodiment, the labeling is used to determine a specified characteristic of the sample by further comparing the optical response with a standard or expected response. For example, the mutant hydrolase bound substrate is used to monitor specific components of the sample with respect to their spatial and temporal distribution in the sample. Alternatively, the mutant hydrolase bound substrate is employed to determine or detect the presence or quantity of a certain molecule. In another embodiment, the mutant hydrolase bound substrate is used to analyze the sample for the presence of a molecule that responds specifically to the functional group.

A detectable optical response means a change in, or occurrence of, a parameter in a test system that is capable of being perceived, either by direct observation or instrumentally. Such detectable responses include the change in, or appearance of, color, fluorescence, reflectance, chemiluminescence, light polarization, light scattering, or x-ray scattering. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample comprising a mutant hydrolase or a fusion thereof or in a localized portion of the sample comprising a mutant hydrolase or a fusion thereof. Comparison of the degree of optical response with a standard or expected response can be used to determine whether and to what degree the sample comprising a mutant hydrolase or a fusion thereof possesses a given characteristic.

In another embodiment, the functional group is a ligand for an acceptor molecule. Typically, where the substrate comprises a functional group that is a member of a specific binding pair (a ligand), the complementary member (the acceptor) is immobilized on a solid or semi-solid surface, such as a polymer, polymeric membrane or polymeric particle (such as a polymeric bead). Representative specific binding pairs include biotin and avidin (or streptavidin or anti-biotin), IgG and protein A or protein G, drug and drug receptor, toxin and toxin receptor, carbohydrate and lectin or carbohydrate receptor, peptide and peptide receptor, protein and protein receptor, enzyme substrate and enzyme, sense DNA or RNA and antisense (complementary) DNA or RNA, hormone and hormone receptor, and ion and chelator. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. Where the functional group is a chelator of calcium, sodium, magnesium, potassium, or another biologically important metal ion, the substrate comprising such a functional group functions as an indicator of the ion. Alternatively, such a substrate may act as a pH indicator. Preferably, the detectable optical response of the ion indicator is a change in fluorescence.

The sample comprising a mutant hydrolase or a fusion thereof is typically labeled by passive means, i.e., by incubation with the substrate. However, any method of introducing the substrate into the sample comprising a mutant hydrolase or a fusion thereof, such as microinjection of a substrate into a cell or organelle, can be used to introduce the substrate into the sample comprising a mutant hydrolase or a fusion thereof. The substrates of the present invention are generally non-toxic to living cells and other biological components, within the concentrations of use.

The sample comprising a mutant hydrolase or a fusion thereof can be observed immediately after contact with a substrate of the invention. The sample comprising a mutant hydrolase or a fusion thereof is optionally combined with other solutions in the course of labeling, including wash solutions, permeabilization and/or fixation solutions, and other solutions containing additional detection reagents. Washing following contact with the substrate generally improves the detection of the optical response due to the decrease in non-specific background after washing. Satisfactory visualization is possible without washing by using lower labeling concentrations. A number of fixatives and fixation conditions are known in the art, including formaldehyde, paraformaldehyde, formalin, glutaraldehyde, cold methanol and 3:1 methanol:acetic acid. Fixation is typically used to preserve cellular morphology and to reduce biohazards when working with pathogenic samples. Selected embodiments of the substrates are well retained in cells. Fixation is optionally followed or accompanied by permeabilization, such as with acetone, ethanol, DMSO or various detergents, to allow bulky substrates of the invention, to cross cell membranes, according to methods generally known in the art. Optionally, the use of a substrate may be combined with the use of an additional detection reagent that produces a detectable response due to the presence of a specific cell component, intracellular substance, or cellular condition, in a sample comprising a mutant hydrolase or a fusion thereof. Where the additional detection reagent has spectral properties that differ from those of the substrate, multi-color applications are possible.

At any time after or during contact with the substrate comprising a functional group with optical properties, the sample comprising a mutant hydrolase or a fusion thereof is illuminated with a wavelength of light that results in a detectable optical response, and observed with a means for detecting the optical response. While some substrates are detectable colorimetrically, using ambient light, other substrates are detected by the fluorescence properties of the parent fluorophore. Upon illumination, such as by an ultraviolet or visible wavelength emission lamp, an arc lamp, a laser, or even sunlight or ordinary room light, the substrates, including substrates bound to the complementary specific binding pair member, display intense visible absorption as well as fluorescence emission. Selected equipment that is useful for illuminating the substrates of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This colorimetric absorbance or fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample comprising a mutant hydrolase or a fusion thereof is examined using a flow cytometer, a fluorescence microscope or a fluorometer, the instrument is optionally used to distinguish and discriminate between the substrate comprising a functional group which is a fluorophore and a second fluorophore with detectably different optical properties, typically by distinguishing the fluorescence response of the substrate from that of the second fluorophore. Where the sample comprising a mutant hydrolase or a fusion thereof is examined using a flow cytometer, examination of the sample comprising a mutant hydrolase or a fusion thereof optionally includes isolation of particles within the sample comprising a mutant hydrolase or a fusion thereof based on the fluorescence response of the substrate by using a sorting device.

In one embodiment, intracellular movements may be monitored using a fusion of the mutant hydrolase of the invention. For example, beta-arrestin is a regulator of G-protein coupled receptors, that moves from the cytoplasm to the cell membrane when it is activated. A cell containing a fusion of a mutant hydrolase and beta-arrestin and a substrate of the invention allows the detection of the movement of beta-arrestin from the cytoplasm to the cell membrane as it associates with activated G-protein coupled receptors.

In another embodiment, FRET may be employed with a fusion of the mutant hydrolase and a fluorescent protein, e.g., GFP, or a fusion with a protein that binds fluorescent molecules, e.g., O-alkylguanine-DNA alkyltransferase (AGT) (Keppler et al., 2003). Alternatively, a fusion of a mutant hydrolase and a protein of interest and a second fusion of a fluorescent protein and a molecule suspected of interacting with the protein of interest may be employed to study the interaction of the protein of interest with the molecule, e.g., using FRET. One cell may contain the fusion of a mutant hydrolase and a protein of interest while another cell may contain the second fusion of a fluorescent protein and a molecule suspected of interacting with the protein of interest. A population with those two cells may be contacted with a substrate and an agent, e.g., a drug, after which the cells are monitored to detect the effect of agent administration on the two populations.

In yet another embodiment, the mutant hydrolase is fused to a fluorescent protein. The fusion protein can thus be detected in cells by detecting the fluorescent protein or by contacting the cells with a substrate of the invention and detecting the functional group in the substrate. The detection of the fluorescent protein may be conducted before the detection of the functional group. Alternatively, the detection of the functional group may be conducted before the detection of the fluorescent protein. Moreover, those cells can be contacted with additional substrates, e.g., those having a different functional group, and the different functional group in the cell detected, which functional group is covalently linked to mutant hydrolase not previously bound by the first substrate.

In yet another embodiment, a fusion of a mutant hydrolase and a transcription factor may be employed to monitor activation of transcription activation pathways. For example, a fusion of a mutant hydrolase to a transcription factor present in the cytoplasm in an inactive form but which is translocated to the nucleus upon activation (e.g., NF kappa Beta) can monitor transcription activation pathways.

In another embodiment, biotin is employed as a functional group in a substrate and the fusion includes a mutant hydrolase fused to a protein of interest suspected of interacting with another molecule, e.g., a protein, in a cell. The use of such reagents permits the capture of the other molecule which interacts in the cell with the protein fused to the mutant hydrolase, thereby identifying and/or capturing (isolating) the interacting molecule(s).

In one embodiment, the mutant hydrolase is fused to a protein that is secreted. Using that fusion and a substrate of the invention, the secreted protein may be detected and/or monitored. Similarly, when the mutant hydrolase is fused to a membrane protein that is transported between different vesicular compartments, in the presence of the substrate, protein processing within these compartments can be detected. In yet another embodiment, when the mutant hydrolase is fused to an ion channel or transport protein, or a protein that is closely associated with the channel or transport protein, the movement of ions across cell or organelle membranes can be monitored in the presence of a substrate of the invention which contains an ion sensitive fluorophore. Likewise, when the mutant hydrolase is fused to proteins associated with vesicals or cytoskeleton, in the presense of the substrate, transport of proteins or vesicals along cytoskeletal structures can be readily detected.

In another embodiment, the functional group is a drug or toxin. By combining a substrate with such a functional group with a fusion of a mutant hydrolase and a targeting molecule such as an antibody, e.g., one which binds to an antigen associated with specific tumor cells, a drug or toxin can be targeted within a cell or within an animal. Alternatively, the functional group may be a fluorophore which, when present in a substrate and combined with a fusion of a mutant hydrolase and a targeting molecule such as a single chain antibody, the targeting molecule is labeled, e.g., a labeled antibody for in vitro applications such as an ELISA.

In yet another embodiment, when fused to a protein expressed on the cell surface, a mutant hydrolase on the cell surface, when combined with a substrate of the invention, e.g., one which contains a fluorophore, may be employed to monitor cell migration (e.g., cancer cell migration) in vivo or in vitro. In one embodiment, the substrate of the invention is one that has low or no permeability to the cell membrane. Alternatively, such a system can be used to monitor the effect of different agents, e.g., drugs, on different pools of cells. In yet another embodiment, the mutant hydrolase is fused to a HERG channel. Cells expressing such a fusion, in the presence of a substrate of the invention which includes a K+-sensitive fluorophore, may be employed to monitor the activity of the HERG channel, e.g., to monitor drug-toxicity.

In another embodiment, the substrate of the invention includes a functional group useful to monitor for hydrophobic regions, e.g., Nile Red, in a cell or organism.

Thus, the mutant hydrolases and substrates of the invention are useful in a wide variety of assays, e.g., phage display, panning, ELISA, Western blot, fluorometric microvolume assay technology (FMAT), and cell and subcellular staining.

The invention will be further described by the following non-limiting examples.

EXAMPLE I

General Methodologies

Unless defined otherwise, all technical and scientific terms used herein have the same meaning as commonly understood by one of ordinary skill in the field of molecular biology and cellular signaling and modeling. Generally, the nomenclature used herein and the laboratory procedures in spectroscopy, drug discovery, cell culture, molecular genetics, plastic manufacture, polymer chemistry, diagnostics, amino acid and nucleic acid chemistry, and alkane chemistry described below are those well known and commonly employed in the art. Standard techniques are typically used for preparation of plastics, signal detection, recombinant nucleic acid methods, polynucleotide synthesis, and microbial culture and transformation (e.g., electroporation, lipofection).

The techniques and procedures are generally performed according to conventional methods in the art and various general references (see generally, Sambrook et. al. Molecular Cloning: A laboratory manual, 2d ed. (1989) Cold Spring Harbor Laboratory Press, Cold Spring Harbor, N.Y., and Lakowicz, J. R. Principles of Fluorescence Spectroscopy, New York: Plenum Press (1983) for fluorescent techniques, which are incorporated herein by reference) and which are provided throughout this document. Standard techniques are used for chemical synthesis, chemical analysis, and biological assays.

Materials

All oligonucleotides were synthesized, purified and sequenced by Promega Corporation (Madison, Wis.) or the University of Iowa DNA Facility (Iowa City, Iowa). Restriction enzymes and DNA modifying enzymes were obtained from Promega Corporation (Madison, Wis.), New England Biolabs, Inc. (Beverly, Mass.) or Stratagene Cloning Systems (La Jolla, Calif.), and were used according to the manufacturer's protocols. Competent *E. coli* JM109 were provided by Promega Corporation or purchased from Stratagene Cloning Systems. Small-scale plasmid DNA isolations were done using the Qiagen Plasmid Mini Kit (Qiagen Inc., Chatsworth, Calif.). DNA ligations were performed with pre-tested reagent kits purchased from Stratagene Cloning Systems. DNA fragments were purified with QIAquick Gel Extraction Kits or QIAquick PCR purification Kits purchased from Qiagen Inc.

The vectors used for generating DhaA mutants and their fusions were as follows: pET21 (Invitrogen, Carlsbad, Calif.), pRL-null (Promega, Madison, Wis.), pGEX-5x-3 (Amersham Biosciences; Piscataway, N.J.), and EGFP and DsRED2 (both from CLONTECH, Palo Alto, Calif.).

SDS-polyacrylamide gels and associated buffers and stains, as well as electroblot transfer buffers, were obtained from BioWhittaker Molecular Applications (Rockland, Me.). Protein molecular weight standards were purchased from Invitrogen.

Sigma-Aldrich was the source of Anti Flag$^R$ monoclonal antibody antibodies (anti FLAG$^R$ M2 monoclonal antibody (mouse) (F3165)), Anti FLAG$^R$ M2 HRP Conjugate and Anti FLAG$^R$ M2 FITC conjugate (A8592 and F4049, respectively). Chemicon (Temecula, Calif.) was the source of monoclonal anti-Renilla luciferase antibody (MAB4410). Promega Corp. was the source of HRP-conjugated goat anti-mouse IgG and HRP-conjugated streptavidin (W4021 and G714, respectively).

1-Cl-butane, 1-Cl-hexane, 1-Cl-octane, 1-Cl-decane, 1-Cl-butanol, 1-Cl-hexanol, 1-Cl-octanol, and 1-Cl-decanol were obtained from Aldrich or from Fluka (USA). All salts, monobasic potassium phosphate, dibasic potassium phosphate, imidazole, HEPES, sodium EDTA, ammonium sulfate, and Tris free base were from Fisher (Biotech Grade).

Glutathione Sepharose 4 FF, glutathione, MonoQ and Sephadex G-25 prepackaged columns were from Amersham Biosciences.

Luria-Broth ("LB") was provided by Promega Corporation.

Methods

PCR Reactions. DNA amplification was performed using standard polymerase chain reaction buffers supplied by Promega Corp. Typically, 50 µl reactions included 1× concentration of the manufacturer's supplied buffer, 1.5 mM MgCl$_2$, 125 µM dATP, 125 µM dCTP, 125 µM dGTP, 125 µM dTTP, 0.10-1.0 µM forward and reverse primers, 5 U Ampli- Taq® DNA Polymerase and <1 ng target DNA. Unless otherwise indicated, the thermal profile for amplification of DNA was 35 cycles of 0.5 minutes at 94° C.; 1 minute at 55° C.; and 1 minute at 72° C.

DNA Sequencing. All clones were confirmed by DNA sequencing using the dideoxy-terminal cycle-sequencing method (Sanger et al., 1977) and a Perkin-Elmer Model 310 DNA sequencer. (Foster City, Calif.).

SDS-PAGE. Proteins were solubilized in a sample buffer (1% SDS, 10% glycerol, and 1.0 mM β-mercaptoethanol, pH 6.8; Promega Corporation), boiled for 5 minutes and resolved on SDS-PAGE (4-20% gradient gels; BioWhittaker Molecular Applications). Gels were stained with Coomassie Blue (Promega Corp.) for Western blot analysis or were analyzed on a fluoroimager (Hitachi, Japan) at an $E_{ex}/E_{em}$ appropriate for each fluorophore evaluated.

Western Blot Analysis. Electrophoretic transfer of proteins to a nitrocellulose membrane (0.2 μm, Scheicher & Schuell, Germany) was carried out in 25 mM Tris base/188 mM glycine (pH 8.3), 20% (v/v) methanol for 2.0 hours with a constant current of 80 mA (at 4° C.) in Xcell II Blot module (Invitrogen). The membranes were rinsed with TBST buffer (10 mM Tris-HCl, 150 mM NaCl, pH 7.6, containing 0.05% Tween 20) and incubated in blocking solution (3% dry milk or 1% BSA in TBST buffer) for 30 minutes at room temperature or overnight at 4° C. Then membranes were washed with 50 ml of TBST buffer and incubated with anti-FLAG$^R$ monoclonal antibody M2 (dilution 1:5,000), anti-Renilla luciferase monoclonal antibody (dilution 1:5,000), or HRP-conjugated streptavidin (dilution 1:10,000) for 45 minutes at room temperature. Then the membranes were washed with TBST buffer (50 ml, 5 minutes, 3 times). The membranes that had been probed with antibody were then incubated with HRP-conjugated donkey anti-mouse IgG (30 minutes, room temperature) and then the washing procedure was repeated. The proteins were visualized by the enhanced chemiluminescence (ECL) system (Pharmacia-Amersham) according to the manufacturer's instructions. Levels of proteins were quantified using computer-assisted densitometry.

Protein Concentration. Protein was measured by the microtiter protocol of the Pierce BCA Protein assay (Pierce, Rockford, Ill.) using bovine serum albumin (BSA) as a standard.

Statistic Analysis. Data were expressed as mean+/−S.E.M. values from experiments performed in quadruplicate, representative of at least 3 independent experiments with similar results. Statistical significance was assessed by the student's t test and considered significant when p<0.05.

Bacterial Cells. The initial stock of Dh5α cells containing pET-3a with Rhodococcus rodochorus (DhaA) was kindly provided by Dr. Clifford J. Unkefer (Los Alamos National Laboratory, Los Alamos, N. Mex.) (Schindler et al., 1999; Newman et al., 1999). Bacteria were cultured in LB using a premixed reagent provided by Promega Corp. Freezer stocks of E. coli BL21 (λDE3) pET3a (stored in 10% glycerol, −80° C.) were used to inoculate Luria-Bertani agar plates supplemented with ampicillin (50 μg/ml) (Sambrook et al., 1989). Single colonies were selected and used to inoculate two 10 ml cultures of Luria-Bertani medium containing 50 μg/ml ampicillin. The cells were cultured for 8 hours at 37° C. with shaking (220 rpm), after which time 2 ml was used to inoculate each of two 50 ml of Luria-Bertani medium containing 50 μg/ml ampicillin, which were grown overnight at 37° C. with shaking. Ten milliliters of this culture was used to inoculate each of two 0.5 L Luria-Bertani medium with ampicillin. When the $A_{600}$ of the culture reached 0.6, isopropyl-1-thio-β-D-galactopyranoside (IPTG) was added to a final concentration of 0.5 mM, and cultures were maintained for an additional 4 hours at 30° C. with shaking. The cells were then harvested by centrifugation and washed with 10 mM Tris-$SO_4$, 1 mM EDTA, pH 7.5. The cell pellets were stored at −70° C. prior to cell lysis.

Mammalian Cells. CHO—K1 cells (ATCC-CCL61) were cultured in a 1:1 mixture of Ham's F12 nutrients and Dulbecco's modified minimal essential medium supplemented with 10% fetal bovine serum (FBS), 100 U/ml penicillin, and 100 mg/ml streptomycin, in an atmosphere of 95% air and 5% $CO_2$ at 37° C.

Rat hippocampal (E18) primary neurons were isolated as described below. Briefly, fragments of embryonic (E18) rat hippocampus in Hibernate™ E media (GIBCO, Invitrogen, Carlsbad, Calif.), obtained from Dr. Brewer (Southern Illinois University), were dissociated and plated on poly-D-lysin coated (0.28 mg/cm$^2$; Sigma) glass/plastic-ware and cultured in serum-free Neurobasal™ media with B27 supplement (NB27, GIBCO). All media were changed every 2-3 days.

Transfection. To study transient expression of different proteins, cells were plated in 35 mm culture dishes or 24 well plates. At about 80-90% confluency, the cells were exposed to a mixture of lipofectamine/DNA/antibiotic free media according to the manufacturer's (GIBCO) instructions. The following day, media was replaced with fresh media and cells were allowed to grow for various periods of time.

Fluorescence. Fluorescence in cells in 96 well plates was measured on fluorescent plate reader CytoFluorII (Beckman) at an $E_{ex}/E_{em}$ appropriate for particular fluorophores (e.g., $E_{ex}/E_{em}$ for TAMRA is 540/575 nm).

EXAMPLE II

A DhaA-Based Tethering System

A. Wild-Type and Mutant DhaA Proteins and Fusions Thereof

A halo-alkane dehydrogenase from Rhodococcus rhodochrous is a product of the DhaA gene (MW about 33 kDa). This enzyme cleaves carbon-halogen bonds in aliphatic and aromatic halogenated compounds, e.g., HaloC$_3$-HaloC$_{10}$. The catalytic center of DhaA is a typical "catalytic triad", comprising a nucleophile, an acid and a histidine residue. It is likely that substrate binds to DhaA to form an E.S complex, after which nucleophilic attack by Asp106 forms an ester intermediate, His 272 then activates $H_2O$ that hydrolyzes the intermediate, releasing product from the catalytic center. To determine whether a point mutation of the catalytic His272 residue impairs enzymatic activity of the enzyme so as to enable covalent tethering of a functional group (FG) to this protein, mutant DhaAs were prepared.

Materials and Methods

To prepare mutant DhaA vectors, Promega's in vitro mutagenesis kit which is based on four primer overlap-extension method was employed (Ho et al., 1989) to produce DhaA.H272 to F, A, G, or H mutations. The external primers were oligonucleotides 5'-GCTTCACTTGTCGTCATCGTC-CTTGTAGTCA-3' (SEQ ID NO:1) and 5'-GCTTCACT-TGTCGTCATCGTCCTTGTAGTCA-3' (SEQ ID NO:2), and the internal mutagenic primers were as follows: H272F (5'-CCGGGATTG<u>TTC</u>TACCTCCAGGAAGAC-3'), SEQ ID NO:3), H272A (5'-CCGGGATTG<u>GCC</u>TACCTCCAGGAAGAC-3'; SEQ ID NO:4), H272G (5'-CCGGGATTG<u>CAG</u>TACCTCCAGGAAGAC-3'; SEQ ID NO:5), and H272Q (5'-CCGGGATTG<u>GGC</u>TACCTCCAGGAAGAC-3'; SEQ ID NO:6) (the mutated codons are underlined). The mutated dehalogenase genes were subcloned into the pET-3a vector. For overexpression of mutant dehalogenases, the pET-3a vector was transformed into competent E. coli BL21 (DE3). The DhaA sequence in clones was confirmed by DNA sequencing.

GST-DhaA (WT or H272F/A/G/H mutants) fusion cassettes were constructed by cloning the appropriate DhaA coding regions into SalI/NotI sites of pGEX5x3 vector. Two primers (5'-ACGCGTCGACGCCGCCATGTCA-GAAATCGGTACAGGC-3' and 5'-ATAAGAATGCGGC-CGCTCAAGCGCTTCAACCGGTGAGT-GCGGGGAGCCA GCGCGC-3'; SEQ ID NOs:7 and 8, respectively) were designed to add a SalI site and a Kozak consensus sequence to the 5' coding regions of DhaA, to add a NotI, EcoR47III, and AgeI restriction site and stop codons to the 3' coding region of DhaA, and to amplify a 897 bp fragment from a DhaA (WT or mutant) template. The resulting fragments were inserted into the SalI/NotI site of pGEX-5X-3, a vector containing a glutathione S-transferase (GST) gene, a sequence encoding a Factor Xa cleavage site, and multiple cloning sites (MCS) followed by a stop codon.

A Flag coding sequence was then inserted into the AgeI/EcoR47III restriction sites of the pGEX5X-3 vector. In frame with the six nucleotide AgeI site is a sequence for an 11 amino acid peptide, the final octapeptide of which corresponds to the Flag peptide (Kodak Imaging Systems, Rochester, N.Y.). Two complementary oligonucleotides (5'-CCGGTGACTA-CAAGGACGATGACGACAAGTGAAGC-3', sense, SEQ ID NO:9, and 5'-GCTTCACTTGTCGTCATCGTCCTTG-TAGTCA-3', antisense, SEQ ID NO:10) coding the Flag peptide (Kodak Imaging Systems, Rochester, N.Y.) were annealed. The annealed DNA had an AgeI site at the 5' end and an EcoR47III at the 3' end. The annealed DNA was digested with AgeI and EcoR47III and then subcloned into the GST-DhaA.WT or GST-DhaA.H272F mutant constructs at the AgeI and EcoR47III sites. All gene fusion constructs were confirmed by DNA sequencing.

To generate GST-DhaA fusion proteins, enzyme expression was induced by the addition of isopropyl-b-D-thiogalactopyranoside (at a final concentration of 0.5 mM) when the culture reached an optical density of 0.6 at 600 nm. The cells were harvested in Buffer A (10 mM Tris-$SO_4$, 1 mM EDTA, 1 mM β-mercaptoethanol, and 10% glycerol, pH 7.5), and disrupted by sonication using a Vibra Cell™ sonicator (Sonics & Materials, Danbury, Conn., USA). Cell debris was removed by centrifugation at 19,800×g for 1 hour. The crude extract was further purified on a GSS-Sepharose 4 fast flow column (Amersham Biosciences; Piscataway, N.J.) according to the manufacturer's instructions. The elution fractions containing GST-DhaA fusion protein were pooled, dialyzed against a 10 mM Tris-$SO_4$ buffer (containing 20 mM $Na_2SO_4$ and 1 mM EDTA-$Na_2$) overnight at 4° C., and stored at −20° C. until use. To generate DhaA (WT or mutant), GST was cleaved from the fusion proteins with Factor Xa, and the products purified on GSS-Sepharose 4 (Amersham Biosciences; Piscataway, N.J.) according to the manufacturer's instructions. Homogeneity of the proteins was verified by SDS-PAGE. In some experiments, the cell free extract was fractionated using 45-70% saturated ammonium sulfate as described by Newman et al. (1999).

Results

Figure 3:
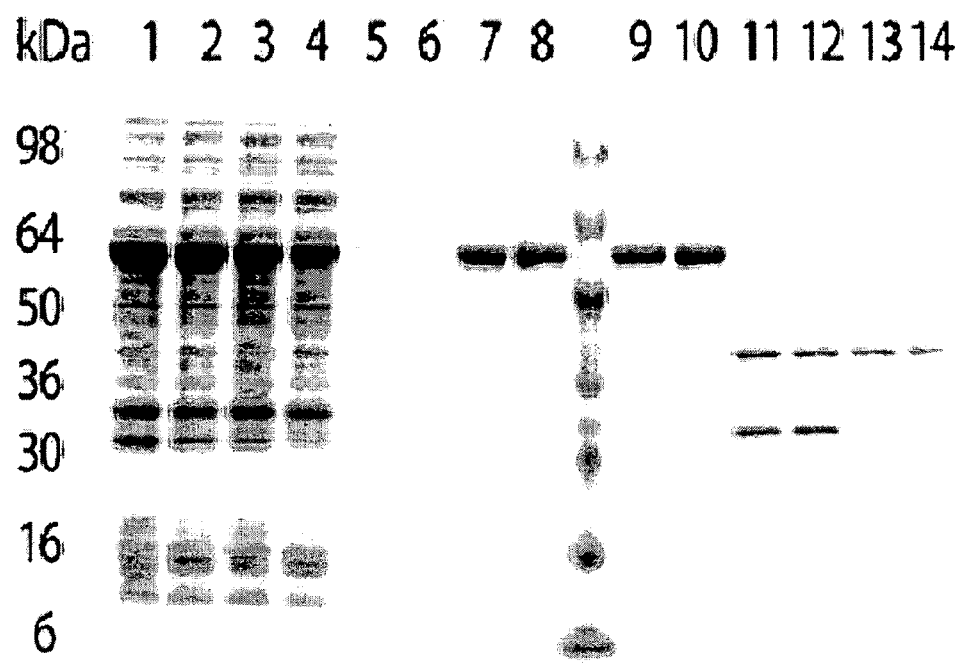
FIG. 3 shows the purification of wild-type and mutant DhaA proteins. GST-DhaA.WT-Flag (odd numbered lanes) and GST-DhaA.H272F-Flag (even numbered lanes) fusion proteins were found to be soluble and efficiently purified on GSS-Sepharose 4FF (lanes 3 and 4-crude *E. coli* supernatant; lanes 5 and 6-washes; lanes 7 through 10-purified proteins). Treatment of the fusion proteins with Factor Xa led to the formation of two proteins, GST and DhaA (WT or mutant; lanes 11 and 12, respectively). Moreover, GST was efficiently removed on GSS-Sepharose 4FF (WT or mutant; lanes 13 and 14, respectively). All proteins had the predicted molecular weight.

FIG. 3 shows robust, IPTG inducible production of GST-DhaA.WT-Flag (lane 1) and GST-DhaA.H272F-Flag (lane 2) fusion proteins. Moreover, the proteins were soluble and could be efficiently purified on GSS-Sepharose 4FF (lanes 5-10, odd numbered lanes correspond to GST-DhaA.WT-Flag and even numbered lanes correspond to GST-DhaA.H272F-Flag). Treatment of the fusion proteins with Factor Xa led to the formation of two proteins GST and DhaA (WT or mutant, lanes 11 and 12, respectively), and GST was efficiently removed on GSS-Sepharose 4FF (WT or mutant, lanes 13 and 14, respectively). In addition, all proteins had the predicted molecular weight.

B. Mutation of H272 Impairs Ability of DhaA to Hydrolyze Cl-Alkanes.

Inability of an enzyme to release product of the enzymatic reaction into surrounding media is essential for the tethering system. This inability can be detected by significant reduction of the hydrolytic activity of the enzyme.

To study the effect of a point mutation on the activity of DhaA (WT or mutant) hydrolysis of Cl-alkanes, a pH-indicator dye system as described by Holloway et al. (1998) was employed.

Materials and Methods

The reaction buffer for a pH-indicator dye system consisted of 1 mM HEPES-$SO_4$ (pH 8.2), 20 mM $Na_2SO_4$, and 1 mM EDTA. Phenol red was added to a final concentration 25 μg/ml. The halogenated compounds were added to apparent concentrations that could insure that the dissolved fraction of the substrate was sufficient for the maximum velocity of the dehalogenation reaction. The substrate-buffer solution was vigorously mixed for 30 seconds by vortexing, capped to prevent significant evaporation of the substrate and used within 1-2 hours. Prior to each kinetic determination, the phenol red was titrated with a standardized solution of HCl to provide an apparent extinction coefficient. The steady-state kinetic constants for DhaA were determined at 558 nm at room temperature on a Beckman Du640 spectrophotometer (Beckman Coulter, Fullerton, Calif.). Kinetic constants were calculated from initial rates using the computer program SigmaPlot. One unit of enzyme activity is defined as the amount required to dehalogenate 1.0 mM of substrate/minute under the specific conditions.

Results

Figure 4:
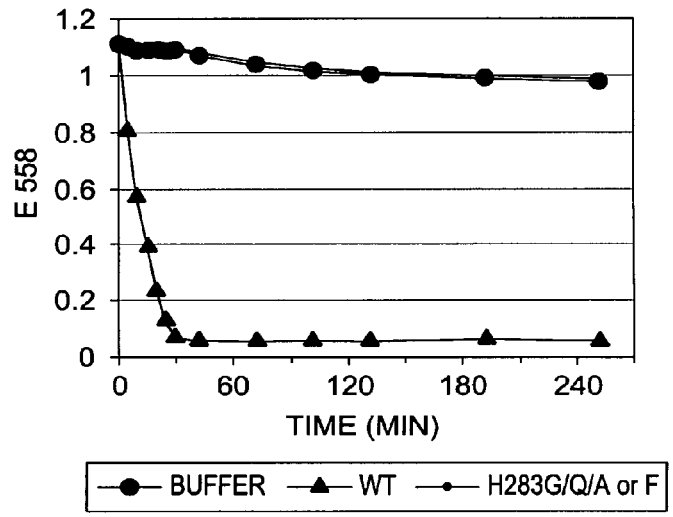
FIG. 4 illustrates the hydrolysis of 1-Cl-butane by wild-type DhaA and mutant DhaAs.

As shown in FIG. 4, using 0.1 mg/ml of enzyme and 10 mM substrate at pH 7.0-8.2, no catalytic activity was found with any of four mutants. Under these conditions, the wild-type enzyme had an activity with 1-Cl-butane of 5 units/mg of protein. Thus, the activity of the mutants was reduced by at least 700-fold.

Aliquots of the supernatant obtained from E. coli expressing DhaA (WT or one of the mutants) were treated with increasing concentrations of $(NH_4)_2SO_4$. The proteins were exposed to each $(NH_4)_2SO_4$ concentration for 2 hours (4° C.), pelleted by centrifugation, dialyzed overnight against buffer A, and resolved on SDS-PAGE.

Figures 5A, 5B:
FIG. 5 shows precipitation of DhaA.WT and DhaA.H272F/A/G/Q mutants with various concentrations of $(NH_4)_2SO_4$. Lanes 1, 5, and 9, 0% $(NH_4)_2SO_4$; lanes 2, 6, and 10, 10% $(NH_4)_2SO_4$; lanes 3, 7, and 11, 10-45% $(NH_4)_2SO_4$; and lanes 4, 8, and 12, 45-70% $(NH_4)_2SO_4$. Panel A: lanes 1-4, DhaA.WT; lanes 5-8, DhaA.H272G; and lanes 9-12, DhaA.H272Q. Panel B: lanes 1-4, DhaA.WT; lanes 5-8, DhaA.H272F; and lanes 9-12, DhaA.H272A.

As shown in FIG. 5, a major fraction of DhaA.WT and the DhaA.H272F mutant was precipitated by 45-70% of $(NH_4)_2SO_4$. No precipitation of these proteins was observed at low $(NH_4)_2SO_4$ concentrations. In contrast, the DhaA.H272Q, DhaA.H272G and DhaA.H272A mutants could be precipitated by 10% $(NH_4)_2SO_4$. This is a strong indication of the significant change of the physico-chemical characteristics of the DhaA.H272Q, DhaA.H272G and DhaA.H272A mutants. At the same time, the DhaA.H272F mutation had no significant effect on these parameters. These data are in good agreement with results of computer modeling of the effect of mutations on the 3-D structure of DhaA, indicating that among all tested mutants, only the DhaA.H272F mutation had no significant effect on the predicted 3-dimensional model (see FIG. 2). Based on these results, DhaA.H272F was chosen for further experiments.

Figure 2A:
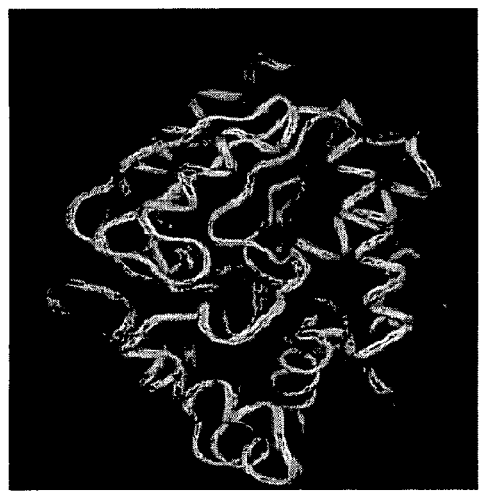
FIG. 2 shows a three-dimensional model of a wild-type DhaA *Rhodococcus rhodochrous* dehalogenase and four mutant DhaAs (H283Q, G, A or F). A cyan ribbon is a 3-D model of the DhaA.WT based on the crystal structure of this protein (Newman et al., 1999) (panel A). The purple ribbon is a 3-D model of the H272Q, H272G and H272A mutants (panel A), or a 3-D model of the H272F mutant (panel B). Three-dimensional models were generated by calculating a Molecular Probability Density Function followed by several optimization steps including Restrained Stimulated Annealing Molecular Dynamics (MD) scheme. 3-D modeling was done on Silicon Graphics computer-station using software InsightII (USA).
Figure 2B:
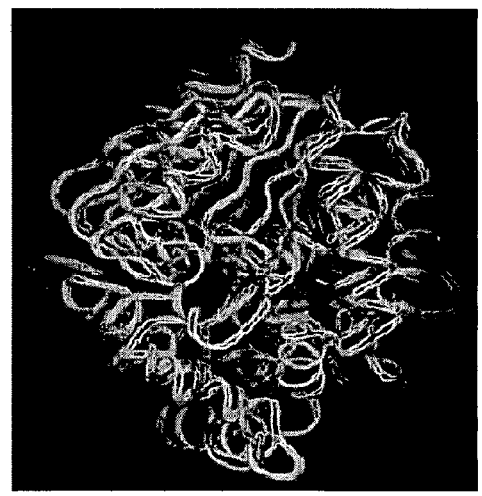

To form a covalent adduct, the chlorine atom of Cl-alkane is likely positioned in close proximity to the catalytic amino acids of DhaA (WT or mutant) (FIG. 2). The crystal structure of DhaA (Newman et al., 1999) indicates that these amino acids are located deep inside of the catalytic pocket of DhaA (approximately 10 Å long and about 20 Å$^2$ in cross section). To permit entry of the reactive group in a substrate for DhaA which includes a functional group into the catalytic pocket of DhaA, a linker was designed to connect the Cl-containing substrate with a functional group so that the functional group is located outside of the catalytic pocket, i.e., so as not to disturb/destroy the 3-D structure of DhaA.

Figure 6:
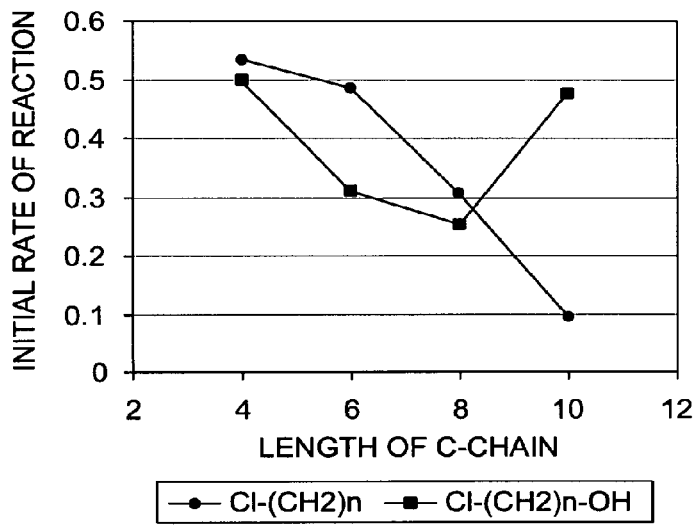
FIG. 6 depicts the substrate specificity of wild-type DhaA. Using a phenol red-based assay ($E_{558}$), the initial rate of the reaction was determined during the first 60 seconds after enzyme addition by four 15 second readings.

To determine if DhaA is capable of hydrolyzing Cl-alkanes with a long hydrophobic carbon chain, DhaA.WT was contacted with various Cl-alkane alcohols. As shown in FIG. 6, DhaA.WT can hydrolyze 1-Cl-alkane alcohols with 4-10 carbon atoms. Moreover, the initial rate of hydrolysis (IRH) of Cl-alkanes had an inverse relationship to the length of a carbon chain, although poor solubility of long-chain Cl-alkanes in aqueous buffers may affect the efficiency of the enzyme-substrate interaction. Indeed, as shown in FIG. 6, the IRH of 1-Cl-alkane-10-decanol is much higher than the IRH of 1-Cl-decane. More importantly, these data indicate that DhaA can hydrolyze Cl-alkanes containing relatively polar groups (e.g., HO-group).

Figure 7:
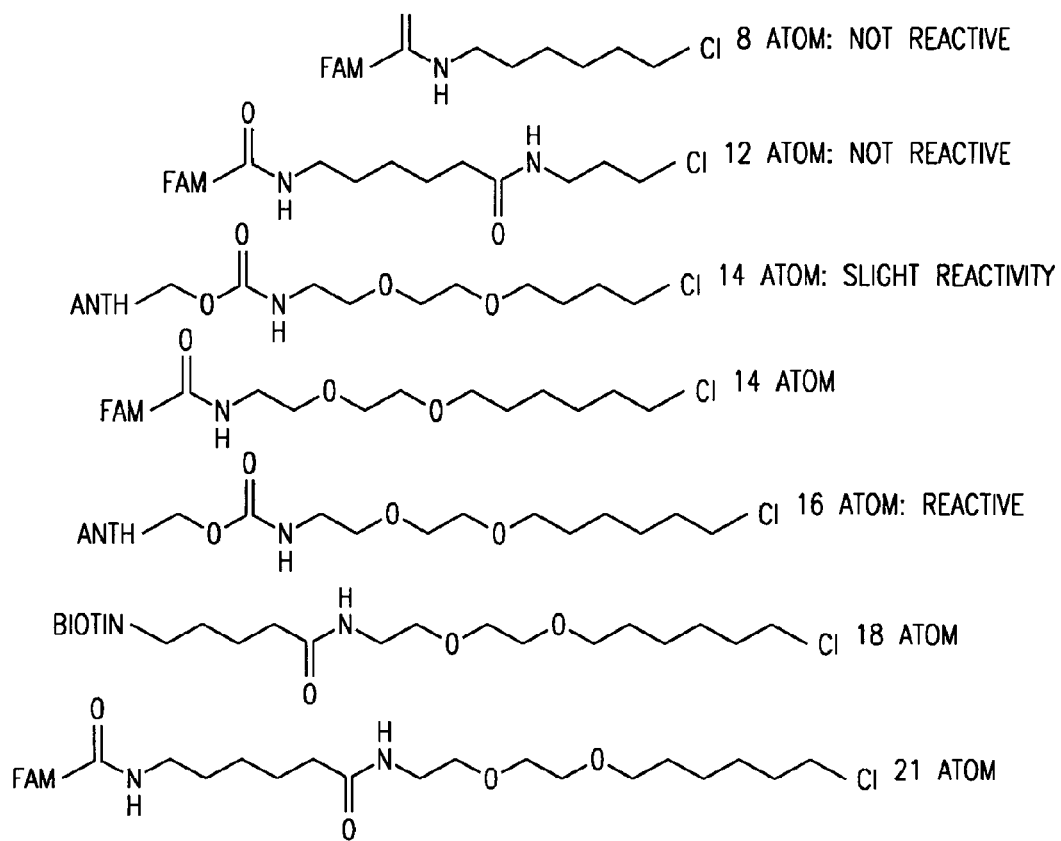
FIG. 7 shows substrates for DhaA which include a functional group (e.g., 5-(and 6-)-carboxyfluorescein (FAM), Anth (anthracene) or biotin) and a linker.

FAM-modified Cl-alkanes with linkers of different length and/or hydrophobicity were prepared (FIG. 7). DhaA.WT efficiently hydrolyzed Cl-alkanes with a relatively bulky functional group (FAM) if the linker was 12 or more atoms long. No activity of DhaA.H272F/A/G/Q mutants was detected with any of the tested Cl-alkanes (data not shown). In addition, modification of the $(CH_2)_6$ region adjacent to the Cl-atom led to a significant reduction of the IRH of the 14-atom linker by DhaA.WT. Nevertheless, if the length and structure of the linker is compatible with the catalytic site of a hydrolase, the presence of a linker in a substrate of the invention has substantially no effect on the reaction.

Some of the samples were analyzed on an automated HPLC (Hewlett-Packard Model 1050) system. A DAD detector was set to record UV-visible spectra over the 200-600 nm range. Fluorescence was detected at an $E_{ex}/E_{em}$ equal 480/520 nm and 540/575 nm for FAM- and TAMRA-modified substrates, respectively. Ethanol extracts of Cl-alkanes or products of Cl-alkane hydrolysis were analyzed using analytical reverse phase $C_{18}$ column (Adsorbosphere HS, 5μ, 150×4.6 mm; Hewlett-Packard, Clifton, N.J.) with a linear gradient of 10 mM ammonium acetate (pH 7.0):ACN (acetonitrile) from 25:75 to 1:99 (v/v) applied over 30 minutes at 1.0 ml/minute. Quantitation of the separated compounds was based on the integrated surface of the collected peaks.

Figure 8A:
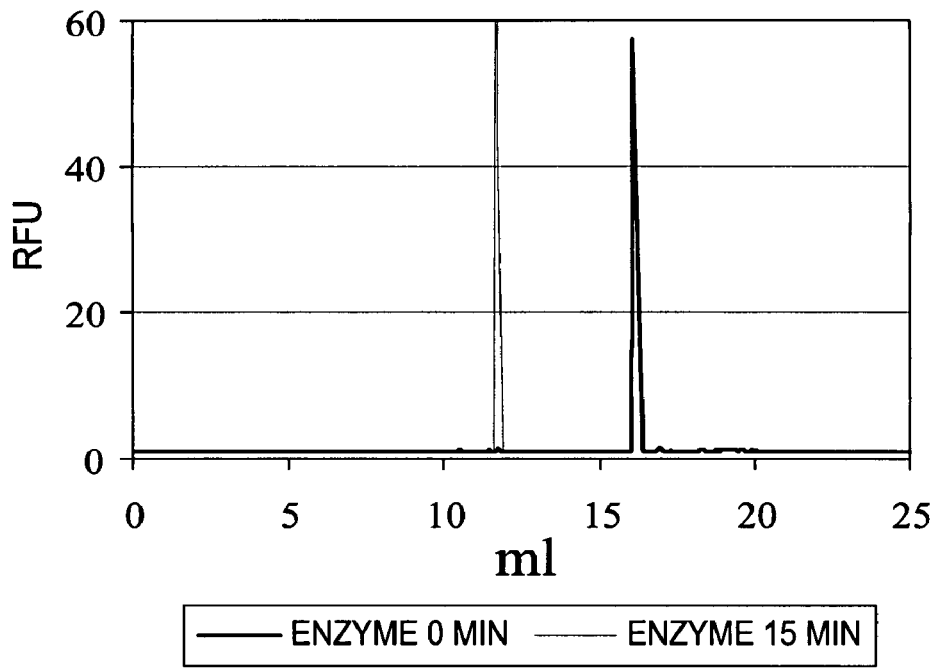
FIG. 8A shows a HPLC separation of products of FAM-$C_{14}H_{24}O_4$—Cl hydrolysis by wild-type DhaA.
Figure 8B:
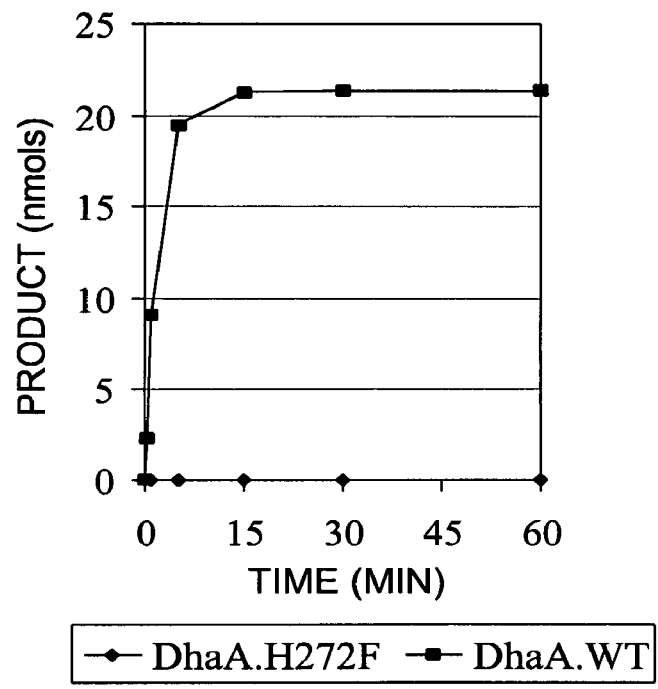
FIG. 8B shows a HPLC analysis of product (as a percent of substrate) produced by wild-type DhaA hydrolysis of FAM-$C_{14}H_{24}O_4$—Cl over time.

FIG. 8A shows the complete separation of the substrate and the product of the reaction. FIG. 8B indicates that wild-type DhaA very efficiently hydrolyzed FAM-$C_{14}H_{24}O_4$—Cl. Similar results were obtained when TAMRA-$C_{14}H_{24}O_4$—Cl or ROX.5-$C_{14}H_{24}O_4$—Cl were used as substrates (data not shown). Taken together these data confirm the results of the pH-indicator dye-based assay showing complete inactivation of DhaA by the DhaA.H272F mutation.

C. Covalent Tethering of Functional Groups to DhaA Mutants In Vitro

Materials and Methods

MALDI analysis of proteins was performed at the University of Wisconsin Biotechnology Center using a matrix assisted laser desorption/ionization time-of-life (MALDI-TOF) mass spectrometer Bruker Biflex III (Bruker, USA.). To prepare samples, 100 μg of purified DhaA (WT or H272F mutant) or GST-DhaA (WT or H272F mutant) fusion protein (purified to about 90% homogeneity) in 200 μl of buffer (1 mM HEPES-$SO_4$ (pH 7.4), 20 mM $Na_2SO_4$, and 1 mM EDTA) were incubated with or without substrate (FAM-$C_{14}H_{24}O_4$—Cl, at 1.0 mM, final concentration) for 15 minutes at room temperature. Then the reaction mixtures were dialyzed against 20 mM $CH_3COONH_4$ (pH 7.0) overnight at 4° C. and M/Z values of the proteins and protein-substrate complexes determined.

Oligonucleotides employed to prepare DhaA.D 106 mutants include for DhaA.D106C:
5'-CTTGGGTTTGGAAGAGGTCGTCCTGGTCATCCAC TGCTGGGGC-3' (SEQ ID NO:13) and 5'-TGAGCCCCA GCAGTGGATGACCAGGACGACCTCTTCCAAACC-3' (SEQ ID NO:14);
for DhaA.D106Q:
5'-CTTGGGTTTGGAAGAGGTCGTCCTGGTCATCCAC CAGTGGGGC-3' (SEQ ID NO:34) and 5'-TGAGCCCCA CTGGTGGATGACCAGGACGACCTCTTCCAAACC-3' (SEQ ID NO:35);
for DhaA.D106E:
5'-CTTGGGTTTGGAAGAGGTCGTCCTGGTCATCCAC GAATGGGGC-3' (SEQ ID NO:52) and 5'-TGAGC CCCA TTCGTGGATGACCAGGACGACCTCTTCCAAACC-3' (SEQ ID NO:53); and
for DhaA.D106Y:
5'-CTTGGGTTTGGAAGAGGTCGTCCTGGTCATCCAC TACTGGGGC-3' (SEQ ID NO:54) and 5'-TGAGCCCCA GTAGTGGATGACCAGGACGACCTCTTCCAAACC-3' (SEQ ID NO:55). The annealed oligonucleotides contained a Sty' site at the 5' end and the BlpI site at the 3' end. The annealed oligonucleotides were digested with StyI and BlpI and subcloned into GST-DhaA.WT or GST-DhaA.H272F at StyI and BlpI sites. All mutants were confirmed by DNA sequencing.

Results

To confirm that DhaA.H272 mutants were capable of binding Cl-alkanes with functional groups, these mutants or their GST-fusions, as well as the corresponding wild-type proteins or fusions, were contacted with FAM-$C_{14}H_{24}O_4$—Cl, TAMRA-$C_{14}H_{24}O_4$—Cl, ROX.5-$C_{14}H_{24}O_4$—Cl, or biotin-$C_{18}H_{32}O_4$—Cl for 15 minutes at room temperature. Then the proteins were resolved on SDS-PAGE. The gels containing proteins were incubated with FAM-$C_{14}H_{24}O_4$—Cl, TAMRA-$C_{14}H_{24}O_4$—Cl, or ROX.5-$C_{14}H_{24}O_4$—Cl and were analyzed by fluoroimager (Hitachi, Japan) at an $E_{ex}/E_{em}$ appropriate for each fluorophore. Gels containing proteins incubated with biotin-$C_{18}H_{32}O_4$—Cl were transferred to a nitrocellulose membrane and probed with HRP conjugated streptavidin.

Figure 9A:
FIG. 9 shows SDS-PAGE analysis of the binding of wild-type DhaA (lanes 1, 3, and 5 in panel A and lanes 1-8 in panel B) and mutant DhaA (DhaA.H272F); (lanes 2, 4, and 6 in panel A and lanes 9-14 in panel B), to TAMRA-$C_{14}H_{24}O_4$—Cl (lanes 1 and 2 in panel A); ROX—$C_{14}H_{24}O_4$—Cl (lanes 3 and 4 in panel A); FAM-$C_{14}H_{24}O_4$—Cl (lanes 5 and 6 in panel A); or biotin-$C_{18}H_{32}O_4$.Cl (panel B). The concentration of biotin-$C_{18}H_{32}O_4$—Cl in panel B as: 0 μM (lanes 1 and 8), 125 µM (lanes 2 and 9) 25 µM (lanes 3 and 10), 5 µM (lanes 4 and 11), 1 µM (lanes 5 and 12), 0.2 µM (lanes 6 and 13), and 0.04 µM (lanes 7 and 14).
Figure 9B:

As shown in FIG. 9, TAMRA-$C_{14}H_{24}O_4$—Cl (lanes 1 and 2 in panel A), FAM-$C_{14}H_{24}O_4$—Cl (lanes 3 and 4 in panel A), and ROX.5-$C_{14}H_{24}O_4$—Cl (lanes 5 and 6 in panel A) bound to DhaA.H272F (lanes 2, 4 and 6 in panel A) but not to DhaA.WT (lanes 1, 3 and 5 in panel A). Biotin-$C_{18}H_{34}O_4$—Cl bound to DhaA.H272F (lanes 9-14 in panel B) but not to DhaA.WT (lanes 1-8 in panel B). Moreover, the binding of biotin-$C_{18}H_{34}O_4$—Cl to DhaA.H272F (lanes 9-14 in panel B) was dose dependent and could be detected at 0.2 μM. Further, the bond between substrates and DhaA.H272F was very strong, since boiling with SDS did not break the bond.

Figure 10:
FIG. 10 illustrates that pretreatment of a mutant DhaA with a substrate, biotin-$C_{18}H_{32}O_4$—Cl, blocks binding of another substrate. DhaA.WT-lanes 1 and 2; DhaA.H272 mutants: F, lanes 3 and 4; G, lanes 5 and 6; A, lanes 7 and 8; and Q, lanes 9 and 10. Samples 2, 4, 6, 8, and 10 were pretreated with biotin-$C_{18}H_{32}O_4$—Cl.

All tested DhaA.H272 mutants, i.e. H272F/G/A/Q, bound to TAMRA-$C_{14}$—Cl (FIG. 10). Further, the DhaA.H272 mutants bind the substrates in a highly specific manner, since pretreatment of the mutants with one of the substrates (biotin-$C_{18}H_{34}O_4$—Cl) completely blocked the binding of another substrate (TAMRA-$C_{14}H_{24}O_4$—Cl) (FIG. 10).

Figure 11A:
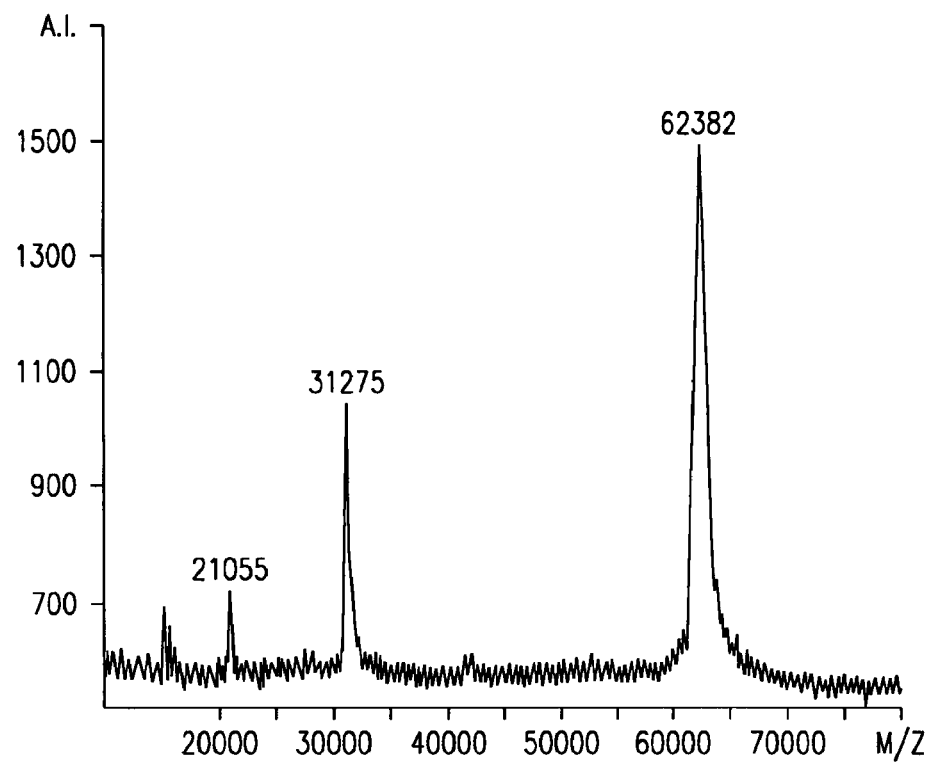
FIG. 11 shows MALDI-TOF analysis of enzyme substrate complexes. Mass spectra of GST-DhaA.WT or GST-DhaA.H272F incubated with FAM-$C_{14}H_{24}O_4$—Cl.
Figure 11B:
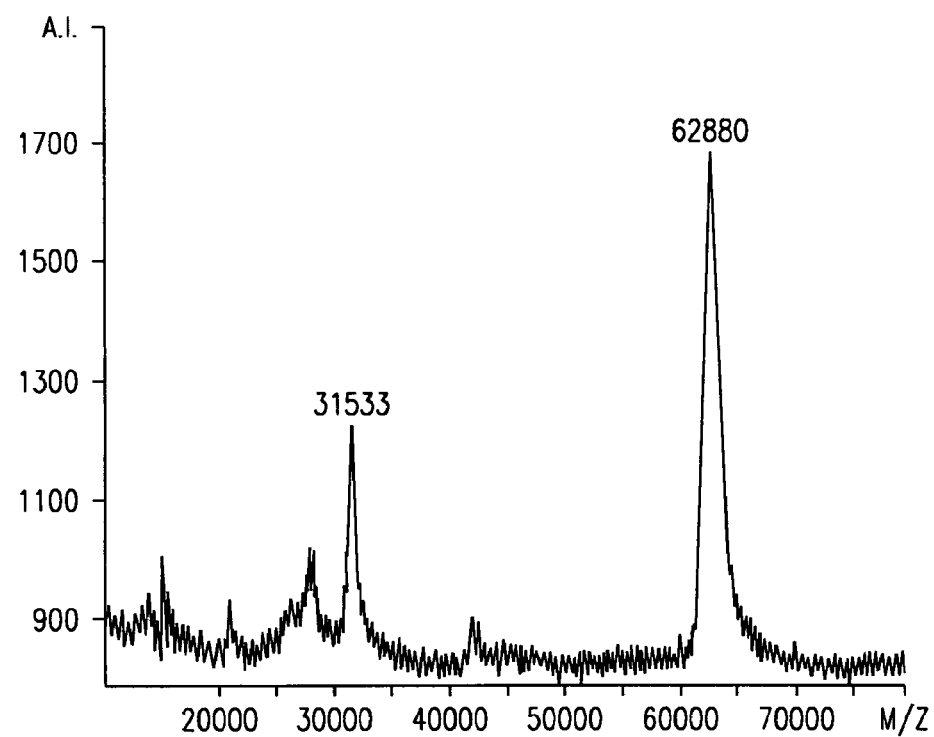

To determine the nature of the bond between Cl-alkanes and the DhaA.H272F mutant (or the GST-DhaA.H272F mutant fusion protein), these proteins were incubated with and without FAM-$C_{14}H_{24}O_4$—Cl, and analyzed by MALDI. As shown in FIG. 11, the bond between mutant DhaA.H272F and FAM-$C_{14}H_{24}O_4$—Cl is strong. Moreover, the analysis of the E*S complex indicated the covalent nature of the bond between the substrate (e.g., FAM-$C_{14}H_{24}O_4$—Cl) and DhaA.H272F. The MALDI-TOF analysis also confirms that the substrate/protein adduct is formed in a 1:1 relationship.

DhaA mutants at another residue in the catalytic triad, residue 106, were prepared. The residue at position 106 in wild-type DhaA is D, one of the known nucleophilic amino acid residues. D at residue 106 in DhaA was substituted with nucleophilic amino acid residues other than D, e.g., C, Y and E, which may form a bond with a substrate which is more stable than the bond formed between wild-type DhaA and the substrate. In particular, cysteine is a known nucleophile in cysteine-based enzymes, and those enzymes are not known to activate water.

SalI sites to the 5' and 3' coding regions, respectively, of phRLuc and to amplify a 900 bp fragment from a phRLuc template (pGL3 vector, Promega). Then, a myristic acid attachment peptide coding sequence was excised with NheI and SalI restriction enzymes and the amplified fragment containing phRLuc was inserted into the NheI/SalI restriction sites of pCIneo.DhaA WT or H272F)-Flag vector. The sequence of each construct was confirmed by DNA sequencing. Promega's TNT® T7Quick system was then used to generate fusion proteins in vitro.

Results

To demonstrate tethering of proteins to a solid support via DhaA.H272F-Cl-alkane bridge, vectors encoding a fusion protein of *Renilla* luciferase (hRLuc, N-terminus of the fusion), a protein connector (17 amino acids, see Table I), and DhaA (WT or H272F mutant) were prepared. The Flag epitope was then fused to the C-terminus of DhaA.

TABLE I

| Fusion | Sequence | Peptide Connector |
|---|---|---|
| GST-DhaA | atcgaaggtcgtgggatccccaggaattcccg ggtcgacgccgcc (SEQ ID NO: 26) | iegrgiprnsrvdaa (SEQ ID NO: 27) |
| GFP-DhaA | tccggatcaagcttgggcgacgaggtggacgg cgggccctctagagccacc (SEQ ID NO: 28) | sgsslgdevdggpsrat (SEQ ID NO: 29) |
| DhaA-Rluc | accggttccggatcaagcttgcggtaccgcgg gccctctagagcc (SEQ ID NO: 30) | tgsgsslryrgpsra (SEQ ID NO: 31) |
| Rluc-DhaA | tccggatcaagcttgcggtaccgcgggccctc tagagccgtcgacgccgcc (SEQ ID NO: 32) | sgsslryrgpsravdaa (SEQ ID NO: 33) |
| DhaA-Flag | Accggt | Tg |

Figure 12:
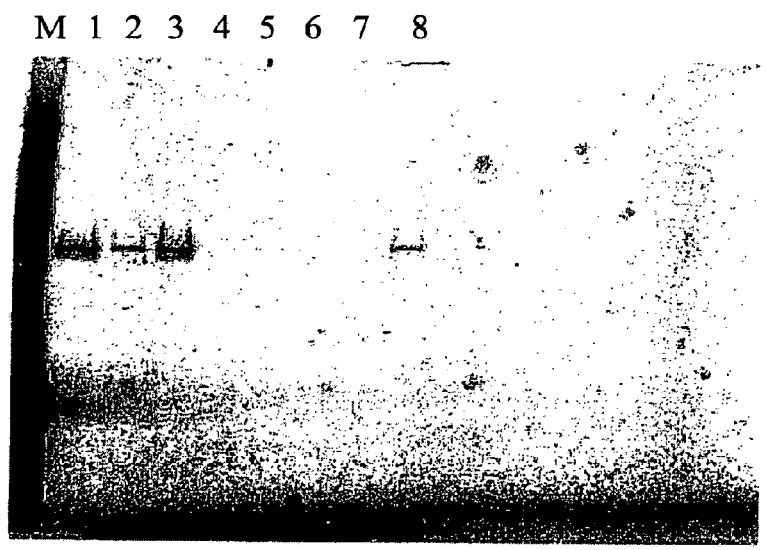
FIG. 12 illustrates SDS-PAGE analysis of the binding properties of DhaA mutants with substitutions at residue 106, and DhaA mutants with substitutions at residue 106 and residue 272, to TAMRA-$C_{14}H_{24}O_4$—Cl. 2 µg of protein and 25 µM TAMRA-$C_{14}H_{24}O_4$—Cl in 32 µl were incubated for one hour at room temperature. 10 µl of each reaction was loaded per lane. Lane 1-DhaA.D106C; lane 2-DhaA.D106C: H272F; lane 3-DhaA.D106E; lane 4-DhaA.D106E:H272F; lane 5-DhaA.D106Q; lane 6-DhaA.D106Q:H272F; lane 7-DhaA.WT; and lane 8-DhaA.H272F. The gel was imaged with a 570 nm filter.

A control mutant, DhaA.D106Q, single mutants DhaA.D106C, DhaA.D106Y, and DhaA.D106E, as well as double mutants DhaA.D106C:H272F, DhaA.D106E:H272F, DhaA.D106Q:H272F, and DhaA.D106Y:H272F were analyzed for binding to TAMRA-$C_{14}H_{24}O_4$—Cl (FIG. 12). As shown in FIG. 12, TAMRA-$C_{14}H_{24}O_4$—Cl bound to DhaA.D106C, DhaA.D106C:H272F, DhaA.D106E, and DhaA.H272F. Thus, the bond formed between TAMRA-$C_{14}H_{24}O_4$—Cl and cysteine or glutamate at residue 106 in a mutant DhaA is stable relative to the bond formed between TAMRA-$C_{14}H_{24}O_4$—Cl and wild-type DhaA. Other substitutions at position 106 alone or in combination with substitutions at other residues in DhaA may yield similar results. Further, certain substitutions at position 106 alone or in combination with substitutions at other residues in DhaA may result in a mutant DhaA that forms a bond with only certain substrates.

EXAMPLE III

Tethering of Luciferase to a Solid Support Via a Mutant DhaA and a Substrate of the Invention Materials and Methods phRLuc-linker-DhaA.WT-Flag and phRLuc-linker-DhaA.H272F-Flag fusion cassettes were constructed by cloning the phRLuc coding region into the NheI/SalI sites of the pCIneo vector which contains a myristic acid attachment peptide coding sequence (MAS). Two primers (5'-GCT-TCACTTGTCGTCATCGTCCTTGTAGTCA-3'; SEQ ID NO:11) and (5'-GCTTCACTTGTCGTCATCGTCCTTG-TAGTCA-3'; SEQ ID NO:12) were designed to add NheI and SDS-PAGE followed by Western blot analysis showed that the proteins had their predicted molecular weights and were recognized by anti-R.Luc and anti-Flag[R] M2 antibodies. In addition, all fusion proteins had *Renilla* luciferase activity (as determined by Promega's *Renilla* Luciferase Assay System in PBS pH 7.4 buffer).

Tethering of proteins to a solid support via a DhaA.H272F-Cl-alkane bridge was shown by using biotin-$C_{18}H_{32}O_4$—Cl as a substrate and streptavidin (SA)-coated 96 well plates (Pierce, USA) as solid support. Translated proteins were contacted with biotin-$C_{18}H_{32}O_4$—Cl substrate at 25 μM (final concentration), for 60 minutes at room temperature. Unbound biotin-$C_{18}H_{32}O_4$—Cl was removed by gel-filtration on Sephadex G-25 prepackaged columns (Amersham Biosciences). Collected fractions of R.Luc-connector-DhaA fusions were placed in SA-coated 96-well plate for 1 hour at room temperature, unbound proteins were washed out and luciferase activity was measured.

Figure 13:
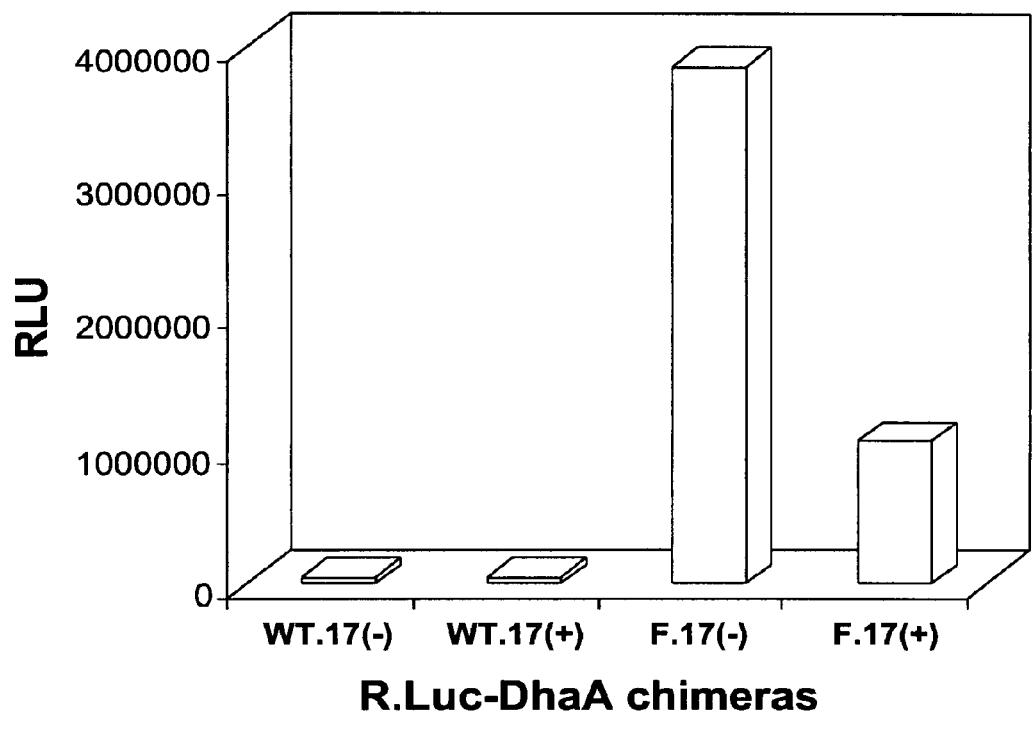
FIG. 13 depicts analysis of *Renilla* luciferase activity in samples having a fusion of luciferase and a mutant DhaA tethered to a solid support (a streptavidin coated plate). Capture of the fusion was accomplished using a substrate of DhaA (i.e., biotin-$C_{18}H_{32}O_4$—Cl). No activity was found in fractions with a fusion of *Renilla* luciferase and wild-type DhaA.

FIG. 13A shows *Renilla* luciferase activity captured on the plate. Analysis of these data indicated that only the fusion containing the mutant DhaA was captured. The efficiency of capturing was very high (more than 50% of *Renilla* luciferase activity added to the plate was captured). In contrast, the efficiency of capturing of fusions containing wild-type DhaA as well as *Renilla* luciferase was negligibly small (<0.1%). Pretreatment of R.Luc-connector-DhaA.H272F with a non-biotinylated substrate (TAMRA-$C_{14}H_{24}O_4$—Cl) decreased the efficiency of capturing by about 80%. Further, there was no effect of pretreatment with a nonbiotinylated substrate on the capturing of the R.Luc-connector-DhaA.WT or *Renilla* luciferase.

Taken together, these data demonstrate that active enzymes (e.g., *Renilla* luciferase) can be tethered to a solid support that forms part of a substrate of the invention (Cl-alkane-DhaA.H272F-bridge), and retain enzymatic activity.

EXAMPLE IV

Mutant DhaA and Substrate System In Vivo

A. Covalent Tethering of Functional Groups to DhaA Mutants In Vivo: in Prokaryotes and Eukaryotes
Materials and Methods To study the binding of a substrate of the invention to a mutant hydrolase expressed in prokaryotes, *E. coli* cells BL21 (λDE3) pLys65 were transformed with pGEX-5X-3.DhaA.WT-Flag or pGEX-5X-3.DhaA.H272F-Flag, grown in liquid culture, and induced with IPTG. Either TAMRA-$C_{14}H_{24}O_4$—Cl or biotin-$C_{18}H_{32}O_4$—Cl was added to the induced cells (final concentration, 25 µM). After 1 hour, cells were harvested, washed with cold PBS (pH 7.3), disrupted by sonication, and fractionated by centrifugation at 19,800×g for 1 hour. Soluble fractions were subjected to SDS-PAGE. Gels with proteins isolated from cells treated with TAMRA-$C_{14}H_{24}O_4$—Cl were analyzed on a fluoroimager, while proteins from cells treated with biotin-$C_{18}H_{32}O_4$—Cl were transferred to a nitrocellulose membrane and probed with HRP-conjugated streptavidin.

To study the binding of TAMRA-$C_{14}H_{24}O_4$—Cl in mammalian cells, DhaA.WT-Flag and DhaA.H272F-Flag coding regions were excised from pGEX-5X-3.DhaA.WT-Flag or pGEX-5X-3.DhaA.H272F-Flag, respectively, gel purified, and inserted into SalI/NotI restriction sites of pCIneo.CMV vector (Promega). The constructs were confirmed by DNA sequencing.

CHO—K1 cells were plated in 24 well plates (Labsystems) and transfected with a pCIneo-CMV.DhaA.WT-Flag or pCIneo-CMV.DhaA.H272F-Flag vector. Twenty-four hours later, media was replaced with fresh media containing 25 µM TAMRA-$C_{14}H_{24}O_4$—Cl and the cells were placed into a $CO_2$ incubator for 60 minutes. Following this incubation, media was removed, cells were quickly washed with PBS (pH 7.4; four consecutive washes: 1.0 ml/cm²; 5 seconds each) and the cells were solubilized in a sample buffer (1% SDS, 10% glycerol, and the like; 250 µl/well). Proteins (10 µl/lane) were resolved on SDS-PAGE (4-20% gradient gels) and the binding of the TAMRA-$C_{14}H_{24}O_4$—Cl was detected by a fluoroimager (Hitachi, Japan) at $E_{ex}/E_{em}$ equal 540/575 nm.
Results FIGS. 14A and B show the binding of biotin-$C_{18}H_{32}O_4$—Cl (A) and TAMRA-$C_{12}H_{24}O_4$—Cl (B) to *E. coli* proteins in vivo. The low molecular band on FIG. 14A is an *E. coli* protein recognizable by HRP-SA, while the fluorescence detected in the bottom part of Panel B was fluorescence of free TAMRA-$C_{12}H_{24}O_4$—Cl. FIG. 15 shows the binding of TAMRA-$C_{12}H_{24}O_4$—Cl to eukaryotic cell proteins in vivo.

Analysis of FIG. 14 and FIG. 15 showed that the DhaA.H272F-Flag mutant but not DhaA.WT-Flag binds TAMRA-$C_{14}H_{24}O_4$—Cl or biotin-$C_{18}H_{32}O_4$—Cl in vivo. Moreover, the bond between DhaA.H272F-Flag and the substrate was very strong (probably covalent), since boiling with SDS followed by SDS-PAGE did not disrupt the bond between the mutant enzyme and the substrate.
B. Permeability of Cell Membrane to Substrates of the Invention
Materials and Methods CHO—K1 Cells (ATCC-CCL61) were cultured in a 1:1 mixture of Ham's F12 nutrients and Dulbecco's modified minimal essential medium supplemented with 10% fetal bovine serum (FBS), 100 U/ml penicillin, and 100 mg/ml streptomycin, in an atmosphere of 95% air and 5% $CO_2$ at 37° C.

To study uptake of different substrates, cells were plated in LT-II chambers (Nunc) or 96 well plates (Labsystems) at a density of 30,000 cells/cm². The following day, media was replaced with media containing different concentrations of the substrates and cells were placed back in a $CO_2$ incubator for 2, 5 or 15 minutes. At the end of the incubation, media containing substrate was removed and cells were quickly washed with PBS (pH 7.4; four consecutive washes: 1.0 ml/cm²; 5 seconds each). Fresh media was then added to cells, and the cells were returned to the $CO_2$ incubator at 37° C. The level of fluorescence in cells in 96 well plates was measured on fluorescent plate reader CytoFluor II (Beckman) at $E_{ex}/E_{em}$ equal 480/520 nm and 540/575 nm for FAM- and TAMRA-modified substrates, respectively. Fluorescent images of the cells were taken on inverted epifluorescent microscope Axiovert-100 (Carl Zeiss) with filter sets appropriate for detection of FITC and TAMRA.
Results As shown in FIG. 16, CHO—K1 cells treated with TAMRA-$C_{14}H_{28}O_4$—Cl (25 µM, 5 minutes at 37° C.) could be quickly and efficiently loaded with TAMRA-$C_{14}H_{28}O_4$—Cl. Image analysis indicated that the fluorescent dye crossed the cell membrane. FIG. 16 also shows that TAMRA-$C_{14}H_{28}O_4$—Cl could be efficiently washed out of the cells. Taken together these data indicate that the plasma membrane of CHO—K1 cells is permeable to TAMRA-$C_{14}H_{28}O_4$—Cl.

In contrast, FAM-$C_{14}H_{24}O_4$—Cl did not cross the plasma membrane of CHO—K1 cells, even when cells were pretreated with FAM-$C_{14}H_{24}O_4$—Cl at high concentrations (i.e., 100 µM) and for much longer periods of time (60 minutes) (data not shown). Thus, the different permeabilities of the cell plasma membrane for various substrates of the invention, e.g., TAMRA-$C_{14}H_{24}O_4$—Cl and FAM-$C_{14}H_{24}O_4$—Cl, provides a unique opportunity to label proteins expressed on the cell surface and proteins expressed inside the cell with different fluorophores, thereby allowing biplexing.

EXAMPLE V

DhaA-based Tethering for Cell Imaging In Vivo

A. Colocalization of GFP and TAMRA-$C_{12}H_{24}O_4$—Cl in Living Mammalian Cells
Materials and Methods A GFP-connector-DhaA fusion cassette was constructed by replacing the *Renilla* luciferase coding region in Packard's vector coding GFP-DEVD-Rluc(h) (Packard #6310066) with DhaA.WT-Flag or DhaA.H272F-Flag coding regions. Two primers (5'-GGAAT GGGCCCTCTAGAGCGACGATGTCA-3'; SEQ ID NO:15, and 5'-CAGTCAGTCACGATGGATCCGCTC AA-3'; SEQ ID NO:16) were designed to add ApaI and BamHI sites (underlined) to the 5' and 3' coding regions of DhaA, respectively, and to amplify a 980 bp fragment from a pGEX-5X-3.DhaA.WT-Flag or pGEX-5X-3.DhaA.H272F-Flag template. The R.Luc coding region was excised with ApaI and BamHI restriction enzymes. Then the 980 bp fragment containing DhaA was inserted into the ApaI/BamHI site of the GFP-DEVD-Rluc(h) coding vector. The sequence of the gene fusion constructs was confirmed by DNA sequencing.

Cells transiently expressing GFP-connector-DhaA.WT-Flag or GFP-connector-DhaA.H272F-Flag fusion proteins were plated in LT-II chambers (Nunc) at a density of 30,000 cells/cm$^2$. The next day, media was replaced with fresh media containing 25 µM of TAMRA-C$_{14}$H$_{24}$O$_4$—Cl and the cells were placed back into in a CO$_2$ incubator for 60 minutes. At the end of the incubation, media containing substrates was removed, cells were quickly washed with PBS (pH 7.4; four consecutive washes: 1.0 ml/cm$^2$; 5 seconds each) and new media was added to the cells. The cells were placed back into in a CO$_2$ incubator and after 60 minutes the cells were quickly washed with PBS (pH 7.4; four consecutive washes: 1.0 ml/cm$^2$; 5 seconds each). Fluorescent images of the cells were taken on inverted epifluorescent microscope Axiovert-100 (Carl Zeiss) with filter sets appropriate for detection of GFP and TAMRA.

Results

As shown by the images in FIG. 17, cells transfected with either GFP-connector-DhaA.WT-Flag or GFP-connector-DhaA.H272F-Flag showed robust expression of the protein(s) with light emitting characteristics of GFP. Analysis of the images of the same cells taken with a TAMRA-filter set showed that cells expressing GFP-connector-DhaA.WT-Flag were dark and could not be distinguished from cells that do not express this fusion protein. In contrast, cells expressing GFP-connector-DhaA.H272F-Flag were very bright and unmistakably recognizable.

Western blot analysis of proteins isolated from CHO—K1 cells transfected with GFP-connector-DhaA.WT-Flag or GFP-connector-DhaA.H272F-Flag vectors showed that these cells expressed proteins that were recognized by an anti-Flag antibody and had the predicted molecular weight for the fusion proteins (data not shown). A fluoroscan of the SDS-PAGE gel with these proteins showed strong/covalent binding of TAMRA to GFP-connector-DhaA.H272F-Flag and no binding to GFP-connector-DhaA.WT-Flag (FIG. 18).

B. Fusion Partners of DhaA in DhaA.WT-Flag and DhaA.H272F-Flag are Functional

To determine whether fusion of two proteins leads to the loss of the activity of one or both proteins, several DhaA-based fusion proteins (see Table II) with DhaA at the C- or N-terminus of the fusion and a connector sequence, e.g., one having 13 to 17 amino acids, between the two proteins, were prepared. The data showed that the functional activity of both proteins in the fusion was preserved.

TABLE II

| N-Terminal protein | Connector | C-terminal protein | Function of protein #1 | Function of protein #2 |
|---|---|---|---|---|
| GST | + | DhaA.H272F | Binding to GSS column | binding |
| GFP | + | DhaA.H272F | Green fluorescence | binding |
| R.Luc | + | DhaA.H272F | hydrolysis of coelenterazine | binding |
| DhaA.H272F | + | R.Luc | Binding | hydrolysis of coelenterazine |
| DhaA.H272F | + | Flag | binding | Recognized by antibody |

C. Toxicity of Cl-Alkanes

Materials and Methods

To study the toxicity of Cl-alkanes, CHO—K1 cells were plated in 96 well plates to a density of 5,000 cells per well. The next day, media was replaced with fresh media containing 0-100 µM concentrations of Cl-alkanes and the cells were placed back into a CO$_2$ incubator for different periods of time. Viability of the cells was measured with CellTiter-Glo™ Luminescence Cell Viability Assay (Promega) according to the manufacturer's protocol. Generally, 100 µl of CellTiter-Glo™ reagent was added directly to the cells and the luminescence was recorded at 10 minutes using a DYNEX MLX microtiter plate luminometer. In some experiments, in order to prevent fluorescence/luminescence interference, the media containing fluorescent Cl-alkanes was removed and the cells were quickly washed with PBS (pH 7.4; four consecutive washes: 1.0 ml/cm$^2$; 5 seconds each) before addition of CellTiter-Glo™ reagent. Control experiments indicated that this procedure had no effect on the sensitivity or accuracy of the CellTiter-Glo™ assay.

Results

Figure 19B:
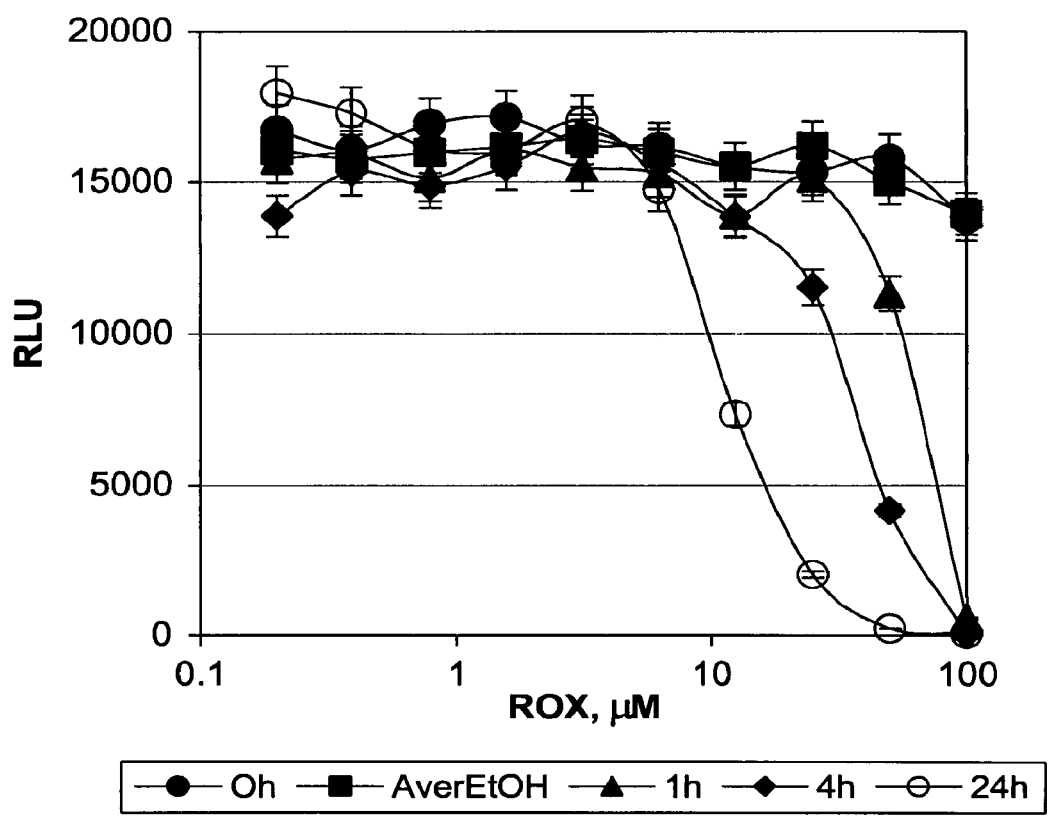
FIG. 19 illustrates the toxicity of selected substrates (panel A, TAMRA and panel B, ROX) for CHO—K1 cells.

As shown in FIG. 19, TAMRA-C$_{14}$H$_{24}$O$_4$—Cl showed no toxicity on CHO—K1 cells even after a 4 hour treatment at a 100 µM concentration the (the highest concentration tested). After a 24 hour treatment, no toxicity was detected at concentrations of 6.25 µM (the "maximum non-toxic concentration"). At concentrations>6.25 µM, the relative luminescence in CHO—K1 cells was reduced in a dose-dependent manner with an IC$_{50}$ of about 100 µM. No toxicity of biotin-C$_{18}$H$_{34}$O$_4$—Cl was observed even after 24 hours of treatment at 100 µM. In contrast, ROX5-C$_{14}$H$_{24}$O$_4$—Cl had a pronounced toxic effect as a reduction of the RLU in CHO—K1 cells could be detected after a 1 hour treatment. The IC$_{50}$ value of this effect was about 75 µM with no apparent ATP reduction at a 25 µM concentration. The IC$_{50}$ value of ROX5-C$_{14}$H$_{24}$O$_4$—Cl toxicity and the "maximum non-toxic concentration" of ROX5-C$_{14}$H$_{24}$O$_4$—Cl decreased in a time-dependent manner reaching 12.5 µM and 6.25 µM, respectively.

D. Detection of DhaA.D106C in CHO Cells Contacted with TAMRA- or DiAc-FAM-containing Substrates and a Fixative CHO cells (ATCC, passage 4) were seeded into 8-well chamber slides (German coverglass system) at low density in DMEM:F12 media (Gibco) containing 10% FBS and 1 mM glutamine (growth media) without antibiotics. Two days later, cells were inspected using an inverted phase microscope. Two visual criteria were confirmed before applying the transfection reagents: 1) the level of cellular confluence per chamber was approximately 60-80%, and 2)>90% of the cells were adherent and showed a flattened morphology. The media was replaced with 150 µl of fresh pre-warmed growth media and cells were incubated for approximately 1 hour.

Cells were transfected using the TransIt TKO system (Miris). The TKO lipid was diluted by adding 7 µl of lipid per 100 µl of serum-free DMEM:F12 media, and then 1.2 µg of transfection-grade DhaA.D106C DNA was added per 100 µl of lipid containing media. The mixture was incubated at room temperature for 15 minutes, and then 25 µl aliquots were transferred into individual culture chambers (0.3 µg DNA). Cells were returned to the incubator for 5-6 hours, washed two times with growth media, 300 µl of fresh growth media was added, and then cells were incubated for an additional 24 hours.

Transfected or non-transfected control cells were incubated with 12.5 µM TAMRA-C$_{14}$H$_{24}$O$_4$—Cl or 12.5 µM DiAc-FAM-C$_{14}$H$_{24}$O$_4$—Cl in 10% FBS/DMEM for 30 minutes at 37° C. and 5% CO$_2$. Cells were washed with warm growth media three times, 300 µl fresh growth media was added, and then cells were incubated for 1 hour.

Growth media was replaced with warm PBS and live cells were visualized using a Zeiss Axiovert 100 inverted microscope equipped with a rhodamine filter set (Exciter filter=540, Emission filter=560 LP) and a fluorescein filter set (Exciter filter=490, Emission filter=520), and a Spot CCD camera. Images were captured with exposure times of 0.15-0.60 seconds at gain settings of 4 or 16.

Discreet and specifically labeled transfected cells were evident in both TAMRA-$C_{14}H_{24}O_4$—Cl and DiAc-FAM-$C_{14}H_{24}O_4$—Cl labeled cells. The majority of cells were non-transfected cells and they did not retain the label.

The PBS was removed and cells were fixed with 3.7% paraformaldehyde/0.1% Triton in PBS for 15 minutes. The fixative was removed, PBS was added, and a second set of images was captured for both TAMRA-$C_{14}H_{24}O_4$—Cl and DiAc-FAM-$C_{14}H_{24}O_4$—Cl labeled cells.

The PBS was replaced with 50% methanol in PBS and cells were incubated for 15 minutes, followed by a 15 minute incubation in 95% methanol. A third set of images was captured and then an equal volume mixture of methanol and acetone was applied to the cells and incubated for 15 minutes. The media was replaced with PBS and a fourth set of images was collected.

Results suggested that the binding of the substrates to the DhaA.D106C mutant was stable following fixation with paraformaldehyde and subsequent processing of fixed cell samples in methanol and acetone. Furthermore, the brightness of the TAMRA or FAM fluorescence was unchanged under these conditions.

EXAMPLE VI

Mutant Beta-Lactamase (blaZ)-based Tethering

The serine-β-lactamases, enzymes that confer bacterial resistance to β-lactam antibiotic, likely use the hydroxyl group of a serine residue (Ser70 in the class A consensus numbering scheme of Ambler et al. (1991)) to degrade a wide range of β-lactam compounds. The reaction begins with the formation of a precovalent encounter complex (FIG. 20A), and moves through a high-energy acylation tetrahedral intermediate (FIG. 20B) to form a transiently stable acyl-enzyme intermediate, forming an ester through the catalytic residue Ser70 (FIG. 20C). Subsequently, the acyl-enzyme is attacked by hydrolytic water (FIG. 20D) to form a high-energy deacylation intermediate (FIG. 20E) (Minasov et al., 2002), which collapses to form the hydrolyzed product (FIG. 20F). The product is then expelled, regenerating free enzyme. As in serine proteases, this mechanism requires a catalytic base to activate the serine nucleophile to attack the amide bond of the substrate and, following formation of the acyl-enzyme intermediate, to activate the hydrolytic water for attack on the ester center of the adduct.

A. Mutant β-Lactamase and Fusions Thereof

Materials and Methods

The plasmid pTS32 harboring *Staphylococcus aureus* PC1 blaZ gene (Zawadzke et al., 1995) was kindly provided by Dr. O. Herzberg (University of Maryland Biotechnology Institute). The blaZ gene has the following sequence:

```
                                           (SEQ ID NO: 36)
AGCTTACTAT GCCATTATTA ATAACTTAGC CATTTCAACA

CCTTCTTTCA AATATTTATAATAAACTATT GACACCGATA

TTACAATTGT AATATTATTG ATTTATAAAA

ATTACAACTGTAATATCGGA GGGTTTATTT TGAAAAAGTT

AATATTTTTA ATTGTAATTG CTTTAGTTTTAAGTGCATGT

AATTCAAACA GTTCACATGC CAAAGAGTTA AATGATTTAG

AAAAAAAATATAATGCTCAT ATTGGTGTTT ATGCTTTAGA

-continued
TACTAAAAGT GGGTAAGGAAG TAAAATTTAATTCAGATAAG

AGATTTGCCT ATGCTTCAAC TTCAAAAGCG ATAAATAGTG

CTATTTTGTTAGAACAAGTA CCTTATAATA AGTTAAATAA

AAAAGTACAT ATTAACAAAG ATGATATAGTTGCTTATTCT

CCTATTTTAG AAAAATATGT AGGAAAAGAT ATCACTTTAA

AAGCACTTATTGAGGCTTCA ATGACATATA GTGATAATAC

AGCAAACAAT AAAATTATAA AAGAAATCGGTGGAATCAAA

AAAGTTAAAC AACGTCTAAA AGAACTAGGA GATAAAGTAA

CAAATCCAGTTAGATATGAG ATAGAATTAA ATTACTATTC

ACCAAAGAGC AAAAAAGATA CTTCAACACCTGCTGCCTTC

GGTAAGACCC TTAATAAACT TATCGCCAAT GGAAAATTAA

GCAAAGAAACAAAAAATTC TTACTTGATT TAATGTTAAA

TAATAAAAGC GGGAGATACTT TAATTAAAGACGGTGTTCCA

AAAGACTATA AGGTTGCTGA TAAAAGTGGT CAAGCAATAA

CATATGCTTCTAGAAATGAT GTTGCTTTTG TTTATCCTAA

GGGCCAATCT GAACCTATTG TTTTAGTCATTTTTACGAAT

AAAGACAATA AAAGTGATAA GCCAAATGAT AAGTTGATAA

GTGAAACCGCCAAGAGTGTA ATGAAGGAAT TTTAATATTC

TAAATGCATA ATAAATACTG ATAACATCTTATATTTTGTA

TTATATTTTG TATTATCGTT GAC.
```

GST-blaZ (WT and E166D, N170Q, or E166D:N170Q mutants) fusion cassettes were constructed by introducing point mutations into the blaZ gene and cloning the blaZ coding regions into SalI/AgeI sites of pGEX5x3 vector. The internal mutagenic primers were as follows: E166D (5'-CCAGTTAGATATGACATAGAATTAAAT-TACTATTCACC-3', SEQ ID NO:56; 5'-GGTGAATAG-TAATTTAATTCTATGTCATATCTAACTGG-3', SEQ ID NO:57); N170Q (5'-CCAGTTAGATATGAGATAGAATTA-CAGTACTATTCACC-3', SEQ ID NO:58; and 5'-GGT-GAATAGTACTGTAATTCTATCTCATATCTAACTGG-3', SEQ ID NO:59); and E166D:N170Q (5'CCAGTTAGATAT-GACATAGAATTACAGTACTATTCACC-3'; SEQ ID NO:60 and 5'-GGTGAATAGTACTGTAATTCTATGT-CATATCTAACTGG-3; SEQ ID NO:61). Two external primers (5'-CAACAGGTCGACGCCGCCATGAAAGAGT-TAAATGATTTAG-3', SEQ ID NO:62; and 5'-GTAGTCACCGGTAAATTCCTTCATTA-CACTCTTGGC-3', SEQ ID NO:63) were designed to add N-terminal SalI site and a Kozak sequence to the 5' coding region, add an AgeI site to the 3' coding regions of blaZ, and to amplify a 806 bp fragment from a blaZ.WT template. The resulting fragment was inserted into the SalI/AgeI site of the vector pGEX-5X-3 containing a glutathione S-transferase (GST) gene, a sequence coding a Factor Xa cleavage site, and multiple cloning sites (MCS) followed by a sequence coding for Flag and stop codons. These gene fusion constructs were confirmed by DNA sequencing.

The GST-blaZ (WT or mutants) fusion proteins were over-expressed in competent *E. coli* BL21 (λDE3) cells and purified essentially as described for DhaA and GST-DhaA fusion proteins (except the potassium phosphate buffer (0.1 M, pH 6.8) was used instead of Buffer A). Homogeneity of the proteins was verified by SDS-PAGE.

The chromogenic substrate 6-β-[(Furylacryloyl)amido] penicillanic acid triethylamine salt (FAP) was purchased from Calbiochem (La Jolla, Calif.). Hydrolysis of FAP was monitored by loss of absorbance at 344 nm (deltaE=1330 $M^{-1}$ $cm^{-1}$) on a Beckman Du640 spectrophotometer (Beckman Coulter, Fullerton, Calif.). All assays were performed at 25° C. in 0.1 M potassium phosphate buffer at pH 6.8.

In CCF2, the cephalosporin core links a 7-hydroxycoumarin to a fluorescein. In the intact molecule, excitation of the coumarin ($E_{ex}$—409 nm) results in FRET to the fluorescein, which emits green light ($E_{em}$—520 nm). Cleavage of CCF2 by β-lactamase results in spatial separation of the two dyes, disrupting FRET such that excitation of coumarin now gives rise to blue fluorescence ($E_{ex}$—447 nm). CCF2 was purchased from Aurora Biosciences Corporation (San Diego, Calif.). Reduction of the FRET signal and an increase in blue fluorescence were measured on Fluorescence Multi-well Plate Reader CytoFluorII (PerSeptive Biosystems, Framingham, Mass., USA).

Results

All β-lactamases, including β-lactamase from *Staphylococcus aureus* PC1, hydrolyze β-lactams of different chemical structure. The efficiency of hydrolysis depends on the type of the enzyme and chemical structure of the substrate. Penicillin is considered to be a preferred substrate for β-lactamase from *Staphylococcus aureus* PC1.

Figure 20:
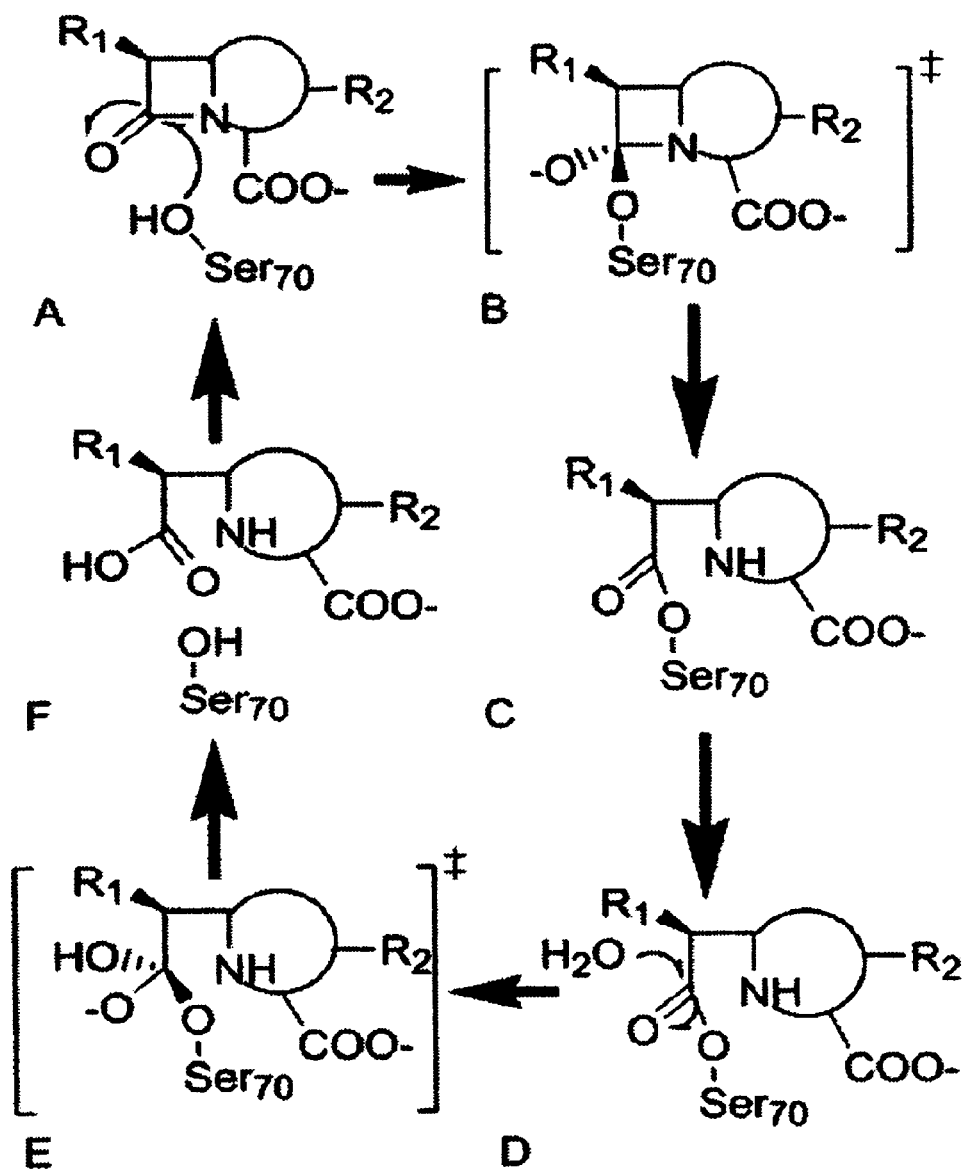
FIG. 20 illustrates a reaction scheme for a serine beta-lactamase. The reaction begins with the formation of a pre-covalent encounter complex (FIG. 20A), and moves through a high-energy acylation tetrahedral intermediate (FIG. 20B) to form a transiently stable acyl-enzyme intermediate, forming an ester through the catalytic residue Ser70 (FIG. 20C). Subsequently, the acyl-enzyme is attacked by hydrolytic water (FIG. 20D) to form a high-energy deacylation intermediate (FIG. 20E) (Minasov et al., 2002), which collapses to form the hydrolyzed product (FIG. 20F). The product is then expelled, regenerating free enzyme.
Figure 21:
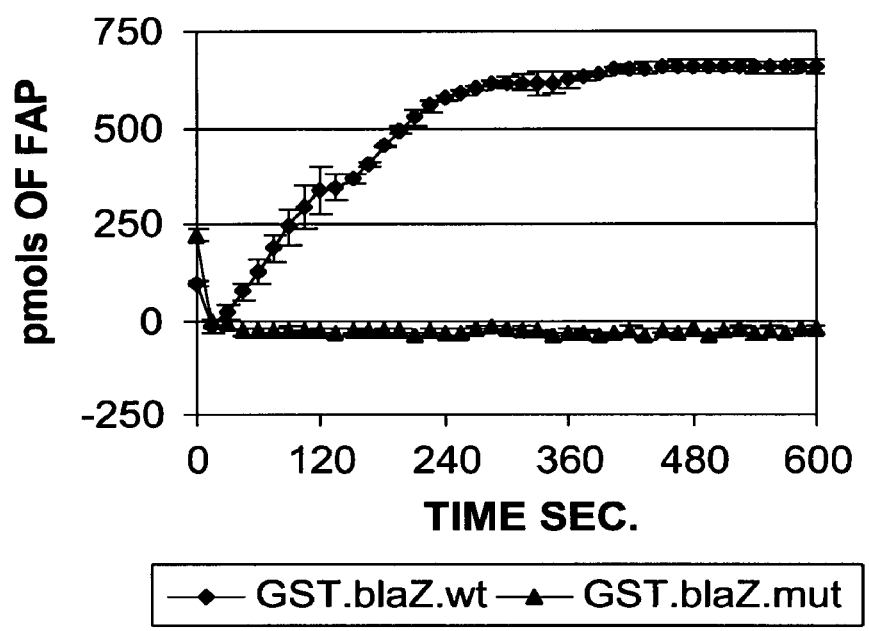
FIG. 21 shows hydrolysis of FAP by GST-blaZ over time.

The effect of point mutation(s) on the ability of β-lactamase to hydrolyze penicillins was studied as described in Zawadzke et al. (1995). As shown in FIG. 20, a GST-β-lactamase PC1 fusion protein efficiently hydrolyzed FAP. Hydrolysis of FAP by blaZ.E166D, blaZ.N170Q or blaZ.E166D:N170Q blaZ mutants could not be detected even after 60 minutes of co-incubation. Therefore, these mutations lead to significant inactivation of blaZ.

To show that blaZ.E166D, blaZ.N170Q, or blaZ.E166D: N170Q mutants bind β-lactams, and therefore different functional groups could be tethered to these proteins via β-lactams, GST fusions of these mutants were incubated with BOCELLIN™ FL, a fluorescent penicillin (Molecular Probes Inc., Eugene, Oreg.). Proteins were resolved on SDS-PAGE and analyzed on fluoroimager (Hitachi, Japan) at an $E_{ex}/E_{em}$ appropriate for the particular fluorophore. The data in FIG. 22 show that all blaZ mutants bind bocellin. Moreover, the bond between blaZ mutants and fluorescent substrates was very strong, and probably covalent, since boiling with SDS followed by SDS-PAGE did not disrupt the bond. Also, the binding efficiency of double mutant blaZ.E166D:N170Q (judged by the strength of the fluorescent signal of protein-bound fluorophore) was much higher than binding efficiency of either of the single mutants, and the binding efficiency of blaZ.N170Q was higher than binding efficiency of blaZ.E166D. These data, in combination with current understanding of the role of the individual amino acids in hydrolysis of beta-lactams, show that additional mutations (e.g., a mutation of an auxiliary amino acid) can improve efficiency of tethering of functional groups to a mutated protein.

The effect of point mutation(s) on the ability of β-lactamase to hydrolyze cephalosporins was also studied using CCF2, a FRET-based substrate described by Zlokarnik et al. (1998). As shown in FIG. 23, the GST-β-lactamase PC1 fusion protein efficiently hydrolyzed CCF2 (lane 2). Single point mutations (i.e., E166D or N170Q) reduced the ability of the fusion proteins to hydrolyze CCF2 (lanes 3 and 4). The replacement of two amino acids (blaZ.E166D:N170Q mutants, lane 5) had an even more pronounced effect on the CCF2 hydrolysis. However, all blaZ mutants were capable of hydrolyzing CCF2.

Thus, an amino acid substitution at position 166 or 170, e.g., Glu166Asp or Asn170Gly enables the mutant beta-lactamase to trap a substrate and therefore tether the functional group of the substrate to the mutant beta-lactamase via a stable, e.g., covalent, bond. Moreover, mutation of an amino acid that has an auxiliary effect on $H_2O$ activation increased the efficiency of tethering.

EXAMPLE VII

Targeting of DhaA.H272F to the Nucleus and Cytosol of Living Cells

Materials and Methods

A GFP-connector-DhaA.H272F-NLS3 fusion cassette was constructed by inserting a sequence encoding NLS3 (three tandem repeats of the Nuclear Localization Sequence (NLS) from simian virus large T-antigen) into the AgeI/BamHI sites of a pCIneo.GFP-connector-DhaA.H272F-Flag vector. Two complementary oligonucleotides (5'-CCGGT-GATCCAAAAAAGAAGAGAAAGGTAGATC-CAAAAAAGAAGAGAA AGGTAGATCCAAAAAA-GAAGAGAAAGGTATGAG-3', sense, SEQ ID NO:37, and 5'-GATCCTCATACCTTTCTCTTCTTTTTTG-GATCTACCTTTCTCTTCTTTTTTG GATCTAC-CTTTCTCTTCTTTTTTGGATCA-3', antisense, SEQ ID NO:38) coding for the NLS3 peptide, were annealed. The annealed DNA had an AgeI site at 5' end and a BamHI site at the 3' end. The annealed DNA was subcloned into the GFP-connector-DhaA.H272F-Flag construct at the AgeI/BamHI sites. The sequence of the gene fusion construct was confirmed by DNA sequencing.

A DhaA.H272F-β-arrestin2 fusion cassette was constructed by replacing the pGFP² coding region in Packard's vector encoding GFP²-β-arrestin2 (Packard #6310176-1F1) with the DhaA.H272F-Flag coding region. Two primers (5'-ATTATGCTGAGTGATATCCC-3'; SEQ ID NO:39, and 5'-CTCGGTACCAAGCTCCTTGTAGTCA-3'; SEQ ID NO:40) were designed to add a KpnI site to the 3' coding region of DhaA, and to amplify a 930 bp fragment from a pGEX5X-3.DhaA.H272F-Flag template. The pGFP² coding region was excised with NheI and KpnI restriction enzymes, then the 930 bp fragment containing encoding DhaA.H272F was inserted into the NheI and KpnI sites of the GFP²-β-arrestin2 coding vector. The sequence of the fusion construct was confirmed by DNA sequencing.

CHO—K1 or 3T3 cells transiently expressing GFP-connector-DhaA.H272F-NLS3, GFP²-β-arrestin2 or DhaA.H272F-β-arrestin2 fusion proteins were plated in LT-II chambers (Nunc) at a density of 30,000 cells/$cm^2$. The next day, media was replaced with fresh media containing 25 μM of TAMRA-$C_{14}H_{24}O_4$—Cl and the cells were placed back into a $CO_2$ incubator for 60 minutes. At the end of the incubation, substrate media was removed, cells were quickly washed with PBS (pH 7.4; four consecutive washes: 1.0 ml/$cm^2$; 5 seconds each), and new media was added to the cells. The cells were placed back into a $CO_2$ incubator and after 60 minutes the cells were quickly washed with PBS (pH 7.4; 1.0 ml/$cm^2$). Fluorescent images of the cells were taken on confocal microscope Pascal-5 (Carl Zeiss) with filter sets appropriate for the detection of GFP and TAMRA.

Results

As shown by the images in FIG. 24, GFP and TAMRA were co-localized in the cell nucleus of cells expression GFP-connector-DhaA.H272F-NLS3 and contacted with TAMRA-$C_{14}H_{24}O_4$—Cl.

As shown by the images in FIG. 25, GFP-β-arrestin2 expressing cells have a typical β-anestin2 cytosolic localization. A fluoroscan of the SDS-PAGE gel of DhaA.H272F-β-arresting showed strong binding of a TAMRA containing DhaA substrate to cells expressing DhaA.H272F-β-arrestin2.

EXAMPLE VIII

Site-Directed Mutagenesis of DhaA Catalytic Residue 130

Haloalkane dehalogenases use a three-step mechanism for cleavage of the carbon-halogen bond. This reaction is catalyzed by a triad of amino acid residues composed of a nucleophile, base and acid which, for the haloalkane dehalogenase from *Xanthobacter autotrophicus* (DhlA), are residues Asp124, His289 and Asp260, respectively (Franken et al., 1991), and in *Rhodococcus* dehalogenase enzyme (DhaA), Asp106, His272 and Glu130 (Newman et al., 1999).

Unlike the haloalkane dehalogenase nucleophile and base residues, the role of the third member of the catalytic triad is not yet fully understood. The catalytic acid is hydrogen bonded to the catalytic His residue and may assist the His residue in its function by increasing the basicity of nitrogen in the imidazole ring. Krooshof et al. (1997), using site-directed mutagenesis to study the role of the DhlA catalytic acid Asp260, demonstrated that a D260N mutant was catalytically inactive. Furthermore, this residue apparently had an important structural role since the mutant protein accumulated mainly in inclusion bodies. The haloalkane dehalogenase from *Sphinogomonas paucimobilis* (LinB) is the enzyme involved in γ-hexachlorocyclohexane degradation (Nagata et al., 1997). Hynkova et al., (1999) replaced the putative catalytic residue (Glu-132) of the LinB with glutamine (Q) residue. However, no activity was observed for the E132Q mutant even at very high substrate concentrations.

To examine the role of the DhaA catalytic triad acid Glu130 in protein production and on the ability of the mutant protein to form covalent alkyl-enzyme intermediates with a fluorescent-labeled haloalkane substrate, site-directed mutagenesis was employed to replace the DhaA glutamate (E) residue at position 130 with glutamine, leucine and alanine.

Materials and Methods

Strains and plasmids. Ultracompetent *E. coli* XL10 Gold (Stratagene; Tet$^r$ Δ(mcrA)183 Δ(mcrCB-hsdSMR-mrr)173 endA1 supE44 thi-1 recA1 gyrA96 relA1 lac Hte [F' proAB lacI$^q$ZΔM15 Tn10 (Tet$^r$) Amy Cam$^r$]) was used to as a host in transformation of site-directed mutagenesis reactions. *E. coli* strain JM109 (e14-(McrA-) recA1 endA1 gyrA96 thi-1 hsdR17(rK– mK+) supE44 relA1 Δ(lac-proAB) [F' traD36 proAB lacI$^q$ZΔM15]) was used as the host for gene expression and whole cell enzyme labeling studies. A GST-DhaA-FLAG gene fusion cloned into plasmid pGEX5X3, designated pGEX5X3DhaAWT.FLAG, was used as the starting template for E130 mutagenesis. A mutant plasmid containing a H272F mutation in DhaA, designated pGEX5X3DhaAH272F-FLAG, was used as a positive control in labeling studies and the cloning vector pGEX5X3 was used as a negative control.

Site-directed Mutagenesis of the DhaA E130 Residue. The sequence of the oligonucleotides used for mutagenesis is shown below. The underlined nucleotides indicate the position of the altered codons. The oligonucleotides were synthesized by Integrated DNA Technologies (Coralville, Iowa) at the 100 nmole scale and modified by phosphorylation at the 5' end.

DhaA E130Q
(SEQ ID NO: 41)
5' CAAAGGTATTGCATGTATG<u>CAG</u>TTCATCCGGCCTATCCCG 3'

DhaA E130L
(SEQ ID NO: 42)
5' GTCAAAGGTATTGCATGTATG<u>CTG</u>TTCATCCGGCCTATCCCGAC 3'

DhaA E130A
(SEQ ID NO: 43)
5' AGGTATTGCATGTATG<u>GCG</u>TTCATCCGGCCTATCCC 3'

Site-directed mutagenesis was performed using the QuikChange Multi kit according to the manufacturer's instructions (Stratagene, La Jolla, Calif.). The mutagenesis reactions were introduced into competent *E. coli* XL10 Gold cells and transformants were selected on LB agar plates containing ampicillin (100 µg/mL). Plasmid DNA isolated from individual transformants was initially screened for the loss of an EcoRI site due to replacement of the glutamate codon (GAAttc). Clones suspected of containing the desired codon change from each reaction were selected and subjected to DNA sequence analysis (SeqWright, Houston, Tex.). The primer used to confirm the sequence of the mutants in the pGEX5X3 vector was as follows: 5' GGGCTGGCAAGC-CACGTTTGGTG 3' (SEQ ID NO:44).

DhaA Mutant Analysis. The three DhaA E130 substitution mutants were compared to the following constructs: Wild-type DhaA, DhaA.H272F, and a DhaA negative control (pGEX5X3 vector only). Overnight cultures of each clone were grown in 2 mL of LB containing ampicillin (100 µg/mL) by shaking at 30° C. The overnight cultures were diluted 1:50 into a sterile flask containing 50 mL fresh LB medium and ampicillin (100 µg/mL). The cultures were incubated with shaking at 25° C. to minimize the production of insoluble protein species. When the cultures reached mid-log phase ($OD_{600}$=0.6), IPTG (0.1 mM) was added and the cultures were incubated with shaking at 25° C. for an additional 22 hours. For labeling of whole cells with a tetramethyl-rhodamine (TAMRA) haloalkane conjugated substrate, the cell density of each culture was adjusted to $OD_{600}$=1 prior to adding substrate to a concentration of 15 µM. The cells were incubated with gentle agitation at 4° C. for approximately 18 hours. Following incubation, 20 µl of cells from each labeling reaction was added to 6 µl of 4×SDS loading dye and the samples were boiled for about 3 minutes prior to being loaded onto a 4-20% acrylamide gel (Tris glycine). For in vitro labeling studies, crude lysates of IPTG induced cultures were prepared by collecting 3 mL of cells ($OD_{600}$=1) and resuspending the resulting pellet in 75 µL PBS. Following a freeze/thaw step, 225 µL of 1× Cell Culture Lysis Reagent (Promega Corp., Madison, Wis.) containing 1.25 mg/mL lysozyme was added to facilitate lysis of the cells. A 20 µL sample of each lysate was combined with 25 µL of 1×PBS. The TAMRA labeled haloalkane substrate was added to a final concentration of 25 µM. The labeling reactions were incubated at room temperature for 2 hours. A 25 µl sample of each reaction was added to 6 µl of 4×SDS loading dye and the samples were boiled for about 3 minutes prior to being loaded onto a 4-20% acrylamide gel (Tris glycine). The gels were imaged using a FluorImager SI instrument (Amersham Biosciences, Piscataway, N.J.) set to detect emission at 570 nm.

Cell-free lysates were generated by centrifugation of crude lysates for 15 minutes at 14,000 RPM. Protein production was monitored by SDS-PAGE and Western blot analysis. Proteins transferred to a PVDF membrane were incubated with an anti-FLAG$^R$ antibody conjugated with alkaline phosphatase (AP) (Sigma, St. Louis, Mo.). The blot was developed with the Western Blue stabilized substrate for alkaline phosphatase (Promega Corp., Madison, Wis.).

Results

Figure 26:
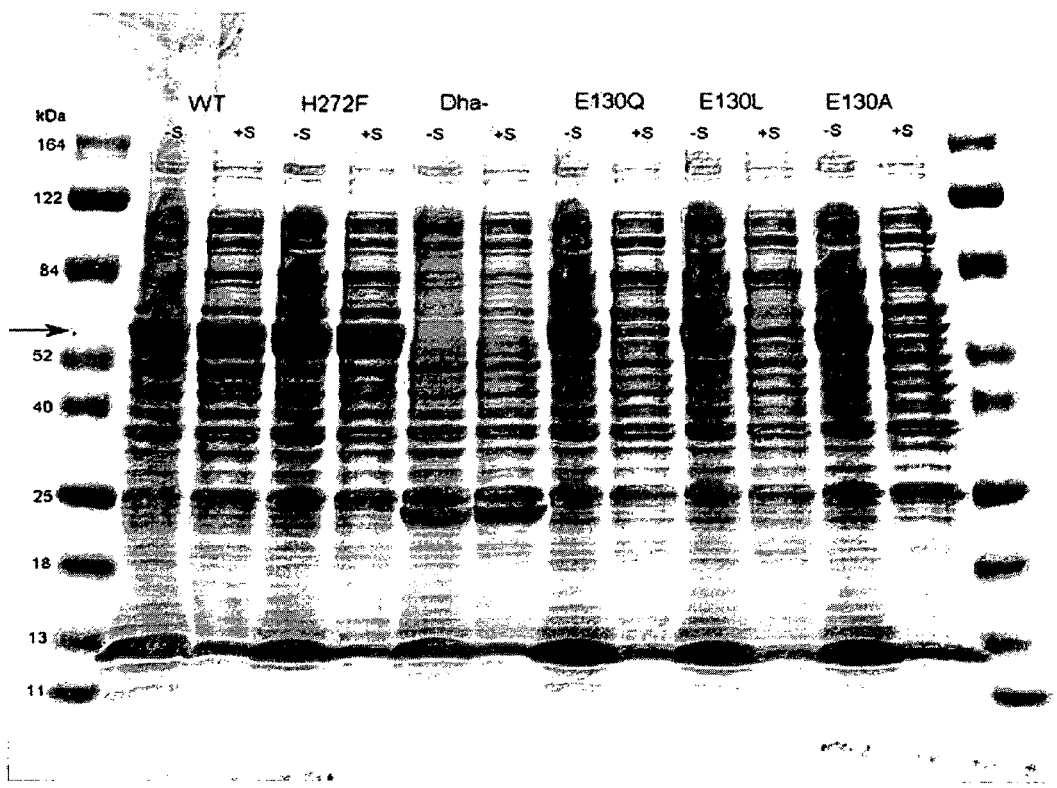
FIG. 26 shows an SDS-PAGE analysis of DhaA expression in *E. coli*. Lanes: 1, Molecular weight standards; 2, Wild-type DhaA crude lysate; 3, Wild-type DhaA cell-free lysate; 4, DhaA.H272F crude lysate; 5, DhaA.H272F cell-free lysate; 6, vector control crude lysate; 7, vector control cell-free lysate; 8, DhaA.E130Q C1 mutant crude lysate; 9, DhaA.E130Q C1 mutant cell-free lysate; 10, DhaA.E130L A5 mutant crude lysate; 11, DhaA.E130L A5 mutant cell-free lysate; 12, DhaA.E130A A12 mutant crude lysate; 13, DhaA.E130A A12 mutant cell-free lysate; 14, Molecular weight standards. The arrow indicates the location of the DhaA protein. −s, lysate before centrifugation; +s, lysate after centrifugation.
Figure 27:
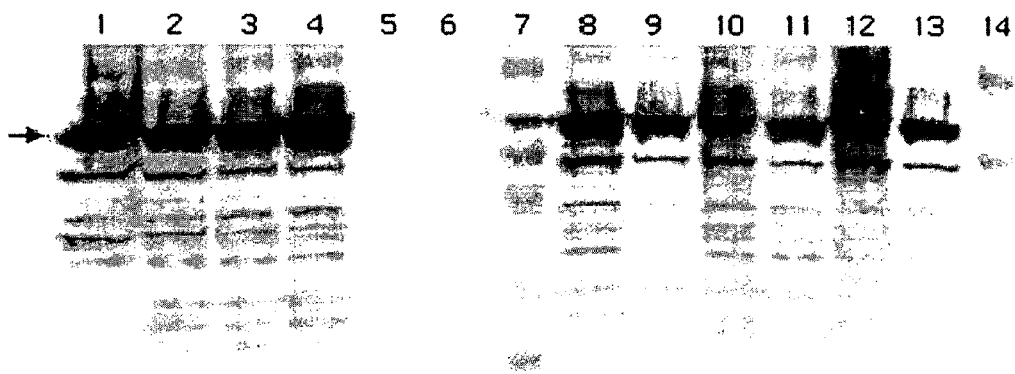
FIG. 27 shows an immunoblot analysis of DhaA containing lysates. Lanes: 1, Wild-type DhaA crude lysate; 2, Wild-type DhaA cell-free lysate; 3, DhaA.H272F crude lysate; 4, DhaA.H272F cell-free lysate; 5, vector control crude lysate; 6, vector control cell-free lysate; 7, Molecular weight standards; 8, DhaA.E130Q C1 mutant crude lysate; 9, DhaA.E130Q C1 mutant cell-free lysate; 10, DhaA.E130L A5 mutant crude lysate; 11, DhaA.E130L A5 mutant cell-free lysate; 12, DhaA.E130A A12 mutant crude lysate; 13, DhaA.E130A A12 mutant cell-free lysate; 14, Molecular weight standards. The arrow indicates the location of the DhaA protein.

The role of the DhaA catalytic acid in the hydrolysis of the alkyl-enzyme intermediate was probed by site-directed mutagenesis. The DhaA codon E130 was replaced with a codon for glutamine (Q), leucine (L) or alanine (A), as these substitutions would likely be least disruptive to the structure of the enzyme. Following mutagenesis, restriction endonuclease screening and DNA sequence analysis was used to verify the desired codon changes. Sequence verified DhaA.E130Q, DhaA.E130L and DhaA.E130A clones, designated C1, A5 and A12, respectively, were chosen for further analysis. The E130 mutants were analyzed for protein expression and for their ability to form a covalent alkyl-enzyme intermediate with a TAMRA labeled haloalkane substrate. The three E130 gene variants were over-expressed in E. coli JM109 cells following induction with IPTG. SDS-PAGE analysis of crude cell lysates showed that cultures expressing the wild-type and mutant dhaA genes accumulated protein to approximately the same level (FIG. 26; lanes 2, 4, 6, 8, 10, and 12). Furthermore, the DhaA protein that was produced by the wild-type and H272F constructs was for the most part soluble since the amount of protein did not change appreciably after centrifugation (FIG. 26; lanes 3 and 5). The abundant 22 kDa protein bands present in the vector only lanes (FIG. 26; lanes 6 and 7) represented the GST protein. These results, however, are in stark contrast to the DhaA.E130Q, DhaA.E130L and DhaA.E130A mutants that appeared to accumulate predominantly insoluble DhaA protein. This conclusion is based on the observation that after centrifugation, there was a significant loss in the amount of DhaA protein present in cell-free lysates (FIG. 26; lanes 9, 11, and 13). Nevertheless, a protein band that comigrates with DhaA was clearly observed in each DhaA.E130 mutant lanes after centrifugation (+s) suggesting the presence of soluble enzyme. Western analysis was, therefore, used to determine if the protein bands observed in the DhaA.E130 mutants following centrifugation represented soluble DhaA material. The immunoblot shown in FIG. 27 confirmed the presence of soluble DhaA protein in each of the DhaA.E130 mutant cell-free lysates (lanes 9, 11, and 13).

Figure 28:
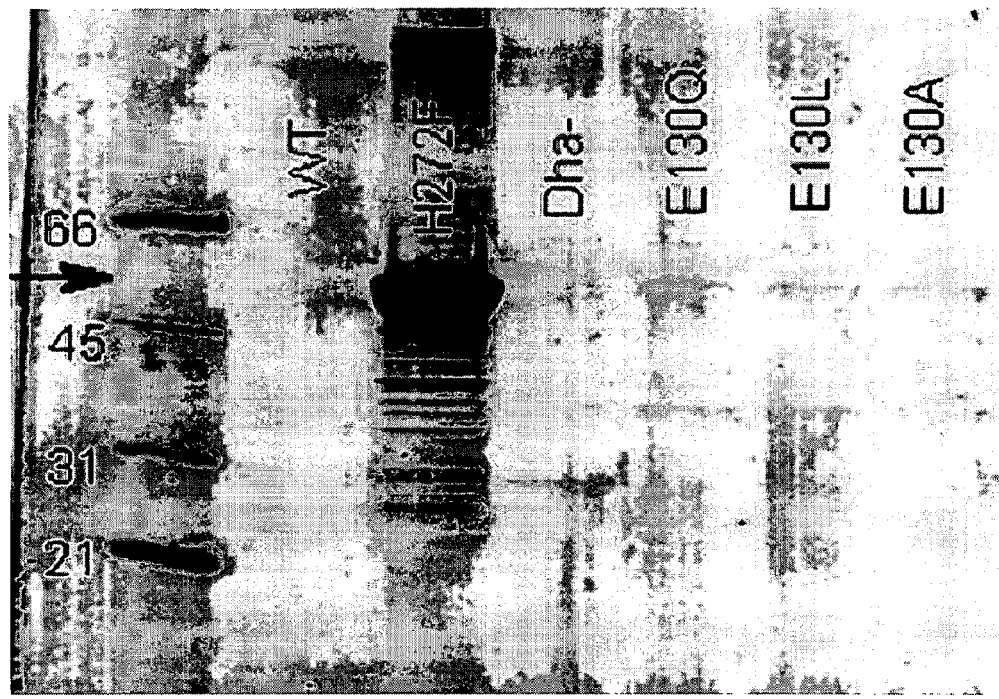
FIG. 28 provides fluoroimage analysis of in vitro covalent alkyl-enzyme formation. Lanes: 1, Fluorescent molecular weight standards; 2, DhaA wild-type; 3, DhaA.H272F mutant; 4, DhaA− (vector only control); 5, DhaA.E130Q mutant; 6, DhaA.E130L mutant; 7, DhaA.E130A mutant. The arrow indicates the location of the fluorescent enzyme-alkyl covalent intermediate.

The DhaA.E130 mutants were also examined for their ability to generate an alkyl-enzyme covalent intermediate. Crude lysates prepared from IPTG induced cultures of the various constructs were incubated in the presence of the TAMRA labeled substrate. FIG. 28 showed that the DhaA.H272F mutant (lane 3) was very efficient at producing this intermediate. No such product could be detected with either the WT DhaA or negative control lysates. Upon initial examination, the DhaA.E130 mutants did not appear to produce detectable levels of the covalent product. However, upon closer inspection of the fluoroimage extremely faint bands were observed that could potentially represent minute amounts of the covalent intermediate (FIG. 28; lanes 5-7). Based on these results, the ability of whole cells to generate a covalent, fluorescent alkyl-enzyme intermediate was investigated.

Figure 29:
FIG. 29 provides fluoroimage analysis of covalent alkyl-enzyme formation in whole cells. Lanes: 1, Fluorescent molecular weight standards; 2, DhaA wild-type; 3, DhaA.H272F mutant; 4, DhaA– (vector only control); 5, DhaA.E130Q mutant; 6, DhaA.E130L mutant; 7, DhaA.E130A mutant; 8, Fluorescent molecular weight standards. The arrow indicates the location of the fluorescent enzyme-alkyl covalent intermediate.

FIG. 29 shows the results of an in vivo labeling experiment comparing each of the DhaA.E130 mutants with positive (DhaA.H272F mutant) and negative (DhaA-) controls. As expected, the DhaA.H272F mutant was capable of generating a covalent alkyl-enzyme intermediate as evidenced by the single fluorescent band near the molecular weight predicted for the GST-DhaA-Flag fusion (FIG. 29, lane 3). As previously observed with the in vitro labeling results, no such product could be detected with either the wild-type or negative control cultures (FIG. 29, lanes 2 and 3) but very faint fluorescent bands migrating at the correct position were again detected with all three DhaA.E130 substituted mutants (FIG. 29, lanes 5-7). These results point to the possibility that the DhaA.E130Q, L and A mutants have the ability to trap covalent alkyl-enzyme intermediates. The efficiency of this reaction, however, appears to proceed at a dramatically reduced rate compared to the DhaA.H272F mutant enzyme.

The results of this mutagenesis study suggest that the DhaA catalytic acid residue DhaA.E130 plays an important structural role in the correct folding of the enzyme. The DhaA protein was clearly sensitive to substitutions at this amino acid position as evidenced by the presence of largely insoluble protein complexes in the DhaA.E130Q, DhaA.E130L and DhaA.E130A crude lysates. Nevertheless, based on SDS-PAGE and immunoblot analyses, a significant quantity of soluble DhaA protein was detected in the cell-free lysates of all three DhaA.E130 mutants.

EXAMPLE IX

Capturing of DhaA.H272F-Flag and DhaA.H272F-Flag *Renilla* Luciferase

Fusion Proteins Expressed in Living Mammalian Cells

Materials and Methods

CHO—K1 cells were plated in 24 well plates (Labsystems) at a density of 30,000 cells/cm$^2$ and transfected with a pCIneo.DhaA.WT-Flag or pCIneo.hRLuc-connector-DhaA.H272F-Flag vector. Twenty-four hours later, media was replaced with fresh media containing 25 µM biotin-$C_{18}H_{32}O_4$—Cl and 0.1% DMSO, or 0.1% DMSO alone, and the cells were placed in a $CO_2$ incubator for 60 minutes. At the end of the incubation, the media was removed, cells were quickly washed with PBS (pH 7.4; four consecutive washes; 1.0 ml/cm$^2$; 5 seconds each) and new media was added to the cells. In some experiments, the media was not changed. The cells were placed back in a $CO_2$ incubator.

After 60 minutes, media was removed, and the cells were collected in PBS (pH=7.4, 200 µl/well, RT) containing protease inhibitors (Sigma #P8340). The cells were lysed by trituriation through a needle (IM1 23GTW). Then, cell lysates were incubated with MagnaBind Streptavidin coated beads (Pierce #21344) according to the manufacturer's protocol. Briefly, cell lysates were incubated with beads for 30 minutes at room temperature (RT) using a rotating disk. Unbound material was collected; beads were washed with PBS (3×500 µl, pH=7.4, RT) and resuspended in SDS-sample buffer (for SDS-PAGE analysis) or PBS (pH=7.4, for determination of R.Luc activity). Proteins were resolved on SDS-PAGE, transferred to a nitrocellulose membrane, analyzed with anti-Flag-Ab or anti-R.Luc-Ab, and bound antibody detected by an enhanced chemiluminescence (ECL) system (Pharmacia-Amersham). Activity of hR.Luc bound to beads was determined using Promega's "*Renilla* Luciferase Assay System" according to the manufacturer's protocol.

Results

Capturing of proteins expressed in living cells allows for analysis of those proteins with a variety of analytic methods/techniques. A number of capturing tools are available although most of those tools require generation of a highly specific antibody or genetically fusing a protein of interest with specific tag peptides/proteins (Jarvik and Telmer, 1998; Ragaut et al., 1999). However, those tags have only limited use for live cell imaging. To capture DhaA.H272F and functional proteins fused to DhaA.H272F, SA-coated beads were used (Savage et al., 1992).

Biotin-$C_{18}H_{32}O_4$—Cl was efficiently hydrolyzed by wild-type DhaA, and covalently bound to DhaA.H272F and DhaA.H272F fusion proteins in vitro and in vivo. Moreover, binding was observed both in *E. coli* and in mammalian cells. Control experiments indicated that about 80% of the DhaA.H272F-Flag protein expressed in CHO—K1 cells was labeled after a 60 minute treatment.

Figure 30A:
FIGS. 30 A-B show Western blot analyses of DhaA-Flag captured on streptavidin (SA) coated beads. CHO—K1 cells transiently expressing DhaA.H272F-Flag were treated with (A) or without (B) biotin-$C_{18}H_{32}O_4$—Cl (25 µM, 0.1% DMSO, 60 minutes, 37° C.). Excess biotin-$C_{18}H_{32}O_4$—Cl was washed out, cells were lysed, and 10 µl of cell lysate was incubated with 5 µl of SA-coated beads (Pierce) for 60 minutes at room temperature (RT). Cell lysates (lane 1), proteins which were not bound to beads (lane 2), and proteins which were bound to beads (lane 3) were resolved on SDS-PAGE, transferred to nitrocellulose membrane, and probed with anti-Flag antibody (Sigma).
Figure 30B:
Figure 30C:
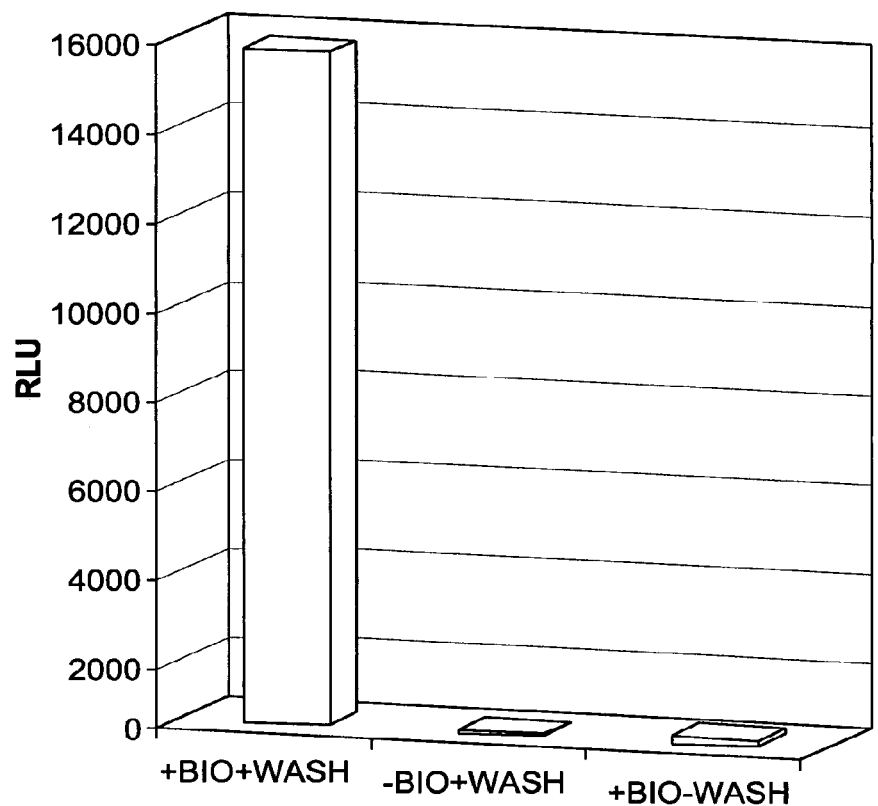
Figure 30D:
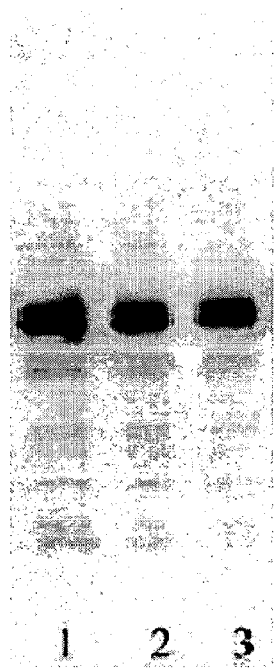

CHO—K1 cells transiently expressing DhaA.H272F-Flag were treated with biotin-$C_{18}H_{32}O_4$—Cl. Biotin-$C_{18}H_{32}O_4$—Cl treated cells were lysed and cell lysates were incubated with SA-coated beads. Binding of DhaA.H272F to beads was analyzed by Western blot using anti-Flag[R] antibody. As shown in FIG. 30D, DhaA.H272F-Flag capturing was not detected in the absence of biotin-$C_{18}H_{32}O_4$—Cl treatment. At the same time, more than 50% of the DhaA.H272F-Flag expressed in cells was captured on SA-coated beads if the cells were treated with biotin-$C_{18}H_{32}O_4$—Cl.

To show the capturing of functionally active proteins fused to DhaA.H272F-Flag, cells were transfected with a vector encoding hR.Luc-connector-DhaA.H272F-Flag, and the luciferase activity captured on the beads measured. As shown in FIG. 30C, significant luciferase activity was detected on beads incubated with a lysate of biotin-$C_{18}H_{32}O_4$—Cl treated cells. At the same time, no luciferase activity was detected on beads incubated with a lysate from cells that were not treated with biotin-$C_{18}H_{32}O_4$—Cl. Moreover, no hR.Luc activity was detected on beads incubated with lysate from the cells treated with biotin-$C_{18}H_{32}O_4$—Cl when free biotin-$C_{18}H_{32}O_4$—Cl was not washed out.

Taken together, these data show that functionally active protein (hR.Luc) fused to the DhaA.H272F can be efficiently captured using biotin-$C_{18}H_{32}O_4$—Cl and SA-coated beads. The capture is biotin-dependent, and can be competed-off by excess of biotin-$C_{18}H_{32}O_4$—Cl. As a significant inhibitory effect of the beads on the hR.Luc activity was observed (data not shown), SDS-PAGE and Western blot analysis with anti-R.Luc antibody were used to estimate the efficiency of capture of hR.Luc-connector-DhaA.H272F-Flag fusion protein. As shown in FIG. 30D, more than 50% of hR.Luc-connector-DhaA.H272F-Flag fusion protein can be captured in biotin-dependent manner. This is in good agreement with the capturing efficiency of DhaA.H272F-Flag (see FIG. 30A).

EXAMPLE X

Optimized DhaA Gene

DhaA General Sequence Design

A synthetic DhaA.H272F gene was prepared which had a human codon bias, low CG content, selected restriction enzyme recognition sites and a reduced number of transcription regulatory sites. Relative to the amino sequence encoded by a wild-type DhaA gene which lacks a signal sequence (SEQ ID NO:51), and/or to DhaA.H272F, the amino acid sequence of a codon-optimized DhaA gene and flanking sequences included: 1) a Gly inserted at position 2, due to introduction of an improved Kozak sequence (GCCAC-CATGG; SEQ ID NO:45) and a BamHI site (thus the H272F active site mutation in DhaA mutants with the Gly insertion is at position 273); 2) a A292G substitution due to introduction of a SmaI/XmaI/AvaI site which, in the DhaA mutant with the Gly insertion, is at position 293; 3) the addition of Ala-Gly at the C-terminus due to introduction of a NaeI (NgoMIV) site; 4) the addition of NheI, PvuII, EcoRV and NcoI sites in the 5' flanking sequence; 5) the addition of NNNN in the 5' flanking sequence to eliminate search algorithm errors at the end and to maintain the ORF1 (i.e., NNN-NGC-TAG-CCA-GCT-GGC-GAT-ATC-GCC-ACC-ATG-GGA; SEQ ID NO:46); 6) at the 3' end a NotI site, the addition of NNNN to eliminate search algorithm errors at the end, a PacI site with ORF Leu-Ile-Lys, and two stop codons, at least one of which is a TAA (i.e., TAATAGTTAATTAAGTAAGCGGC-CGCNNNN; SEQ ID NO:47).

SEQ ID NO:51 has the following sequence:

```
atgtcagaaatcggtacaggcttccccttcgaccccattatgtggaa
gtcctgggcgagcgtatgcactacgtcgatgttggaccgcgggatggc
acgcctgtgctgttcctgcacggtaacccgacctcgtcctacctgtgg
cgcaacatcatcccgcatgtagcaccgagtcatcggtgcattgctcca
gacctgatcgggatgggaaaatcggacaaaccagacctcgattatttc
ttcgacgaccacgtccgctacctcgatgccttcatcgaagccttgggt
ttggaagaggtcgtcctggtcatccacgactgggctcagctctcgga
ttccactgggccaagcgcaatccggaacgggtcaaaggtattgcatgt
atggaattcatccggcctatcccgacgtgggacgaatggccggaattc
gcccgtgagaccttccaggccttccggaccgccgacgtcggccgagag
ttgatcatcgatcagaacgctttcatcgagggtgcgctcccgaaatgc
gtcgtccgtccgcttacggaggtcgagatggaccactatcgcgagccc
ttcctcaagcctgttgaccgagagccactgtggcgattcccaacgag
ctgcccatcgccggtgagcccgcgaacatcgtcgcgctcgtcgaggca
tacatgaactggctgcaccagtcacctgtcccgaagttgttgttctgg
ggcacaccggcgtactgatccccccggccgaagccgcgagacttgcc
gaaagcctccccaactgcaagacagtggacatcggcccgggattgcac
tacctccaggaagacaacccggaccttatcggcagtgagatcgcgcgc
tggctccccgcactctag
```

Codon Selection

Codon usage data was obtained from the Codon Usage Database (http://www.kazusa.or.jp/codon/), which is based on: GenBank Release 131.0 of 15 Aug. 2002 (See, Nakamura et al., 2000). Codon usage tables were downloaded for: HS: *Homo sapiens* [gbpri] 50,031 CDS's (21,930,294 codons); MM: *Mus musculus* [gbrod] 23,113 CDS's (10,345,401 codons); EC: *Escherichia coli* [gbbct] 11,985 CDS's (3,688,954 codons); and EC K12: *Escherichia coli* K12 [gbbct]-4, 291 CDS's (1,363,716 codons). HS and MM were compared and found to be closely similar, thus the HS table was used. EC and EC K12 were compared and found to be closely similar, therefore the EC K12 table was employed.

The overall strategy for selecting codons was to adapt codon usage for optimal expression in mammalian cells while avoiding low-usage *E. coli* codons. One "best" codon was selected for each amino acid and used to back-translate the desired protein sequence to yield a starting gene sequence. Another selection criteria was to avoid high usage frequency HS codons which contain CG dinucleotides, as methylation of CG has been implicated in transcriptional gene regulation and can cause down-regulation of gene expression in stable cell lines. Thus, all codons containing CG (8 human codons) and TA (4 human codons, except for Tyr codons) were excluded. Codons ending in C were also avoided as they might form a CG with a downstream codon. Of the remaining codons, those with highest usage in HS were selected, unless a codon with a slightly lower usage had substantially higher usage in *E. coli*.

DhaA Gene Sequences

To generate a starting DhaA sequence, codon usage tables in Vector NTI 8.0 (Informax) were employed. The DhaA.v2.1 protein sequence (SEQ ID NO:48) was back translated to create a starting gene sequence, hDhaA.v2.1-0, and flanking regions were then added, as described above, to create hDhaA.v2.1-0F (SEQ ID NO:49).

DhaA.v2.1:
(SEQ ID NO: 48)
MGSEIGTGFPFDPHYVEVLGERMHYVDVGPRDGTPVLFLHGNPTSSYL

WRNIIPHVAPSHRCIAPDLIGMGKSDKPDLDYFFDDHVRYLDAFIEAL

GLEEVVLVIHDWGSALGFHWAKRNPERVKGIACMEFIRPIPTWDEWPE

FARETFQAFRTADVGRELIIDQNAFIEGALPKCVVRPLTEVEMDHYRE

PFLKPVDREPLWRFPNELPIAGEPANIVALVEAYMNWLHQSPVPKLLF

WGTPGVLIPPAEAARLAESLPNCKTVDIGPGLFYLQEDNPDLIGSEIA

RWLPGLAG hDhaA.v2.1-0F:
(SEQ ID NO: 49)
NNNNGCTAGCCAGCTGGCGATATCGCCACCATGGGATCCGAGATTGGGA

CAGGGTTTCCTTTTGATCCTCATTATGTGGAGGTGCTGGGGAGAGAAT

GCATTATGTGGATGTGGGCCTAGAGATGGGACACCTGTGCTGTTTCTG

CATGGGAATCCTACATCTTCTTATCTGTGGAGAAATATTATTCCTCATG

TGGCTCCTTCTCATAGATGTATTGCTCCTGATCTGATTGGGATGGGGAA

GTCTGATAAGCCTGATCTGGATTATTTTTTTGATGATCATGTGAGATAT

CTGGATGCTTTTATTGAGGCTCTGGGGCTGGAGGAGGTGGTGCTGGTGA

TTCATGATTGGGGGTCTGCTCTGGGGTTTCATTGGGCTAAGAGAAATCC

TGAGAGAGTGAAGGGGATTGCTTGTATGGAGTTTATTAGACCTATTCCT

ACATGGGATGAGTGGCCTGAGTTTGCTAGAGAGACATTTCAGGCTTTTA

GAACAGCTGATGTGGGGAGAGAGCTGATTATTGATCAGAATGCTTTTAT

TGAGGGGGCTCTGCCTAAGTGTGTGGTGAGACCTCTGACAGAGGTGGAG

ATGGATCATTATAGAGAGCCTTTTCTGAAGCCTGTGGATAGAGAGCCTC

TGTGGAGATTTCCTAATGAGCTGCCTATTGCTGGGGAGCCTGCTAATAT

TGTGGCTCTGGTGGAGGCTTATATGAATTGGCTGCATCAGTCTCCTGTG

CCTAAGCTGCTGTTTTGGGGGACACCTGGGGTGCTGATTCCTCCTGCTG

AGGCTGCTAGACTGGCTGAGTCTCTGCCTAATTGTAAGACAGTGGATAT

TGGGCCTGGGCTGTTTTATCTGCAGGAGGATAATCCTGATCTGATTGGG

TCTGAGATTGCTAGATGGCTGCCCGGGCTGGCCGGCTAATAGTTAATTA

AGTAAGCGGCCGCNNNN

Further Optimization

Programs and databases used for identification and removal of sequence motifs were from Genomatix Software GmbH (Munich, Germany, http://www.genomatix.de): GEMS Launcher Release 3.5.1 (April 2003), MatInspector professional Release 6.1 (January 2003), Matrix Family Library Ver 3.1.1 (April 2003, including 318 vertebrate matrices in 128 families), ModelInspector professional Release 4.8 (October 2002), Model Library Ver 3.1 (March 2003, 226 modules), SequenceShaper tool, and User Defined Matrices. The sequence motifs to be removed from starting gene sequences in order of priority were restriction enzyme recognition sequences listed below; transcription factor binding sequences including promoter modules (i.e., 2 transcription factor binding sites with defined orientation) with a default score or greater, and vertebrate transcription factor binding sequences with a minimum score of =0.75/matrix=optimized; eukaryotic transcription regulatory sites including a Kozak sequence, splice donor/acceptor sequences, polyA addition sequences; and prokaryotic transcription regulatory sequences including E. coli promoters and E. coli RBS if less than 20 bp upstream of a Met codon.

User-defined Matrices

Subset DhaA

Format: Matrix name (core similarity threshold/matrix similarity threshold): U$AatII (0.75/1.00), U$BamHI (0.75/1.00), U$BglI (0.75/1.00), U$BglII (0.75/1.00), U$BsaI (0.75/1.00), U$BsmAI (0.75/1.00), U$BsmBI (0.75/1.00), U$BstEII (0.75/1.00), U$BstXI (0.75/1.00), U$Csp451 (0.75/1.00), U$CspI (0.75/1.00), U$DraI (0.75/1.00), U$EC-P-10 (1.00/Optimized), U$EC-P-35 (1.00/Optimized), U$EC-Prom (1.00/Optimized), U$EC-RBS (0.75/1.00), U$EcoRI (0.75/1.00), U$EcoRV (0.75/1.00), U$HindIII (0.75/1.00), U$Kozak (0.75/Optimized), U$KpnI (0.75/1.00), U$MluI (0.75/1.00), U$NaeI (0.75/1.00), U$NcoI (0.75/1.00), U$NdeI (0.75/1.00), U$NheI (0.75/1.00), U$NotI (0.75/1.00), U$NsiI (0.75/1.00), U$PacI (0.75/1.00), U$PflMI (0.75/1.00), U$PmeI (0.75/1.00), U$PolyAsig (0.75/1.00), U$PstI (0.75/1.00), U$PvuII (0.75/1.00), U$SacI (0.75/1.00), U$SacII (0.75/1.00), U$SalI (0.75/1.00), U$SfiI (0.75/1.00), U$SgfI (0.75/1.00), U$SmaI (0.75/1.00), U$SnaBI (0.75/1.00), U$SpeI (0.75/1.00), U$Splice-A (0.75/Optimized), U$Splice-D (0.75/Optimized), U$XbaI (0.75/1.00), U$XcmI (0.75/1.00), U$XhoI (0.75/1.00), and ALL vertebrates.lib.

Subset DhaA-EC

Without E. coli specific sequences: U$AatII (0.75/1.00), U$BamHI (0.75/1.00), U$BglI (0.75/1.00), U$BglII (0.75/1.00), U$BsaI (0.75/1.00), U$BsmAI (0.75/1.00), U$BsmBI (0.75/1.00), U$BstEII (0.75/1.00), U$BstXI (0.75/1.00), U$Csp451 (0.75/1.00), U$CspI (0.75/1.00), U$DraI (0.75/1.00), U$EcoRI (0.75/1.00), U$EcoRV (0.75/1.00), U$HindIII (0.75/1.00), U$Kozak (0.75/Optimized), U$KpnI (0.75/1.00), U$MluI (0.75/1.00), U$NaeI (0.75/1.00), U$NcoI (0.75/1.00), U$NdeI (0.75/1.00), U$NheI (0.75/1.00), U$NotI (0.75/1.00), U$NsiI (0.75/1.00), U$PacI (0.75/1.00), U$PflMI (0.75/1.00), U$PmeI (0.75/1.00), U$PolyAsig (0.75/1.00), U$PstI (0.75/1.00), U$PvuII (0.75/1.00), U$SacI (0.75/1.00), U$SacII (0.75/1.00), U$SalI (0.75/1.00), U$SfiI (0.75/1.00), U$SgfI (0.75/1.00), U$SmaI (0.75/1.00), U$SnaBI (0.75/1.00), U$SpeI (0.75/1.00), U$Splice-A (0.75/Optimized), U$Splice-D (0.75/Optimized), U$XbaI (0.75/1.00), U$XcmI (0.75/1.00), U$XhoI (0.75/1.00), and ALL vertebrates.lib.

Strategy for Removal of Sequence Motifs

The undesired sequence motifs specified above were removed from the starting gene sequence by selecting alternate codons that allowed retention of the specified protein and flanking sequences. Alternate codons were selected in a way to conform to the overall codon selection strategy as much as possible.

A. General Steps

Identify undesired sequence matches with MatInspector using matrix family subset "DhaA" or "DhaA-EC" and with ModelInspector using default settings.

Identify possible replacement codons to remove undesired sequence matches with SequenceShaper (keep ORF).

Incorporate all changes into a new version of the synthetic gene sequence and re-analyze with MatInspector and ModelInspector.

B. Specific Steps

Remove undesired sequence matches using subset "DhaA-EC" and SequenceShaper default remaining thresholds (0.70/Opt-0.20).

For sequence matches that cannot be removed with this approach use lower SequenceShaper remaining thresholds (e.g., 0.70/Opt-0.05).

For sequence matches that still cannot be removed, try different combinations of manually chosen replacement codons (especially if more than 3 base changes might be needed). If that introduces new sequence matches, try to remove those using the steps above (a different starting sequence sometimes allows a different removal solution).

Use subset "DhaA" to check whether problematic *E. coli* sequences motifs were introduced, and if so try to remove them using an analogous approach to that described above for non *E. coli* sequences.

Use an analogous strategy for the flanking (non-open reading frame) sequences.

C. Identification and Removal of Putative CpG Islands

Software used: EMBOSS CpGPlot/CpGReport http://www.ebi.ac.uk/emboss/cpgplot/index.html) (see, Gardiner-Garden et al., 1987).

Parameters: default (modified): Window: 100; Step: 1; Obs/Exp: 0.6; MinPC: 50; Length: 100; Reverse: no; Complement: no. After the removal of undesired sequence motifs, the gene sequence was checked for putative CpG islands of at least 100 bases using the software described above. If CpG islands were identified, they were removed by selecting, at some of the CG di-nucleotide positions, alternate codons that allowed retention of the specified protein and flanking sequences, but did not introduce new undesired sequence motifs.

D. Restriction Sites

A unique MunI/MfeI (C'AATTG) site was introduced to allow removal of the C-terminal 34 amino acids, including a putative myristylation site (GSEIAR) near the C-terminus. Another unique site, a NruI site, was introduced to allow removal of the C-terminal 80-100 amino acids.

Results

Sequence Comparisons

An optimized DhaA gene has the following sequence:

```
hDhaA.v2.1-6F (FINAL, with flanking sequences)
                                  (SEQ ID NO: 50)
NNNNGCTAGCCAGCTGGCgcgGATATCGCCACCATGGGATCCGAGATT GGGACAGGGTTcCCTTTTGATCCTCAcTATGTtGAaGTGCTGGGgGAa AGAATGCAcTAcGTGGATGTGGGGCCTAGAGATGGGACcCCaGTGCTG TTcCTcCAcGGGAAcCCTACATCTAgcTAcCTGTGGAGaAAtATTATa CCTCATGTtGCTCCTagtCATAGgTGcATTGCTCCTGATCTGATcGGG ATGGGGAAGTCTGATAAGCCTGActtaGAcTAcTTTTTTGATGAtCAT GTtcGATActTGGATGCTTTcATTGAGGCTCTGGGGCTGGAGGAGGTG GTGCTGGTGATaCAcGAcTGGGGGTCTGCTCTGGGGTTTCAcTGGGCT AAaAGgAATCCgGAGAGAGTGAAGGGGATTGCTTGcATGGAgTTTATT cGACCTATTCCTACtTGGGAtGAaTGGCCaGAGTTTGCcAGAGAGACA
```

-continued
```
TTTCAaGCcTTTAGAACtGCcGATGTGGGcAGgGAGCTGATTATaGAc

CAGAATGCTTTcATcGAGGGGGCTCTGCCTAAaTGTGTaGTcAGACCT

CTcACtGAaGTaGAGATGGAcCATTATAGAGAGCCcTTTCTGAAGCCT

GTGGATcGcGAGCCTCTGTGGAGgTTtCCaAATGAGCTGCCTATTGCT

GGGGAGCCTGCTAATATTGTGGCTCTGGTGGAaGCcTATATGAAcTGG

CTGCATCAGagTCCaGTGCCcAAGCTaCTcTTTTGGGGGACtCCgGGa

GTtCTGATTCCTCCTGCcGAGGCTGCTAGACTGGCTGAaTCcCTGCCc

AAtTGTAAGACcGTGGAcATcGGcCCtGGgCTGTTTTAcCTcCAaGAG

GAcAAcCCTGATCTcATcGGGTCTGAGATcGCacGgTGGCTGCCCGGG

CTGGCCGGCTAATAGTTAATTAAGTAggCGGCCGCNNNN
```

A comparison of the nucleic acid sequence identity of different DhaA genes (without flanking sequences) is shown in Table III.

TABLE III

|  | DhaA | DhaA.v2.1 | hDhaA.v.2.1-0 | hDhaA.v2.1-6 |
|---|---|---|---|---|
| DhaA | 100 | 98 | 72 | 75 |
| DhaA.v2.1[a] |  | 100 | 74 | 76 |
| hDhaA.v.2.1-0[b] |  |  | 100 | 88 |
| hDhaA.v2.1-6 |  |  |  | 100 |

[a]Gly added at position 2, H272F, A292G, Ala-Gly added to C-terminus
[b]codon optimized The GC content of different DhaA genes (without flanking sequences) is provided in Table IV.

TABLE IV

|  | GC content | CG di-nucleotides |
|---|---|---|
| *H. sapiens* | 53% |  |
| DhaA | 60% | 85 |
| DhaA.v2.1 | 60% | 87 |
| hDhaA.v.2.1-0 | 49% | 3 |
| hDhaA.v2.1-6 | 52% | 21 |

Vertebrate transcription factor binding sequence families (core similarity: 0.75/matrix similarity: opt) and promoter modules (default parameters: optimized threshold or 80% of maximum score) found in different DhaA genes are shown in Table V.

TABLE V

| Gene name | TF binding sequences 5' F/ORF/3' F | Promoter modules 5' F/ORF/3' F |
|---|---|---|
| DhaA | —/82/— | —/5/— |
| DhaA.v2.1-F | 3/82/12 | 0/5/0 |
| hDhaA.v.2.1-0F | 3/87/12 | 0/0/0 |
| hDhaA.v2.1-6F | 1/3/8 | 0/0/0 |

Note:
3 by insertion before EcoRV in hDhaA.v.2.1-OF and in hDhaA.v2.1-6F to remove 5' binding sequence matches in 3' flanking region.

The remaining transcription factor binding sequence matches in hDhaA.v2.1-6F included in the 5' flanking region: Family: V$NEUR (NeuroD, Beta2, HLH domain), best match: DNA binding site for NEUROD1 (BETA-2/E47 dimer) (MEDLINE 9108015); in the open reading frame: Family: V$GATA (GATA binding factors), best match: GATA-binding factor 1 (MEDLINE 94085373), Family: V$PCAT (Promoter CCAAT binding factors), best match: cellular and viral CCAAT box, (MEDLINE 90230299), Family: V$RXRF (RXR heterodimer binding sites), best match: Farnesoid X-activated receptor (RXR/FXR dimer) (MEDLINE 11792716); and in the 3' flanking region: Family: V$HNF1 (Hepatic Nuclear Factor 1), best match: Hepatic nuclear factor 1 (MEDLINE 95194383), Family: V$BRNF (Brn POU domain factors), best match: POU transcription factor Brn-3 (MEDLINE 9111308), Family: V$RBIT (Regulator of B-Cell IgH transcription), best match: Bright, B cell regulator of IgH transcription (MEDLINE 96127903), Family: V$CREB (Camp-Responsive Element Binding proteins), best match: E4BP4, bZIP domain, transcriptional repressor (MEDLINE 92318924), Family: V$HOMS (Homeodomain subfamily S8), best match: Binding site for S8 type homeodomains (MEDLINE 94051593), Family: V$NKXH (NKX/DLX—Homeodomain sites), best match: DLX-1, -2, and -5 binding sites (MEDLINE 11798166), Family: V$TBPF (Tata-Binding Protein Factor), best match: Avian C-type LTR TATA box (MEDLINE 6322120), and Family: V$NKXH (NKX/DLX—Homeodomain sites), best match: Prostate-specific homeodomain protein NKX3.1 (MEDLINE 10871372).

The other sequence motifs remaining in hDhaA.v2.1-6F in the open reading frame were for an E. coli RBS (AAGG) 11b upstream of a Met codon which was not removed due to retain the protein sequence (Lys-Gly: AA(A/G)-GGN), and a BsmAI restriction site (GTCTC) which was not removed due to introduction of transcription factor binding site sequences.

The putative CpG islands in the coding sequence for each of the DhaA genes was analyzed as in EMBOSS CpGPlot/CpGReport with default parameters, and the results are shown in Table VI.

TABLE VI

| Gene name | CpG Islands >100 bp | Length by (location in ORF) |
|---|---|---|
| DhaA | 1 | 775 by (49 ... 823) |
| DhaA.v2.1 | 1 | 784 by (49 ... 832) |
| hDhaA.v.2.1-0 | 0 | — |
| hDhaA.v2.1-6 | 0 | — |

REFERENCES

Ambler et al., *Biochem. J.*, 276:4710 (1991).
Ausubel et al., *Current Protocols in Molecular Biology*, Vol. III, A.1(3-4), Supplement 38 (1997).
Chalfie, M. and Kain, S. R., eds., *GFP: Green Fluorescent Protein Strategies and Applications* (Wiley, New York, 1998).
Cubitt et al., *Trends Biochem. Sci.*, 20:448 (1995).
Eu and Andrade, *Luminescence*, 16:57-63 (2001).
Farinas et al., *J. Biol. Chem.*, 274:7603 (1999).
Franken et al., *EMBO J.*, 10:1297 (1991).
Gardiner-Garden et al., *J. Mol. Biol.*, 196:261 (1987).
Griffin et al., *Science*, 281:269 (1998).
Hermanson, *Bioconjugate Techniques*, Academic Press, San Diego, Calif. (1996).
Ho et al., *Gene*, 77:51 (1989).
Holloway et al., *J. Microbiol. Methods*, 32:31 (1998).
Hynkova et al., *FEBS Lett.*, 446:177 (1999).
Janssen et al., *Eur. J. Biochem.*, 171:67 (1988).
Janssen et al., *J. Bacteriol.*, 171:6791 (1989).
Jarvik and Telmer, *Ann. Rev. Genet.*, 32:601-618 (1998).
Keppler et al., *Nature Biotechnology*, 21:86 (2003).
Keuning et al., *J. Bacteriol.*, 163:635 (1985).
Kneen et al., *Biophys. J.*, 74:1591 (1998).
Krooshof et al., *Biochemistry*, 36:9571 (1997).
Kulakova et al., *Microbiology*, 143:109 (1997).
Lakowicz, J. R. Principles of Fluorescence Spectroscopy, New York: Plenum Press (1983).
Llopis et al., *Proc. Natl. Acad. Sci. USA*, 95:6803 (1998).
Miesenböck et al., *Nature*, 394:192 (1998).
Minasov et al., *J. Am. Chem. Soc.*, 124:5333 (2002).
Miyawaki et al., *Nature*, 388:882 (1967).
Nagata et al., *Appl. Environ. Microbiol.*, 63:3707 (1997).
Nakamura et al., *Nucl. Acids. Res.*, 28:292 (2000).
Newman et al., *Biochemistry*, 38, 16105 (1999).
Ormö et al., *Science*, 273:1392 (1996).
Pries et al., *J. Biol. Chem.*, 270:10405 (1995).
Ragaut et al., *Nat. Biotechnol.*, 17:1030-1032 (1999).
Rosomer et al., *J. Biol. Chem.*, 272:13270 (1997).
Sallis et al., *J. Gen. Microbiol.*, 136:115 (1990).
Sambrook et al., Cold Spring Harbor Laboratory Press, Cold Spring Harbor, N.Y. 1989.
Sanger et al., *Proc. Natl. Acad. Sci. U.S.A.*, 74:5463 (1977).
Savage et al., *Avidin-Biotin Chemistry: A Handbook* (Pierce Chemical Company, Rockford, Ill.) (1992).
Schindler, *Biochemistry*, 38:5772 (1999).
Scholtz et al., *J. Bacteriol.*, 169:5016 (1987).
Silverman, Mechanism-based enzyme in activation, in *Methods Enzymology*, 249:240 (1995).
Stroffekova et al., *Eur. J. Physiol.*, 442:859 (2001).
Tsien, *Ann. Rev. Biochem.*, 67:509 (1998).
Yokota et al., *J. Bacteriol.*, 169:4049 (1987).
Zawadzke et al., *Protein Engineering*, 8:1275 (1995).
Zlokarnik et al., *Science*, 279:84 (1998).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A complex of a radionuclide and a compound of formula (I): R-linker-A-X, wherein R comprises a metal ion chelator, wherein the linker is a multiatom straight or branched chain including C, N, S and/or O and comprising no more than 30 carbon atoms, wherein A-X is a substrate for a dehalogenase, wherein A is $(CH_2)_n$ and n=2-10, and wherein X is a halogen.

2. The complex of claim 1, which is a substrate for a *Rhodococcus* dehalogenase.

3. The complex of claim 1, wherein X is Cl or Br.

4. The complex of claim 1, wherein the linker separates R and A by at least 11 atoms.

5. The complex of claim 1, wherein the radionuclide is separated from A-X by up to 500 angstroms.

6. The complex of claim 1, wherein the linker comprises —$C(O)NH(CH_2CH_2O)_y$, wherein y=2-8.

7. A method to label a cell, comprising:
   (a) contacting a cell comprising a mutant dehalogenase with the complex of claim 1, wherein the mutant dehalogenase comprises at least one amino acid substitution relative to the corresponding wild-type dehalogenase, wherein the at least one amino acid substitution results in the mutant dehalogenase forming a bond with the substrate which is more stable than the bond formed between the corresponding wild-type dehalogenase and the substrate, wherein the at least one amino acid substitution in the mutant dehalogenase is a substitution (i) at an amino acid residue in the corresponding wild-type dehalogenase that is associated with activating a water molecule which cleaves the bond formed between the corresponding wild-type dehalogenase and the substrate or (ii) at an amino acid residue in the corresponding wild-type dehalogenase that forms an ester intermediate with the substrate; and
   (b) incubating the cell with the complex, wherein the incubation results in the cell being labeled with the radionuclide in the complex.

8. The method of claim 7, wherein the substrate is a substrate for a *Rhodococcus* dehalogenase.

9. The method of claim 7, wherein X is Cl or Br.

10. The method of claim 7, wherein the linker comprises —$C(O)NH(CH_2CH_2O)_y$, wherein y=2-8.

11. A method to detect or determine the presence or amount of a mutant dehalogenase, comprising:
   a) contacting a mutant dehalogenase with the complex of claim 1, wherein the mutant dehalogenase comprises at least one amino acid substitution relative to the corresponding wild-type dehalogenase, wherein the at least one amino acid substitution results in the mutant dehalogenase forming a bond with the substrate which is more stable than the bond formed between the corresponding wild-type dehalogenase and the substrate, wherein the at least one amino acid substitution in the mutant dehalogenase is a substitution (i) at an amino acid residue in the corresponding wild-type dehalogenase that is associated with activating a water molecule which cleaves the bond formed between the corresponding wild-type dehalogenase and the substrate or (ii) at an amino acid residue in the corresponding wild-type dehalogenase that forms an ester intermediate with the substrate; and
   b) detecting or determining the presence or amount of the radionuclide, thereby detecting or determining the presence or amount of the mutant dehalogenase.

12. The method of claim 11, wherein the substrate is a substrate for a *Rhodococcus* dehalogenase.

13. The method of claim 11, wherein X is Cl or Br.

14. The method of claim 11, wherein the linker comprises —$C(O)NH(CH_2CH_2O)_y$, wherein y=2-8.

* * * * *